United States Patent
Lampilas et al.

(10) Patent No.: US 7,439,253 B2
(45) Date of Patent: *Oct. 21, 2008

(54) HETEROCYCLIC COMPOUNDS, THEIR PREPARATION AND THEIR USE AS MEDICAMENTS, IN PARTICULAR AS ANTIBACTERIALS AND BETA-LACTAMASE INHIBITORS

(75) Inventors: Maxime Lampilas, St Cloud (FR); Branislav Musicki, Paris (FR); Michel Klich, Villemomble (FR); David Alan Rowlands, Poissy (FR)

(73) Assignee: Novexel, Romainville (FR)

( * ) Notice: Subject to any disclaimer, the term of this patent is extended or adjusted under 35 U.S.C. 154(b) by 240 days.

This patent is subject to a terminal disclaimer.

(21) Appl. No.: 10/727,911

(22) Filed: Dec. 4, 2003

(65) Prior Publication Data

US 2004/0157826 A1    Aug. 12, 2004

Related U.S. Application Data

(60) Provisional application No. 60/484,323, filed on Jul. 2, 2003.

(30) Foreign Application Priority Data

Dec. 6, 2002    (FR)    .................................. 02 15428

(51) Int. Cl.
*A61P 31/00* (2006.01)
*A61K 31/44* (2006.01)
*C07D 471/00* (2006.01)

(52) U.S. Cl. .................. 514/292; 514/293; 514/210.05; 514/210.08; 514/210.1; 514/210.12; 514/210.13; 514/210.15; 546/82; 546/83; 546/84

(58) Field of Classification Search .................. 514/292, 514/293; 546/82, 83, 84
See application file for complete search history.

(56) References Cited

U.S. PATENT DOCUMENTS 5,932,587 A    8/1999    Schmeck et al. ............. 514/278

FOREIGN PATENT DOCUMENTS

| EP | 0 818 197 A1 | 1/1998 |
|---|---|---|
| FR | 2 676 230 | 11/1992 |
| WO | WO 95/18129 | 7/1995 |
| WO | WO 00/00479 | 1/2000 |
| WO | WO 00/63187 | 10/2000 |
| WO | WO0210172 | 2/2002 |
| WO | WO02100860 | 12/2002 |
| WO | WO03063864 | 8/2003 |

OTHER PUBLICATIONS

Chen et al, Synthesis of N-substituted 1,6-Dihydro-3(2H)-Pyridinones and 1-Acyl-3-Piperidones, Heterocycles, vol. 22, No. 12, 1984, pp. 2769-2773.

Hall, Jr. et al, 3-Isopropyl-1,3-diazabicyclo[3,3.1]nonan-2-one, a Simple Bicyclic Urea with a Bridgehead Nitrogen Atom, J. Org. Chem., vol. 37, Issue 5, 1972, pp. 697-699.

Hall, Jr. et al, Anti-Bredt Bridgehead Nitrogen Compounds in Ring-Opening Polymerization, Chemical Reviews, vol. 83, Issue 5, 1983, pp. 549-555.

Hall, Jr. et al, Anti-Bredt Molecules. 3.1a 3-Oxa-1-azabicyclo[3.3.1]nonan-2-one and 6-Oxa-1-azabicyclo[3.2.1]octan-7-one, two Atome-Bridged Bicyclic Uretyhanes Possessing Bridgehead Nitrogen, J. Org. Chem., vol. 45, Issue 26, 1980, pp. 5325-5326.

Itoh, Synthesis and Structure of 4-Substituted Decahydroisoquinoline Derivatives, Chem. Pharm. Bull., vol. 16, Issue 3, 1968, pp. 455-470.

Nicolaou et al, New Synthetic Technology for the Rapid Construction of Novel Heterocycles—Part 2. The Reaction of IBX with Anilides and Related Compounds, Chem. Int. Ed. 2000, vol. 39, Issue 3, 2000, pp. 625-628.

Pennington et al, Preparation and cyclization of substituted 1-anilino-3-halo-2- propanols and their conversion to indoles, Chem. Abs. RN 3189-20-6 and Journal of Organic Chemistry, vol. 30, No. 8, 1965, pp. 2801-1804.

Shiotanti et al, Studies on Diazabenzobicyclo[3.3.1]nonane System, M+1 Syntheses of 1,2,3,4-Tetrahydro-6H-1,5-methanobenzo[d][1,2] diazocine Derivatives, Chemical Pharm. Bull., vol. 15, Issue 1, 1967, pp. 88-93.

Triebs, et al, Experiments for the preparation of azatropolones. I. Disubstituted 1-aza-4,5-cycloheptanedione and 5-azatropolone, Chem. Abs. RN 106478-62-0 and Journal Fuer Praktische Chemie (LEIPZIG), vol. 14, 1961, pp. 208-217.

Booker-Milburn, K.I. et al., "Azabenzocycloheptenones. Part 20. Synthesis and utilisation of 4-amino-1,2,3,4-tetrahydro-1(1H)-benzazepines," J. Chem. Soc., Perkin Trans. 1: Organic and Bio-Organic Chemistry, pp. 3261-3273 (1997).*

(Continued)

*Primary Examiner*—Brenda L Coleman
(74) *Attorney, Agent, or Firm*—Harness, Dickey & Pierce, P.L.C.

(57) ABSTRACT

The invention relates to novel heterocyclic compounds of general formula (I), and their salts with a base or an acid:

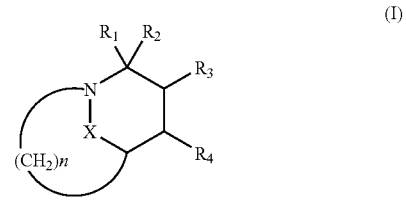

The invention also relates to a method for preparing these compounds, and to their use as medicaments, in particular as antibacterials and β-lactamase inhibitors.

23 Claims, No Drawings

OTHER PUBLICATIONS

Elliott, R. et al., "Syntheses and stereochemistry of 4-hydroxy tetrahydroisoquinolines in the 1-benzyl and 1-phenethyl series. Efficient routes to isopavines and homoisopavines," Tetrahedron Letters, vol. 21, pp. 4633-4636 (1980).*

Heier, R.F. et al., "An asymmetric synthesis of (R)-5,6-dihydro-5-(methylamino)-4H-imidazo-[4,5,1-ij]quinolin-2(1H)-one and its [2-14C]- and [6,7-3H2]-labeled forms," CAPLUS Database, Chemical Abstracts Service, Columbus, Ohio (1997).*

Heier, R.F. et al., "Synthesis and Biological Activities of (R)-5,6-Dihydro-N,N-dimethyl-4H-imidazo[4,5,1-ij]quinolin-5-amine and Its Metabolites," J. Med. Chem., vol. 40, pp. 639-646 (1997).*

Masumoto, S. et al., "Preparation of tricyclic quinazlinediones as poly (ADP-ribose) polymerase inhibitors," CAPLUS Database, Chemical Abstracts Service, Columbus, Ohio (2001).*

Moon, M.W. et al., "Dopaminergic and Serotonergic Activities of Imidazoquiolinones and Related Compounds," J. Med. Chem., vol. 35, pp. 1076-1092 (1992).*

Moon, M.W. et al., "Medicinal chemistry of imidazoquinolinone dopamine receptor agonists," CAPLUS Database, Chemical Abstracts Service, Columbus, Ohio (1994).*

Moon, M.W. et al., "Synthesis of tritium-labeled (R)-5-(di[2,3-3H2]propylamino)-5,6-dihydro-4H-imidazo-[4,5,1-ij]quinolin-2(1H)-one([3H]U-86170) and (R)-5-([2,3-3H2]propylamino)-5,6-dihydro-4H-imidazo-[4,5,1-ij]quinolin-2(1H)-one([3H]U-91356)," CAPLUS Database, Chemical Abstracts Service, Columbus, Ohio (1993).*

Nagasaka, T. et al., "Preparation of 1,4-dihydro-4-phenyl-3,5-pyridinedicarboxylic acids as calcium antagonists," CAPLUS Database, Chemical Abstracts Service, Columbus, Ohio (1994).*

Romero, A.G. et al., "Oxidative Cyclization of Acyclic Ureas with Bis(trifluoroacetoxy)iodobenzene to Generate N-Substituted 2-Benzimidazolinones," Tetrahedron Letters, vol. 37, No. 14, pp. 2361-2364 (1996).*

Tirk, I. et al., "Hydroxyiminoisoquinolin-3(2H)-Ones, VI: Synthesis and Biological Activity of Some Aminoisoquinoline Derivatives," Acto Chimica Hungarica, vol. 124, No. 2, pp. 195-207 (1987).*

Zhou, B. et al., "Studies Directed to the Total Synthesis of ET 743 and Analogues Thereof: An Expeditious Route to the ABFGH Subunit," Org. Lett., vol. 4, No. 1, pp. 43-46 (2002).*

HETEROCYCLIC COMPOUNDS, THEIR PREPARATION AND THEIR USE AS MEDICAMENTS, IN PARTICULAR AS ANTIBACTERIALS AND BETA-LACTAMASE INHIBITORS

CROSS-REFERENCE TO RELATED APPLICATIONS

This application claims the benefit of U.S. Provisional Application No. 60/484,323, filed Jul. 2, 2003, as well as the benefit of priority from French Patent Application No. 02 15428, filed Dec. 6, 2002.

BACKGROUND OF THE INVENTION

The invention relates to novel heterocyclic compounds, their preparation and their use as medicaments, in particular as antibacterials.

The preparation of a bicyclic derivative having the empirical formula $C_{10}H_{18}N_2O$ is described in particular in the journal J. Org. Chem., Vol. 37, No. 5, 1972, pages 697 to 699.

The preparation of bicyclic derivatives having the empirical formulae $C_6H_9NO_2$ and $C_7H_{11}NO_2$ is described in particular in the journal J. Org. Chem., Vol. 45, No. 26, 1980, pages 5325-5326.

The preparation of bicyclic derivatives having the empirical formulae $C_{10}H_{18}N_2O$ and $C_7H_{12}N_2O$ is described in particular in the review Chemical Reviews, 1983, vol. 83, No. 5, pages 549 to 555.

The preparation of a compound having the empirical formula $C_{12}H_{12}N_2O$ is described in particular in the journal Angew. Chem. Int. Ed. 2000, 39, No. 3, pages 625 to 628.

No particular use of these compounds in the therapeutic field was described in these documents.

Moreover, patent application WO 2002 10172-A describes azabicyclic compounds used in the therapeutic, in particular antibacterial, field.

SUMMARY OF THE INVENTION

The subject of the invention is the compounds corresponding to the following formula (I):

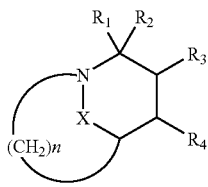

in which:
a) either R1 represents a hydrogen atom, a radical COOH, COOR, CN, $(CH_2)_{n'}$. $R_5$, $CONR_6R_7$ or

R is chosen from the group consisting of an alkyl radical containing from 1 to 6 carbon atoms, optionally substituted with one or more halogen atoms or with a pyridyl radical, a —$CH_2$-alkenyl radical containing in total from 3 to 9 carbon atoms, a (poly)alkoxyalkyl group containing 1 to 4 oxygen atoms and 3 to 10 carbon atoms, an aryl radical containing from 6 to 10 carbon atoms or an aralkyl radical containing from 7 to 11 carbon atoms, the nucleus of the aryl or aralkyl radical being optionally substituted with a radical OH, $NH_2$, $NO_2$, alkyl containing from 1 to 6 carbon atoms, alkoxy containing from 1 to 6 carbon atoms or with one or more halogen atoms, $R_5$ is chosen from the group consisting of a COOH, CN, OH, $NH_2$, CO—$NR_6R_7$, COOR or OR radical, R being as defined above, $R_6$ and $R_7$ are individually chosen from the group consisting of a hydrogen atom, an alkyl radical containing from 1 to 6 carbon atoms, an alkoxy radical containing from 1 to 6 carbon atoms, an aryl radical containing from 6 to 10 carbon atoms and an aralkyl radical containing from 7 to 11 carbon atoms and an alkyl radical containing from 1 to 6 carbon atoms which is substituted with a pyridyl radical, n' is equal to 1 or 2, $R_3$ and $R_4$ form together a phenyl or a 5- or 6-membered heterocycle with an aromatic character containing from 1 to 4 heteroatoms chosen from nitrogen, oxygen and sulfur, which is substituted with one or more groups R', R' being chosen from the group consisting of the radicals
—$(O)_a$—$(CH_2)_b$—$(O)_a$—$CONR_6R_7$, —$(O)_a$—$(CH_2)_b$—$OSO_3H$, —$(O)_a$—$(CH_2)_b$—$SO_3H$, —$(O)_a$—$SO_2R$, —$(O)_a$—$SO_2$—$CHal_3$, —$(O)_a$—$(CH_2)_b$—$NR_6R_7$, —$(O)_a$—$(CH_2)_b$—NH—COOR, —$(CH_2)_b$—COOH, —$(CH_2)_b$—COOR, —OR", OH, —$(CH_2)_b$— phenyl and —$(CH_2)_b$— 5- or 6-membered heterocycle with an aromatic character containing from 1 to 4 heteroatoms chosen from nitrogen, oxygen and sulfur, the phenyl and the heterocycle being optionally substituted with one or more halogens, alkyl containing from 1 to 6 carbon atoms, alkoxy containing from 1 to 6 carbon atoms or $CF_3$, R, $R_6$ and $R_7$ being as defined above, R" being chosen from the group consisting of alkyl radicals containing from 1 to 6 carbon atoms substituted with one or more hydroxy, protected hydroxy, oxo, halogen or cyano radicals, a being equal to 0 or 1 and b being an integer from 0 to 6, it being understood that, when R' is OH, $R_1$ represents the radical $CONR_6R_7$ in which $R_6$ or $R_7$ is an alkoxy containing from 1 to 6 carbon atoms, b) or $R_4$ represents a hydrogen atom or a group $(CH_2)_{n'_1}R_5$, $n'_1$, being equal to 0, 1 or 2 and $R_5$ being as defined above,
and $R_1$ and $R_3$ form together a substituted phenyl or heterocycle, as defined above, in both cases a) and b)
$R_2$ is chosen from the group consisting of a hydrogen atom, a halogen atom and the radicals R, $S(O)_mR$, OR, NHCOR, NHCOOR and $NHSO_2R$, R being as defined above and m being equal to 0, 1 or 2, X represents a divalent group —C(O)—B— linked to the nitrogen atom by the carbon atom, B represents a divalent group —O—$(CH_2)_{n''}$— linked to the carbonyl by the oxygen atom, a group —$NR_8$—(C$H_2)_{n''}$— or —$NR_8$—O— linked to the carbonyl by the nitrogen atom, n" is equal to 0 or 1 and $R_8$ is chosen from the group consisting of a hydrogen atom, a radical OH, R, OR, Y, OY, $Y_1$, $OY_1$, $Y_2$, $OY_2$, $Y_3$, O—$CH_2$—$CH_2$—S(O)m-R, SiRaRbRc and OSiRaRbRc, Ra, Rb and Rc individually representing a linear or branched alkyl radical containing from 1 to 6 carbon atoms or an aryl radical containing from 6 to 10 carbon atoms, and R and m being as defined above, Y is chosen from the group consisting of the radicals COH, COR, COOR, $CONH_2$, CONHR, CONHOH, CONHSO$_2$R, CH$_2$COOH, CH$_2$COOR, CHF—COOH, CHF—COOR, CF2-COOH, CF2-COOR, CN, CH$_2$CN, CH$_2$CONHOH, CH$_2$CONHCN, CH$_2$tetrazole, protected CH$_2$tetrazole, CH$_2$SO$_3$H, CH$_2$SO$_2$R, CH$_2$PO(OR)$_2$, CH$_2$PO(OR)(OH), CH$_2$PO(R)(OH) and CH$_2$PO(OH)$_2$, Y$_1$ is chosen from the group consisting of the radicals SO$_2$R, SO$_2$NHCOH, SO$_2$NHCOR, SO$_2$NHCOOR, SO$_2$NHCONHR, SO$_2$NHCONH$_2$ and SO$_3$H, Y$_2$ is chosen from the group consisting of the radicals PO(OH)$_2$, PO(OR)$_2$, PO(OH)(OR) and PO(OH)(R), Y$_3$ is chosen from the group consisting of the radicals tetrazole, tetrazole substituted with the radical R, squarate, NH or NR tetrazole, NH or NR tetrazole substituted with the radical R, NHSO$_2$R and NRSO$_2$R, CH$_2$ tetrazole and CH$_2$ tetrazole substituted with the radical R, R being as defined above, n is equal to 1 or 2.

The subject of the invention is also the salts of these compounds which may be obtained with inorganic or organic bases or acids.

DETAILED DESCRIPTION

It is clear that the compounds according to the invention are structurally distinguishable from the prior art compounds mentioned above.

The asymmetric carbon atoms contained in the compounds of formula (I) may independently of each other present the R, S or RS configuration and the subject of the invention is therefore also the compounds of formula (I) which exist in the form of pure enantiomers or pure diastereoisomers or in the form of a mixture of enantiomers, in particular racemates, or of mixtures of diastereoisomers.

It is apparent from the preceding text that the substituents R$_1$, R$_2$ or R$_4$ taken individually on the one hand and X on the other hand may be at the cis and/or trans position in relation to the ring to which they are attached and that the subject of the invention is therefore the compounds of formula (I) which exist in the form of cis isomers or of trans isomers or of mixtures.

Moreover, it is understood that the invention does not extend to compounds of formula (I) in which R' represents a group —(O)$_a$—(CH$_2$)$_b$—OSO$_3$H or —(O)$_a$—(CH$_2$)$_b$—(O)$_a$—CONR$_6$R$_7$ in which a is equal to 1 and b is equal to 0.

The expression alkyl radical containing from 1 to 6 carbon atoms is understood to mean the methyl, ethyl, propyl or isopropyl radical, and the butyl, pentyl or hexyl radical, which may be linear or branched.

The expression —CH$_2$-alkenyl radical containing from 3 to 9 carbon atoms is understood to mean for example the allyl radical, or a butenyl, pentenyl or hexenyl radical.

The expression aryl radical containing from 6 to 10 carbon atoms is understood to mean a phenyl or naphthyl radical.

The expression aralkyl radical containing from 7 to 11 carbon atoms is understood to mean a benzyl, phenethyl or methylnaphthyl radical.

The expression alkoxy radical containing from 1 to 6 carbon atoms is understood to mean in particular the methoxy, ethoxy, propoxy, isopropoxy, butoxy, isobutoxy, sec-butoxy or tert-butoxy radical.

The expression protected hydroxy radicals is understood to mean radicals protected with any groups known to persons skilled in the art, but more particularly, for dihydroxy compounds, with groups of the 1,3-dioxolanyl type.

The expression halo radical or halogen atom is understood to mean fluorine, chlorine, bromine or iodine.

In the substitutions with one or more atoms or radicals mentioned above, the term several may mean 2, 3, 4 or 5.

The expression squarate radical is understood to mean the radical of formula:

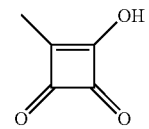

The expression heterocycle with an aromatic character is understood to mean in particular those chosen from the list which follows, the two bonds symbolizing the joining with the nitrogen-containing ring (R$_3$R$_4$ or R$_1$R$_3$):

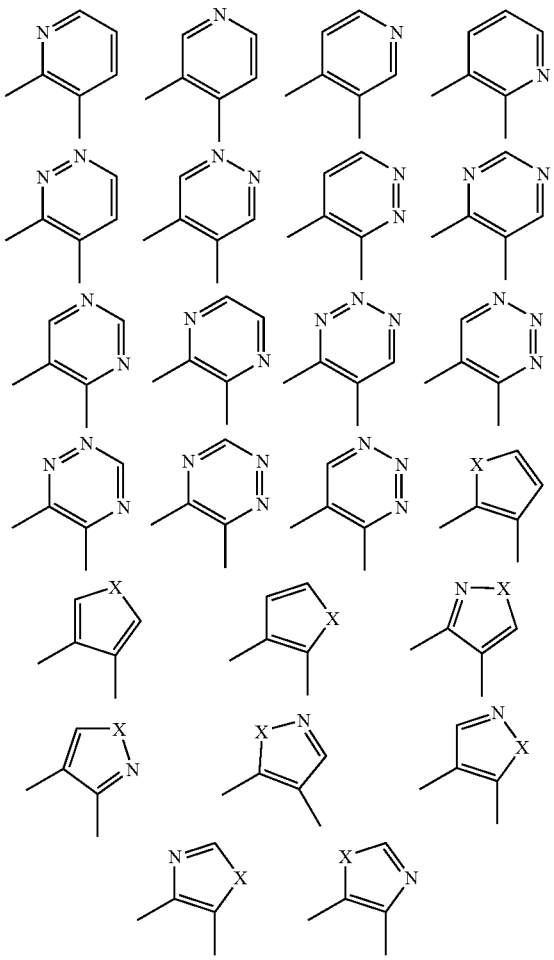

with X=NH, NR$^1$, S, O

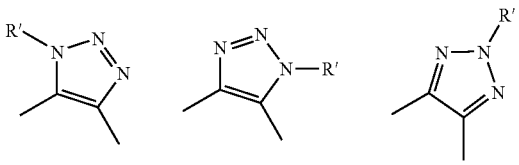

R' being as defined above.

Among the acid salts of the products of formula (I), there may be mentioned, inter alia, those formed with inorganic acids such as hydrochloric, hydrobromic, hydriodic, sulfuric or phosphoric acids, or with organic acids such as formic, acetic, trifluoroacetic, propionic, benzoic, maleic, fumaric, succinic, tartaric, citric, oxalic, glyoxylic or aspartic acids, alkanesulfonic acids such as methane- and ethanesulfonic acids, arylsulfonic acids such as benzene- and para-toluenesulfonic acids.

Among the base salts of the products of formula (I), there may be mentioned, inter alia, those formed with inorganic bases such as for example sodium, potassium, lithium, calcium, magnesium or ammonium hydroxide, or with organic bases such as for example methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine, N-methylglucamine, or else phosphonium salts such as alkylphosphonium, arylphosphoniums, alkylarylphosphonium, alkenylarylphosphonium, or quaternary ammonium salts such as tetra-n-butylammonium salt.

Among the compounds of formula (I), the subject of the invention is in particular those in which n is equal to 1 and those in which $R_2$ is a hydrogen atom.

Among these, those preferred are the compounds of formula (I) in which $R_3$ and $R_4$ form together a substituted phenyl or heterocycle as defined above. Among the latter, there may be mentioned in particular the compounds of formula (I) in which $R_3$ and $R_4$ form together a phenyl or a heterocycle chosen from the group consisting of substituted thienyl and pyrazolyl.

Among the compounds of formula (I), the subject of the invention is in particular those in which $R_1$ is chosen from the group consisting of the hydrogen atom and the groups $COOCH_3$, $COOC_2H_5$, $CONH_2$, $CONHCH_3$ and $CONHOCH_3$.

Among the compounds of formula (I), the subject of the invention is furthermore in particular those in which X represents a divalent group —CO—B— in which B represents a group —$NR_8$—$(CH_2)_{n''}$— as defined above, in which n" is equal to 0.

Among the latter, there may be mentioned in particular those in which $R_8$ is a group OY in which Y is chosen from the groups $CH_2COOH$, $CH_2COOR$, CHF—COOH, CHF—COOR, CF2—COOH, CF2—COOR, CN, $CH_2CN$, $CH_2CONHOH$, $CH_2CONHCN$, $CH_2$tetrazole, protected $CH_2$tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$ or $OY_1$, in which $Y_1$ is chosen from the groups $SO_2R$, $SO_2NHCOR$, $SO_2NHCOOR$, $SO_2NHCONHR$ and $SO_3H$, R being as defined above.

Among the compounds of formula (I), the subject of the invention is furthermore in particular those in which R' is chosen from the group consisting of —O—$CH_2$—CHOH—$CH_2OH$, —$CH_2$—$CH_2$—$NH_2$, —$CH_2$—$COOC_2H_5$, —$CH_2$—$CH_2$-phenyl, —$CH_2$-phenyl, —O—CO—NHphenyl, —O—CO—$NHC_2H_5$, —O—$SO_2$—$CF_3$, —O—($CH_2)_2$—O—$SO_3H$, —O—$(CH_2)_2$—O—$CH_3$, —$CH_2$—COOH, —O—$CH_2$-(2,2-dimethyl-1,3-dioxolan-4-yl), —CO—$NH_2$, —CO—NHphenyl, —$CH_2$—(p-$OCH_3$ phenyl) and phenyl optionally substituted with $CH_3$, $C_2H_5$, F and $CF_3$.

Among the compounds of formula (I), the subject of the invention is most particularly the compounds whose names are as follows:

the triethylammonium salt of 5,6-dihydro-6-oxo-$N^2$-phenyl-5-(sulfoxy)-4H-4,7-methanopyrazolo[3,4-e][1,3]diazepine-2,8(8H)-dicarboxamide, the sodium salt of 4,5,6,8-tetrahydro-6-oxo-5-(sulfoxy)-1H-4,7-methanopyrazolo[3,4-e][1,3]diazepine-1-carboxamide, the sodium salt of 1,4,5,8-tetrahydro-1-[(4-methoxyphenyl)methyl]-5-(sulfoxy)-6H-4,7-methanopyrazolo[3,4-e][1,3]diazepin-6-one, the sodium salt of trans-4,5,6,8-tetrahydro-2-(2-methylphenyl)-6-oxo-5-(sulfoxy)-4,7-methano-7H-thieno[2,3-e][1,3]diazepine-8-carboxamide, the sodium salt of trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide, the sodium salt of trans-2-(2-ethylphenyl)-4,5,6,8-tetrahydro-6-oxo-5-(sulfoxy)-4,7-methano-7H-thieno[2,3-e][1,3]diazepine-8-carboxamide, the sodium salt of trans-8-(2,3-dihydroxypropoxy)-1,2,3,5-tetrahydro-3-oxo-2-(sulfoxy)-1,4-methano-4H-2,4-benzodiazepine-5-carboxamide, the sodium salt of ethyl trans-3-(4-fluorophenyl)-4,6,7,8-tetrahydro-6-oxo-7-(sulfoxy)-5,8-methano-5H-thieno[2,3-e][1,3]diazepine-4-carboxylate, the sodium salt of trans-2,5,6,8-tetrahydro-6-oxo-2-phenyl-5-(sulfoxy)4H-4,7-methanopyrazolo[3,4-e][1,3]diazepine-8-carboxamide, the sodium salt of 1,4,5,8-tetrahydro-1-phenyl-5-(sulfoxy)-6H-4,7-methanopyrazolo[3,4-e][1,3]diazepin-6-one, the sodium salt of trans-4,5,6,8-tetrahydro-6-oxo-1-phenyl-5-(sulfoxy)-1H-4,7-methanopyrazolo[3,4-e][1,3]diazepine-8-carboxamide, the triethylammonium salt of methyl trans-2,5,6,8-tetrahydro-6-oxo-2-(phenylmethyl)-5-(sulfoxy)-$4_H$-4,7-methanopyrazolo[3,4-e][1,3]diazepine-8-carboxylate, the triethylammonium salt of methyl trans-4,5,6,8-tetrahydro-6-oxo-1-(2-phenylethyl)-5-(sulfoxy)-$1_H$-4,7-methanopyrazolo[3,4-e][1,3]diazepine-8-carboxylate, the triethylammonium salt of ethyl trans-4,5,6,8-tetrahydro-8-(methoxycarbonyl)-6-oxo-5-(sulfoxy)-1H-4,7-methanopyrazolo[3,4-e][1,3]diazepine-1-acetate, the triethylammonium salt of ethyl trans-5,6-dihydro-8-(methoxycarbonyl)-6-oxo-5-(sulfoxy)-4H-4,7-methanopyrazolo[3,4-e][1,3]diazepine-2(8H)-acetate, the di(triethylammonium) salt of trans-5,6-dihydro-8-(methoxycarbonyl)-6-oxo-5-sulfoxy-4H-4,7-methanopyrazolo[3,4-e][1,3]diazepine-2(8H)acetic acid, the pyridinium salt of methyl trans-1-(aminocarbonyl)-4,5,6,8-tetrahydro-6-oxo-5-(sulfoxy)-1H-4,7-methanopyrazolo[3,4-e][1,3]diazepine-8-carboxylate, the pyridinium salt of methyl trans-2-(aminocarbonyl)-2,5,6,8-tetrahydro-6-oxo-5-(sulfoxy)-4H-4,7-methanopyrazolo[3,4-e]diazepine-8-carboxylate, the sodium salt of methyl trans-2-(4-fluorophenyl)-4,5,6,8-tetrahydro-6-oxo-5-(sulfoxy)-4,7-methano-7H-thieno[2,3-e][1,3]diazepine-8-carboxylate, the sodium salt of methyl trans-2(aminocarbonyl)-4,5,6,8-tetrahydro-6-oxo-5-(sulfoxy)-4,7-methano-7H-thieno[2,3-e][1,3]diazepine-8-carboxylate, the sodium salt of ethyl trans-1,2,3,5-tetrahydro-3-oxo-9-[[(phenylamino)carbonyl]oxy]-2-(sulfoxy)-1,4-methano-4H-2,4-benzodiazepine-5-carboxylate, the sodium salt of trans-1,2,3,5-tetrahydro-N-methoxy-8-[(2-methoxyethoxy)methoxy]-3-oxo-2-(sulfoxy)-1,4-methano-4H-2,4-benzodiazepine-5-carboxamide, the sodium salt of ethyl trans-1,2,3,5-tetrahydro-3-oxo-8-[[(phenylamino)carbonyl]oxy]-2-(sulfoxy)-1,4-methano-4H-2,4-benzodiazepine-5-carboxylate, the sodium salt of ethyl trans-8-[[(ethylamino)carbonyl]oxy]-1,2,3,5-tetrahydro-3-oxo-2-(sulfoxy)-1,4-methano-4H-2,4-benzodiazepine-5-carboxylate, the sodium salt of ethyl trans-1,2,3,5-tetrahydro-3-oxo-2-(sulfoxy)-8-[[(trifluoromethyl)sulfonyl]oxy]-1,4-methano-4H-2,4-benzodiazepine-5-carboxylate, the disodium salt of trans-1,2,3,5-tetrahydro-3-oxo-2-(sulfoxy)-8-[2-(sulfoxy)ethoxy]-1,4-methano-4H-2,4-benzodiazepine-5-carboxamide, the sodium salt of trans-8-[(2,2-dimethyl-1,3-dioxolan-4-yl)methoxy]-1,2,3,5-tetrahydro-3-oxo-2-(sulfoxy)-1,4-methano-4H-2,4-benzodiazepine-5-carboxamide, the triethylammonium salt of methyl trans-2,5,6,8-tetrahydro-6-oxo-(2-phenylethyl)-5-(sulfoxy)-4H-4,7-methanopyrazolo[3,4-e][1,3]diazepine-8-carboxylate.

Another subject of the invention is a method allowing the preparation of the compounds of formula (I).

This method is characterized in that it comprises:
a) a step during which a reaction is brought about between a carbonylating agent, where appropriate in the presence of a base, and a compound of formula (II):

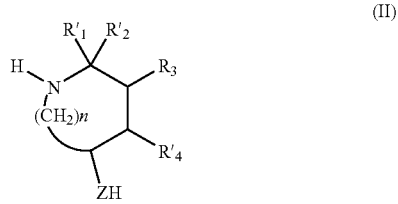

(II)

in which:
a) either $R'_1$ represents a hydrogen atom, a radical CN, protected COOH, $COOR_9$, $(CH_2)_n R'_5$, $CONR_6 R_7$,

$R_9$ is chosen from the group consisting of an alkyl radical containing from 1 to 6 carbon atoms, optionally substituted with one or more halogen atoms or with a pyridyl radical, a —$CH_2$-alkenyl radical containing in total from 3 to 9 carbon atoms, an aryl radical containing from 6 to 10 carbon atoms or an aralkyl radical containing from 7 to 11 carbon atoms, the nucleus of the aryl or aralkyl radical being optionally substituted with a radical $NO_2$, protected OH, protected $NH_2$, alkyl containing from 1 to 6 carbon atoms, alkoxy containing from 1 to 6 carbon atoms or with one or more halogen atoms, $R'_5$ is chosen from the group consisting of a radical protected OH, CN, protected $NH_2$, CO—$NR_6 R_7$, protected COOH, $COOR_9$, $OR_9$, $R_9$ being as defined above, n', $R_6$ and $R_7$ are as defined above, $R_3$ and $R'_4$ form together a phenyl or a 5- or 6-membered heterocycle with an aromatic character containing from 1 to 4 heteroatoms chosen from nitrogen, oxygen and sulfur, and optionally substituted with one or more groups $R_{10}$, $R_{10}$ being chosen from the group consisting of a hydrogen atom and the alkyl radicals containing from 1 to 6 carbon atoms substituted with one or more hydroxy, oxo, halogen or cyano radicals, or with a radical alkenyl containing from 2 to 6 carbon atoms, halo, protected OH, —OR, OR", R" being as defined above, —$(CH_2)_b$-phenyl or —$(CH_2)_b$-heterocycle with an aromatic character, which is optionally substituted, as defined above;

b) or $R'_4$ represents a hydrogen atom or a group $(CH_2)_{n'_1} R'_5$, $n'_1$ being equal to 0, 1 or 2 and $R'_5$ being as defined above, and $R'_1$ and $R_3$ form together an optionally substituted phenyl or heterocycle as defined above for $R_3$ and $R'_4$, in both cases a) and b)

$R'_2$ is chosen from the group consisting of a hydrogen atom, a halogen atom and the radicals $R_9$, $S(O)_m R_9$, $OR_9$, NHCOH, $NHCOR_9$, $NHCOOR_9$ and $NHSO_2 R_9$, m and $R_9$ being as defined above, ZH represents a group HO—$(CH_2)_{n''}$, $HNR'_8$—$(CH_2)_{n''}$— or $HNR'_8$—O—, n" is as defined above and $R'_8$ represents a hydrogen atom, a radical $R_9$, protected OH, $OR_9$, Y', OY', $Y'_1$, $OY'_1$, $Y'_2$, $OY'_2$, $Y'_3$, O—$CH_2$—$CH_2$—$S(O)_m$—R", SiRaRbRc and OSiRaRbRc, Ra, Rb and Rc individually representing a linear or branched alkyl radical containing from 1 to 6 carbon atoms or an aryl radical containing from 6 to 10 carbon atoms and $R_9$ and m being as defined above, Y' is chosen from the group consisting of the radicals COH, $COR_9$, $COOR_9$, $CONH_2$, $CONHR_9$, $CONHSO_2 R_9$, $CH_2 COOR_9$, protected $CH_2$tetrazole, $CH_2 SO_2 R_9$, $CH_2 PO(OR_9)_2$, protected CONHOH, protected $CH_2 COOH$, protected $CH_2 CONHOH$, protected $CH_2 SO_3$, protected $CH_2 PO(OR)(OH)$, protected $CH_2 PO(R)(OH)$ and protected $CH_2 PO(OH)_2$, $Y'_1$ is chosen from the group consisting of the radicals $SO_2 R_9$, $SO_2 NHCOH$, $SO_2 NHCOR_9$, $SO_2 NHCOOR_9$, $SO_2 NHCONH_2$, $SO_2 NHCONHR_9$ and protected $SO_3 H$, $Y'_2$ is chosen from the group consisting of the radicals $PO(OR_9)_2$, protected $PO(OH)_2$, protected PO(OH)(OR) and protected PO(OH)(R), $Y'_3$ is chosen from the group consisting of the radicals protected tetrazole, tetrazole substituted with the radical $R_9$, protected squarate, protected NH tetrazole, protected $NR_9$ tetrazole, protected NH, $NR_9$ tetrazole substituted with the radical $R_9$, $NHSO_2 R_9$ and $NSO_2 R_9$, $R_9$ being as defined above, and n is as defined above;

in order to obtain an intermediate compound of formula:

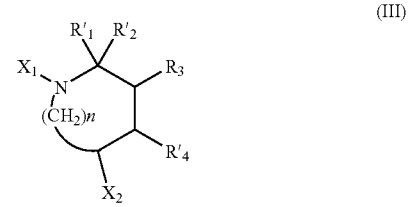

(III)

in which:

$R'_1$, $R'_2$, $R_3$, $R'_4$ and n have the same meanings as above and either $X_1$ is a hydrogen atom and $X_2$ represents a group -Z-CO—$X_3$, $X_3$ representing the residue of the carbonylating agent, or $X_2$ is a group -ZH and $X_1$ represents a group CO—$X_3$, $X_3$ being as defined above;

b) a step in which the intermediate obtained above is cyclized, in the presence of a base; and in that:

c) where appropriate, step a) is preceded and/or step b) is followed by one or more of the following reactions, in an appropriate order:

protection of the reactive functional groups;
deprotection of the reactive functional groups;
esterification;
saponification;
sulfation;
phosphatization;
amidation;
acylation;
sulfonylation;
alkylation;
formation of a urea group;
reduction of carboxylic acids;
reduction of ketones and aldehydes to alcohols;
salification;
ion exchange;
resolution or separation of diastereoisomers;
oxidation of sulfide to sulfoxide and/or sulfone;
oxidation of aldehyde to acid;
oxidation of alcohol to ketone;
halogenation or dehalogenation;
carbamoylation;
carboxylation;
introduction of an azido group;
reduction of an azido to amine;
reactions of coupling of aromatic or heteroaromatic halides or triflates or of heterocyclic nitrogens with aryl- or heteroarylboronic acids;
reactions of coupling of aromatic or heteroaromatic halides or triflates with stannyl-containing reagents;
hydrogenation of double bonds;
dihydroxylation of double bonds;
cyanidation.

As carbonylating agent, it is possible to use a reagent such as phosgene, diphosgene, triphosgene, an aryl chloroformate such as phenyl or p-nitrophenyl chloroformate, an aralkyl chloroformate such as benzyl chloroformate, alkyl or alkenyl chloroformate such as methyl or allyl chloroformate, an alkyl dicarbonate such as tert-butyl dicarbonate, carbonyldiimidazole and mixtures thereof.

The reaction preferably occurs in the presence of a base or of a mixture of bases which neutralizes the acid formed. It may be in particular an amine such as triethylamine, diisopropylethylamine, pyridine, dimethylaminopyridine. However, it is also possible to carry out the procedure using the starting material of formula II as base. An excess thereof is used in this case.

Where appropriate the product of formula II is used in the form of an acid salt, for example a hydrochloride or a trifluoroacetate.

As a base in step b), it is also possible to use amines, or else hydrides, alcoholates, amides or carbonates of alkali or alkaline-earth metals.

The amines may be chosen for example from the list above.

As hydride, it is possible to use in particular sodium or potassium hydride.

As alkali metal alcoholate, potassium t-butoxide is preferably used.

As alkali metal amide, it is possible to use in particular lithium bis(trimethylsilyl)amide.

As carbonate, it is possible to use in particular sodium or potassium carbonate or bicarbonate.

Where appropriate, the intermediate of formula III may be obtained in the form of an acid salt generated during the carbonylation reaction, and in particular a hydrochloride. It is then used in the cyclization reaction in this form.

Where appropriate, the cyclization may be performed without isolating the intermediate of formula III.

The reactions mentioned in step c) are in general conventional reactions which are well known to persons skilled in the art.

The reactive functional groups which should, where appropriate, be protected are carboxylic acid, amine, amide and hydroxy functional groups.

The protection of the acid functional group is carried out in particular in the form of alkyl esters, allyl, benzyl, benzhydryl or p-nitrobenzyl esters.

The deprotection is carried out by saponification, acid hydrolysis, hydrogenolysis, or else cleavage with the aid of soluble complexes of Palladium 0.

The protection of the amines, of the heterocyclic nitrogens and of the amides is carried out in particular, depending on the case, in the form of benzyl-containing or trityl-containing derivatives, in the form of carbamates, in particular of allyl, benzyl, phenyl or tert-butyl, or else in the form of silyl-containing derivatives such as tert-butyl dimethyl, trimethyl, triphenyl or else diphenyl tert-butyl-silyl derivatives, or phenylsulfonylalkyl or cyanoalkyl derivatives.

The deprotection is carried out, depending on the nature of the protecting group, with sodium or lithium, in liquid ammonia, by hydrogenolysis or with the aid of soluble complexes of Palladium 0, by the action of an acid, or by the action of tetrabutylammonium fluoride or of strong bases such as sodium hydride or potassium t-butoxide.

The protection of the hydroxylamines is carried out in particular in the form of benzyl or allyl ethers.

The cleavage of the ethers is carried out by hydrogenolysis or with the aid of soluble complexes of Palladium 0.

The protection of alcohols and of the phenols is carried out conventionally, in the form of ethers, esters or carbonates. The ethers may be alkyl or alkoxyalkyl ethers, preferably methyl or methoxyethoxymethyl ethers, aryl or preferably aralkyl, for example benzyl, ethers, or silyl-containing ethers, for example the silyl-containing derivatives mentioned above. The esters may be any cleavable ester known to persons skilled in the art, preferably acetate, propionate or benzoate or p-nitrobenzoate. The carbonates may be for example methyl, tert-butyl, allyl, benzyl or p-nitrobenzyl carbonates.

The deprotection is carried out by means known to persons skilled in the art, in particular saponification, hydrogenolysis, cleavage with soluble complexes of Palladium 0, hydrolysis in acid medium or else, for the silyl-containing derivatives, treatment with tetrabutylammonium fluoride.

Examples of protections and deprotections of the reactive functional groups are provided in the experimental part.

The sulfation reaction is carried out by the action of $SO_3$-amine complexes such as $SO_3$-pyridine or $SO_3$-dimethylformamide, the procedure being carried out in pyridine, it being possible for the salt formed, for example the pyridine salt, to then be exchanged for example with a salt of another amine, a quaternary ammonium or an alkali metal. Examples are provided in the experimental part.

The phosphatization reaction is carried out for example by the action of chlorophosphate such as dimethyl, dibenzyl or diphenyl chlorophosphate.

The amidation reaction is carried out starting with the carboxylic acid, with the aid of an activating agent such as an alkyl chloroformate, EDCI or BOP, by the action of aqueous ammonia or an appropriate amine or alkoxyamine or their acid salts. Examples are provided below in the experimental part.

The acylation and sulfonylation reactions are carried out in alcohols, amines or heterocyclic nitrogens, by the action, depending on the cases, of an appropriate carboxylic acid or sulfonic acid halide or anhydride, where appropriate in the presence of a base. Several examples are provided below in the experimental part.

The alkylation reaction, which, in the context, is understood in the broad sense and relates to the introduction of variously substituted alkyl groups as defined above, in particular the definition of R', is carried out by the action, on the hydroxylated derivatives, the enolates of esters or ketones, the amines or the heterocyclic nitrogens, depending on the cases, of an alkyl sulfate or an alkyl or substituted alkyl halide. Illustrations are provided below in the experimental part.

The reduction of acids to alcohols may be carried out by the action of a borane or via an intermediate mixed anhydride, by the action of an alkali metal borohydride. The mixed anhydride is prepared for example with the aid of an alkyl chloroformate. The reduction of a ketone or aldehyde to an alcohol is preferably carried out by the action of sodium borohydride. Illustrations are provided in the experimental part.

The dehydration of an amide to a nitrile may take place under carbonylation and cyclization reaction conditions.

The oxidation of sulfides to sulfoxide and/or sulfone may be carried out by the action of a peracid such as meta-chloroperbenzoic or perphthalic acid or any other reagent known to persons skilled in the art.

Salification with acids is, where appropriate, carried out by addition of an acid, in a soluble phase, to the compound. Salification with bases may involve compounds containing an acid functional group and in particular compounds containing a carboxyl functional group, those containing a sulfoxy functional group or a functional group derived from phosphoric acid or those containing a heterocycle with an acidic character.

In the case of a carboxyl functional group, the procedure is carried out by adding an appropriate base such as those mentioned above. In the case of a sulfoxy functional group or a functional group derived from phosphoric acid, the pyridinium salt is directly obtained during the action of the $SO_3$-pyridine complex and the other salts are obtained from this pyridinium salt. In either case, it is also possible to carry out the procedure by ion exchange on a resin. Examples of salifications with acids or with bases, and including a heterocycle with an acidic character, are presented below in the experimental part.

The oxidation of an aldehyde to an acid may be carried out by the action of potassium permanganate or sodium chlorite.

The oxidation of an alcohol to a ketone may be carried out by the action of pyridinium chlorochromate.

The expression halogenation is understood to mean the introduction of a halogenated substituent from a hydroxy or direct halogenation of an aromatic or heteroaromatic ring. Depending on the case, the reaction may for example be carried out by the action of iodine or in the presence of triphenylphosphine, by the action of bromine in acetic acid or else of iodine in the presence of $C_6H_5I(OCOCF_3)_2$, or else by the reaction of an electrophilic halogenated reagent such as N-fluorosulfonylimide in the presence of a strong base. Such reagents are known to persons skilled in the art and examples are presented below in the experimental part.

The dehalogenation may be carried out by hydrogenolysis.

The carbamoylation reaction may be carried out by using a chloroformate or diphosgene and then an amine or, where appropriate, ammonia, or else using an appropriate isocyanate.

The carboxylation reaction may be carried out by the action of an alkyllithium and then of carbon dioxide gas or of a chloroformate.

The introduction of an azido group may be carried out for example by the action of sodium azide on a mesylate or iodo type intermediate.

The reduction of an azide group may be carried out by the action of trialkyl- or triarylphosphine.

The reaction of couplings of aromatic halides with tin derivatives is carried out by a so-called Stille method. An illustration is given in the experimental part.

The hydrogenation of double bonds, which may be carbon-carbon or carbon-nitrogen bonds, are carried out by methods known to persons skilled in the art.

The dihydroxylation of a carbon-carbon double bond is carried out in particular by the action of osmium tetroxide.

The cleavage of the diols is preferably carried out with sodium periodate.

The introduction of a cyano is carried out by nucleophilic substitution with the aid of an alkali metal cyanide.

Illustrations of these reactions are presented below in the experimental part.

The separation of the enantiomers and diastereoisomers may be carried out according to techniques known to persons skilled in the art, in particular chromatography.

In addition to using the methods described above, compounds of formula (I) may of course be obtained by methods which start with a compound of formula (II) in which $R'_1$, $R'_2$, $R_3$, $R'_4$ and ZH have the values which lead directly (without conversion) to those of the compounds which it is desired to prepare. Where appropriate, those of these values which might contain reactive functional groups as mentioned above are then protected, the deprotection taking place after the cyclization step b or at any other appropriate time during the synthesis. The protections and deprotections are then carried out as described above.

Such methods are provided below in the experimental part.

The subject of the invention is also a method according to the preceding text, according to which the compound of formula (II) in which ZH represents a group HO—$(CH_2)_{n''}$— or $HNR'_8$—$(CH_2)_{n''}$— in which n" is equal to 0, or a group $HNR'_8$—O— is obtained by a method characterized in that a compound of formula (IV):

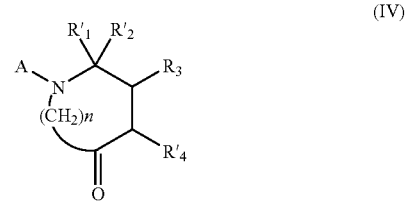

(IV)

in which $R'_1$, $R'_2$ and n are as defined above, $R_3$ and $R'_4$ have the values defined above or else values which are precursors of the values defined above and A represents a hydrogen atom or a group protecting the nitrogen, is treated with a reducing agent, in order to obtain a compound of formula (V):

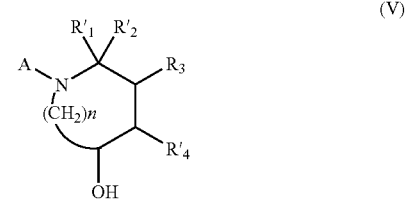

(V)

in which A, $R'_1$, $R'_2$, $R_3$, $R'_4$ and n retain their abovementioned meaning, in which, where appropriate, the OH group is replaced with a leaving group, in order to obtain a compound of formula (VI):

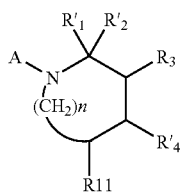

(VI)

in which A, R'$_1$, R$_3$, R'$_4$ and n retain their abovementioned meaning and R$_{11}$ represents a leaving group, which is then treated with a compound of formula Z$_1$H$_2$ in which Z$_1$ represents a divalent group —NR'$_8$— or —ONR'$_8$—, R'$_8$ retaining the abovementioned meaning, in order to obtain a compound of formula (VIII) or (VIII'):

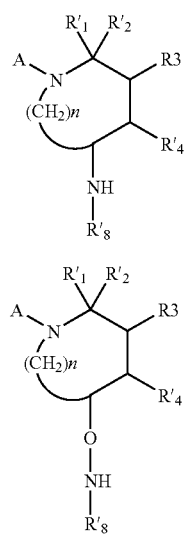

(VIII)

(VIII')

in which A, R'1, R'2, R3, R'4, n" and R'8 are as defined above, and then, where appropriate, with an appropriate agent for deprotecting the nitrogen atom, and in that, where appropriate, the intermediate of formula (IV), (V), (VIII) or (VIII') is subjected to one or more of the reactions described in step c) of the method described above, in an appropriate order.

The subject of the invention is also a method according to the preceding text, according to which the compound of formula (II) in which ZH represents a group NHR'$_8$—(CH$_2$)$_{n''}$— in which n" is equal to 0 is obtained by a method characterized in that a compound of formula (IV) as defined above is treated with a compound of formula H$_2$NR'$_8$, in order to obtain a compound of formula (VII):

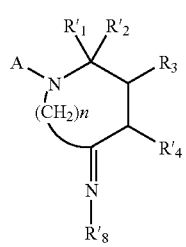

(VII)

in which A, R'$_1$, R'$_2$, n and R'$_8$ are as defined above and R$_3$ and R$_4$ have the values defined above or else values which are precursors of the values defined above, which is reacted with a reducing agent in order to obtain a compound of formula (VIII):

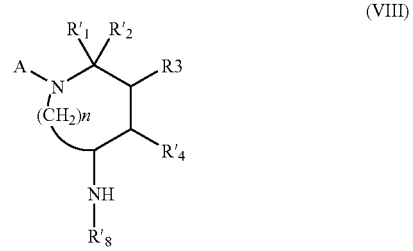

(VIII)

in which A, R'$_1$, R'$_2$, R$_3$, R'$_4$, n" and R'$_8$ are as defined above, which is treated, where appropriate, with an appropriate agent for deprotecting the nitrogen atom, and in that, where appropriate, the intermediate of formula (VII) or (VIII) is subjected to one or more of the reactions described in step c) of the method described above, in an appropriate order.

The compounds of formula (II) in which ZH represents a group HO—(CH$_2$)$_{n''}$ in which n" is equal to 1 may be obtained according to the methods described for example by S. Shiotani et al. Chem. Pharm. Bull. 15(1)88-93 (1967) (compound "IV" p. 89) or else by N. Itoh. Chem. Pharm. Bull 16 (3)455-470 (1968) (compound "XVIII" p. 461) using an appropriate starting compound. The compounds of formula (II) in which ZH represents a group NHR'$_8$—(CH$_2$)$_{n''}$ in which n" is equal to 1 may be obtained from the above compounds by a method which is identical to that described above for the preparation of the compounds in which n"=0.

The group protecting the nitrogen is in particular one of those which are mentioned above.

The reducing agent is in particular an alkali metal borohydride.

The leaving group is in particular a phosphate or a sulfonate, for example a mesylate or a tosylate, obtained by the action of a corresponding sulfonyl chloride in the presence of a base, or a halogen, more particularly a chlorine, a bromine or an iodine, obtained for example by the action of thionyl chloride or of P(C$_6$H$_5$)$_3$CBr$_4$ or PBr$_3$ or, in the case of an iodine atom, by the action of an alkali metal iodide on a sulfonate.

The deprotecting agent is in particular one of those mentioned above.

The reducing agent which is reacted on the compound of formula (VII) is in particular a sodium cyano- or acetoxyborohydride.

For practical reasons or for reasons linked to the nature of the reactions involved, it may be necessary or desirable to carry out on the intermediates of formula (IV), (V) or (VII) one or more of the reactions described in step c) of the method defined above. It is understood that these reactions are carried out under the conditions which are defined above.

The products of general formula (I) possess a very good antibiotic activity on Gram (+) bacteria such as staphylococci or streptococci. Their efficacy on Gram (−) bacteria, in particular on enterobacteria, is particularly notable.

These properties make said products and their pharmaceutically acceptable acid and base salts suitable for use as medicaments in the treatment of conditions caused by sensitive microbes and in particular in that of staphylococcia, such as staphylococcal septicemia, facial or cutaneous malignant staphylococcia, pyoderma, septic or suppurant wounds, anthrax, phlegmons, erysipelas, post-influenzal or acute primitive staphylococcia, broncho-pneumonia, or pulmonary suppurations.

These products may also be used as medicaments in the treatment of colibacillosis and related infections, proteus, klebsiella and salmonella infections and in other conditions caused by Gram (–) bacteria.

The compounds of general formula (I) are moreover endowed with beta-lactamase inhibiting properties, and are therefore of interest in controlling infectious diseases or in their prevention, in the form of a combination with various β-lactam type antibiotic compounds, in order to enhance their efficacy in controlling β-lactamase producing pathogenic bacteria.

It is well known that the enzymatic inactivation of β-lactam type antibiotics, whether penicillin or cephalosporin type compounds, in the treatment of bacterial infections is an obstacle for this type of compounds. This inactivation consists in a process of degradation of the β-lactams and constitutes one of the mechanisms for which bacteria can become resistant to treatments. It is therefore desirable to be able to counter this enzymatic process by combining with the β-lactam type antibacterial agent an agent capable of inhibiting the enzyme. When a β-lactamase inhibitor is used in combination with a β-lactam type antibiotic, it can therefore enhance its efficacy against certain microorganisms.

The subject of the present invention is therefore also, as medicaments and in particular as medicaments intended for the treatment of bacterial infections in humans or animals, and as medicaments intended for inhibiting the production of β-lactamases by pathogenic bacteria, the compounds of formula (I) as defined above and their salts with pharmaceutically acceptable acids and bases.

The subject of the invention is more particularly, as medicaments, the products of formula (I) as described above in which n is equal to 1 and those in which $R_2$ is a hydrogen atom.

The subject of the invention is most particularly, as medicaments, the products of formula (I) in which $R_3$ and $R_4$ form together a substituted phenyl or heterocycle as defined above, and in particular a phenyl or a heterocycle chosen from the group consisting of substituted thienyl and pyrazolyl.

Among the latter, there may be mentioned in particular those in which $R_1$ is chosen from the group consisting of the hydrogen atom and the groups $COOCH_3$, $COOC_2H_5$, $CONH_2$, $CONHCH_3$ and $CONHOCH_3$.

Among the compounds of formula (I), the subject of the invention is in particular, as medicaments, the products of formula (I) in which X represents a divalent group —CO—B in which B represents a group —$NR_8$—$(CH_2)_{n''}$— as defined above, in which n" is equal to 0.

Among the latter, there may be mentioned in particular those in which $R_8$ is a group OY in which Y is chosen from the groups $CH_2COOH$, $CH_2COOR$, CHF—COOH, CHF—COOR, CF2—COOH, CF2—COOR, $CH_2CONHOH$, $CH_2CONHCN$, $CH_2$ tetrazole, protected $CH_2$ tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$ or $OY_1$, in which $Y_1$ is chosen from the groups $SO_2R$, $SO_2NHCOR$, $SO_2NHCOOR$, $SO_2NHCONHR$ and $SO_3H$, R being as defined above, and those in which R' is chosen from the group consisting of —O—$CH_2$—CHOH—$CH_2OH$, —$CH_2$—$CH_2NH_2$, —CO—$NH_2$, —CO—NHphenyl, —$CH_2$— (pOCH$_3$-phenyl) and phenyl optionally substituted with $CH_3$, $C_2H_5$, F and $CF_3$.

Among the compounds of formula (I), the subject of the invention is most particularly, as medicaments, the compounds whose names are as follows:

the triethylammonium salt of 5,6-dihydro-6-oxo-$N^2$-phenyl-5(sulfoxy)-4H-4,7-methanopyrazolo[3,4-e][1,3]diazepine-2,8(8H)-dicarboxamide, the sodium salt of 4,5,6,8-tetrahydro-6-oxo-5-(sulfoxy)-1H-4,7-methanopyrazolo[3,4-e][1,3]diazepine-1-carboxamide, the sodium salt of 1,4,5,8-tetrahydro-1-[(4-methoxyphenyl)methyl]-5-(sulfoxy)-6H-4,7-methanopyrazolo[3,4-e][1,3]diazepin-6-one, the sodium salt of trans-4,5,6,8-tetrahydro-2-(2-methylphenyl)-6-oxo-5-(sulfoxy)-4,7-methano-7H-thieno[2,3-e][1,3]diazepine-8-carboxamide, the sodium salt of trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide, the sodium salt of trans-2-(2-ethylphenyl)-4,5,6,8-tetrahydro-6-oxo-5-(sulfoxy)-4,7-methano-7H-thieno[2,3-e][1,3]diazepine-8-carboxamide, the sodium salt of trans-8-(2,3-dihydroxypropoxy)-1,2,3,5-tetrahydro-3-oxo-2-(sulfoxy)-1,4-methano-4H-2,4-benzodiazepine-5-carboxamide, the sodium salt of ethyl trans-3-(4-fluorophenyl)-4,6,7,8-tetrahydro-6-oxo-7-(sulfoxy)-5,8-methano-5H-thieno [2,3-e][1,3]diazepine-4-carboxylate, the sodium salt of trans-2,5,6,8-tetrahydro-6-oxo-2-phenyl-5-(sulfoxy)-4H-4,7-methanopyrazolo[3,4-e][1,3]diazepine-8-carboxamide, the sodium salt of 1,4,5,8-tetrahydro-1-phenyl-5-(sulfoxy)-6H-4,7-methanopyrazolo[3,4-e][1,3]diazepin-6-one, the sodium salt of trans-4,5,6,8-tetrahydro-6-oxo-1-phenyl-5 (sulfoxy)-1H-4,7-methanopyrazolo[3,4-e][1,3]diazepine-8-carboxamide, the triethylammonium salt of methyl trans-2,5,6,8-tetrahydro-6-oxo-2-(phenylmethyl)-5-(sulfoxy)-4$_H$-4,7-methanopyrazolo[3,4-e][1,3]diazepine-8-carboxylate, the triethylammonium salt of methyl trans-4,5,6,8-tetrahydro-6-oxo-1-(2-phenylethyl)-5-(sulfoxy)-1$_H$-4,7-methanopyrazolo[3,4-e][1,3]diazepine-8-carboxylate, the triethylammonium salt of ethyl trans-4,5,6,8-tetrahydro-8-(methoxycarbonyl)-6-oxo-5-(sulfoxy)-1H-4,7-methanopyrazolo[3,4-e][1,3]diazepine-1-acetate, the triethylammonium salt of ethyl trans-5,6-dihydro-8-(methoxycarbonyl)-6-oxo-5-(sulfoxy)-4H-4,7-methanopyrazolo[3,4-e][1,3]diazepine-2(8H)-acetate, the di(triethylammonium) salt of trans-5,6-dihydro-8-(methoxycarbonyl)-6-oxo-5-sulfoxy-4H-4,7-methanopyrazolo[3,4-e][1,3]diazepine-2(8H)acetic acid, the pyridinium salt of methyl trans-1-(aminocarbonyl)-4,5,6,8-tetrahydro-6-oxo-5-(sulfoxy)-1H-4,7-methanopyrazolo[3,4-e][1,3]diazepine-8-carboxylate, the pyridinium salt of methyl trans-2-(aminocarbonyl)-2,5,6,8-tetrahydro-6-oxo-5-(sulfoxy)-4H-4,7-methanopyrazolo[3,4-e][diazepine-8-carboxylate, the sodium salt of methyl trans-2-(4-fluorophenyl)-4,5,6,8-tetrahydro-6-oxo-5-(sulfoxy)-4,7-methano-7H-thieno[2,3-e][1,3]diazepine-8-carboxylate, the sodium salt of methyl trans-2(aminocarbonyl)-4,5,6,8-tetrahydro-6-oxo-5-(sulfoxy)-4,7-methano-7H-thieno[2,3-e][1,3]diazepine-8-carboxylate, the sodium salt of ethyl trans-1,2,3,5-tetrahydro-3-oxo-9-[[(phenylamino)carbonyl]oxy]-2-(sulfoxy)-1,4-methano-4H-2,4-benzodiazepine-5-carboxylate, the sodium salt of trans-1,2,3,5-tetrahydro-N-methoxy-8-[(2-methoxyethoxy)methoxy]-3-oxo-2-(sulfoxy)-1,4-methano-4H-2,4-benzodiazepine-5-carboxamide, the sodium salt of ethyl trans-1,2,3,5-tetrahydro-3-oxo-8-[[(phenylamino)carbonyl]oxy]-2-(sulfoxy)-1,4-methano-4H-2,4-benzodiazepine-5-carboxylate, the sodium salt of ethyl trans-8-[[(ethylamino)carbonyl]oxy]-1,2,3,5-tetrahydro-3-oxo-2-(sulfoxy)-1,4-methano-4H-2,4-benzodiazepine-5-carboxylate, the sodium salt of ethyl trans-1,2,3,5-tetrahydro-3-oxo-2-(sulfoxy)-8-[[(trifluoromethyl)sulfonyl]oxy]-1,4-methano-4H-2,4-benzodiazepine-5-carboxylate, the disodium salt of trans-1,2,3,5-tetrahydro-3-oxo-2-(sulfoxy)-8-[2-(sulfoxy)ethoxy]-1,4-methano-4H-2,4-benzodiazepine-5-carboxamide, the sodium salt of trans-8-[(2,2-dimethyl-1,3-dioxolan-4-yl)methoxy]-1,2,3,5-tetrahydro-3-oxo-2-(sulfoxy)-1,4-methano-4H-2,4-benzodiazepine-5-carboxamide, the triethylammonium salt of methyl trans-2,5,6,8-tetrahydro-6-oxo-2-(2-phenylethyl)-5-(sulfoxy)-4H-4,7-methanopyrazolo[3,4-e][1,3]diazepine-8-carboxylate.

The β-lactam type antibiotic with which it is possible to combine the compound of formula (I) may be chosen from the group consisting of penams, penems, carbapenems, cephems, carbacephems, oxacephems, cephamycins and monobactams.

The expression β-lactams is understood to mean for example penicillins such as amoxicillin, ampicillin, azlocillin, mezlocillin, apalcillin, hetacillin, bacampicillin, carbenicillin, sulbenicillin, ticarcillin, piperacillin, azlocillin, mecillinam, pivmecillinam, methicillin, ciclacillin, talampicillin, aspoxicillin, oxacillin, cloxacillin, dicloxacillin, flucloxacillin, nafcillin or pivampicillin, cephalosporins such as cephalothin, cephaloridin, cefaclor, cefadroxil, cefamandole, cefazolin, cephalexin, cephradine, ceftizoxime, cefoxitin, cephacetril, cefotiam, cefotaxime, cefsulodin, cefoperazone, ceftizoxime, cefmenoxime, cefinetazole, cephaloglycin, cefonicid, cefodizime, cefpirome, ceftazidime, ceftriaxone, cefpiramide, cefbuperazone, cefozopran, cefepim, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, latamoxef, carbapenems such as imipenem, meropenem, biapenem or panipenem and monobactams such as aztreonam and carumonam, and their salts.

The compounds of formula (I) or their pharmaceutically acceptable salts may be administered at the same time as the dose of β-lactam type antibiotics or separately, preferably after the latter. This may be carried out in the form of a mixture of the two active ingredients or in the form of a pharmaceutical combination of the two separate active ingredients.

The dosage of the compounds of the formula (I) and of their pharmaceutically acceptable salts may of course vary within wide limits and should naturally be adjusted, in each particular case, to the individual conditions and to the pathogenic agent to be controlled. In general, for a use in the treatment of bacterial infections, the daily dose may be between 0.250 g and 10 g per day, by the oral route in humans, with the product described in Example 24 or 45 or else between 0.25 g and 10 g per day by the intramuscular or intravenous route. For a use as a β-lactamase inhibitor, a daily dose in humans which may range from 0.1 to about 10 g may be suitable.

Moreover, the ratio of the β-lactamase inhibitor of formula (I) or of the pharmaceutically acceptable salt thereof to the β-lactam type antibiotic may also vary within wide limits and should be adjusted, in each particular case, to the individual conditions. In general, a ratio ranging from about 1:20 to about 1:1 should be recommended.

The antibiotic or β-lactamase inhibitor medicaments as defined above are used in the form of pharmaceutical compositions in the form of a mixture with an inert, organic or inorganic pharmaceutical excipient suitable for the desired mode of administration, and the subject of the invention is also the pharmaceutical compositions containing, as active ingredient, at least one of the compounds of the invention defined above and the compositions containing, as active ingredient, at least one of the compounds of the invention as defined above and at least one β-lactam type medicament.

These compositions may be administered orally, rectally, parenterally, in particular intramuscularly, or locally as a topical application to the skin and the mucous membranes.

The compositions according to the invention may be solid or liquid and may be provided in the dosage forms commonly used in human medicine, such as for example simple or sugar-coated tablets, gelatine capsules, granules, suppositories, preparations for injection, ointments, creams, gels; they are prepared according to the customary methods. The active ingredient(s) may be incorporated into excipients normally used in these pharmaceutical compositions, such as talc, gum arabic, lactose, starch, magnesium stearate, cocoa butter, aqueous or nonaqueous vehicles, fatty substances of animal or plant origin, paraffin derivatives, glycols, various wetting, dispersing or emulsifying agents, preservatives.

These compositions may be provided in particular in the form of a lyophilisate indended to be dissolved immediately before use in an appropriate vehicle, for example apyrogenic sterile water.

The dose administered is variable depending on the condition to be treated, the subject in question, the route of administration and the product considered. It may be for example between 0.250 g and 10 g per day, orally in humans, with the product described in Example 1 or alternatively between 0.25 g and 10 g per day intramuscularly or intravenously.

The products of formula (I) may also be used as disinfectants for surgical instruments.

The subject of the invention is finally, as novel industrial products and in particular as intermediate products necessary for the preparation of the products of formula (I):

the products of formula (III) as defined above in which $R_3$ and $R'_4$ or $R'_1$ and $R_3$ form together a phenyl or a heterocycle with an aromatic character, which is substituted with a radical —$(CH_2)_b$-phenyl or —$(CH_2)_b$-heterocycle with an aromatic character, which is optionally substituted, as defined above, and their salts with acids and in particular their hydrochlorides and trifluoroacetates;

the products of formula (III) as defined above, in which $R'_1$ represents a radical $CONR_6R_7$ in which $R_6$ or $R_7$ represents an alkoxy radical containing from 1 to 6 carbon atoms, all the other values being as defined in formula III, and their salts with acids and in particular their hydrochlorides and trifluoroacetates;

the products of formula (II) as defined above, in which $R_3$ and $R'_4$ or $R'_1$ and $R_3$ form together form together a phenyl or a heterocycle with an aromatic character, which is substituted with a radical —$(CH_2)_3$-phenyl or —$(CH_2)_b$— heterocycle with an aromatic character, which is optionally substituted, as defined above, and their salts with acids and in particular their hydrochlorides and trifluoroacetates;

the products of formula (II) as defined above, in which $R'_1$ represents a radical $CONR_6R_7$ in which $R_6$ or $R_7$ represents an alkoxy radical containing from 1 to 6 carbon atoms, all the other values being as defined in formula III, and their salts with acids and in particular their hydrochlorides and trifluoroacetates;

the products of formulae (IV), (V), (VI), (VII), (VIII) and (VIII') as defined above, in which $R_3$ and $R'_4$ or $R'_1$ and $R_3$ represents a radical —$(CH_2)_3$-phenyl or —$(CH_2)_b$-heterocycle with an aromatic character, which is optionally substituted, as defined above, and their salts with an acid and optionally their hydrochlorides and trifluoroacetates;

the products of formulae (IV), (V), (VI), (VII), (VIII) and (VIII') as defined above, in which $R'_1$ represents a radical $CONR_6R_7$ in which $R_6$ or $R_7$ represents an alkoxy radical containing from 1 to 6 carbon atoms, all the other values being as defined in formulae (IV), (V), (VI), (VII), (VIII) and (VIII'), and their salts with an acid and in particular their chlorohydrides and trifluoroacetates.

The products of formula (IV) can be prepared for example according to methods provided below in the experimental part.

The following examples illustrate the invention without however limiting the scope thereof.

EXAMPLES

In the preceding description and in the examples which follow, the following abbreviations have been used:
DEAD: diethyl azodicarboxylate
TEA: triethylamine
DMAP: 4-dimethylaminopyridine
EDCI: 1-(3-dimethylaminopropyl)-3-ethylcarbodiimide hydrochloride
THF: tetrahydrofuran
AcOEt: ethyl acetate
DMF: N,N-dimethylformamide
AIBN: 2,2'-azobisisobutyronitrile
M: molecular molar mass
MS: mass spectrometry
EI: electron impact
SIMS: secondary ion mass spectrometry
FAB: fast atom bombardment
BOP: benzotriazol-1-yloxytripyrolidino-phosphonium hexafluorophosphate
HOBt: 1-hydroxybenzotriazole hydrate
DBU: diazabicycloundecene
$(BOC)_2O$: t-butyl dicarbonate
$NaBH_3CN$: sodium cyanoborohydride
DMSO: dimethyl sulfoxide
DIEA: diisopropylethyldiamine
MEMCl: 2-methoxyethoxymethyl chloride
TMSCN: trimethylsilyl cyanide
BOC-ON: 2-(tert-butoxycarbonyloxyimino)-2-phenylacetonitrile

Example 1

Methyl trans-4,5,6,8-tetrahydro-6-oxo-5-(phenyl-methoxy)-1H-4,7-methanopyrazolo[3,4-e][1,3]diazepine-8-carboxylate Stage A1:
Preparation of [2-(phenylthio)ethyl]hydrazine.
Step 1
100 g of 2-bromoethylphenyl sulfide dissolved in 1 l of ethanol are introduced into a round-bottomed flask placed under a nitrogen atmosphere, and 184.2 g of hydrazine hydrate are added. The medium is heated at 100° C. overnight. Once the reaction is complete, the solvent is then distilled off under reduced pressure at 80° C.-90° C. 65 g of potassium carbonate and 1 l of methylene chloride are then added to the medium. The medium is stirred for 15 minutes, the organic phase is then extracted with 2×500 ml of water, the organic phase is then dried over magnesium sulfate, filtered and evaporated under reduced pressure. The residue is next taken up in 750 ml of an ethanol/water mixture to which 12 ml of concentrated sulfuric acid are added dropwise. The product crystallizes and the precipitate is filtered and then rinsed with an ethanol/water, 80/20, solution and then with ether. The product is then dried under reduced pressure.

81.84 g of [2-(phenylthio)ethyl]hydrazine hemisulfate salt having the empirical formula $C_8H_{12}N_2S+½$ of $H_2SO_4$ are obtained. (M=217.3 g).

The yield obtained is 81%.

Step 2

79.7 g of the product obtained in the preceding step 1 are dissolved in 1.9 l of dichloromethane. 400 ml of 1 N sodium hydroxide are then added, and the medium is vigorously stirred. The organic phase is next extracted with dichloromethane, the organic phase is then dried over $MgSO_4$ and evaporated off under reduced pressure.

[2-(Phenylthio)ethyl]hydrazine having the empirical formula $C_8H_{12}N_2S$ is obtained with a quantitative yield (M=168.26 g).

The yield obtained is 89%.

Stage A2

56.0 g (of 1,1-dimethylethyl 3,5-dioxo-1-piperidinecarboxylate having the empirical formula $C_{10}H_{15}NO_4$ (prepared by a method similar to that described in Heterocycles, 22, 2769-2773, (1984), replacing methyl chloroformate with $(BOC)_2$O, are prepared as a suspension. 55.5 ml of N,N-dimethylformamide dimethyl acetal at 95% are added at room temperature. The medium is stirred for half an hour at 80° C. and then for 3 hours at 50° C. The solvent is evaporated off under reduced pressure. 79 g of 1,1-dimethylethyl 4-[(dimethylamino)methylene]-3,5-dioxo-1-piperidinecarboxylate having the empirical formula $C_{13}H_{20}N_2O_4$ are thus obtained.

The corresponding yield is 99%.

Stage B 79 g of the product obtained in stage A2 are dissolved in 1 liter of absolute methanol, and then 54.5 g of [2-(phenylthio)ethyl]hydrazine are added. The medium is stirred for 3 hours 30 minutes at room temperature. The solvent is evaporated off under reduced pressure and the medium is purified by chromatography on silica eluting with a dichloromethane/AcOEt 1/1 mixture.

The compound 1,1-dimethylethyl 1,4,5,7-tetrahydro-4-oxo-1-[2-(phenylthio)ethyl]-6H-pyrazolo[3,4-c]pyridine-6-carboxylate having the empirical formula $C_{19}H_{23}N_3O_3S$ is obtained (M=373.48 g).

The corresponding yield obtained is 57.6%.

Stage C 74.5 g of the ketone obtained in the preceding stage B are dissolved in 372.5 ml of methanol, in a round-bottomed flask placed under a nitrogen atmosphere, the medium is then cooled with an ice bath and 7.58 g of sodium borohydride are introduced in small fractions over 20 minutes.

The medium is allowed to return to room temperature over two hours, and then dichloromethane and an aqueous tartaric acid solution at 10% are successively added. The medium is vigorously stirred and then separated by decantation and reextracted with dichloromethane. The organic phases are combined and they are dried over magnesium sulfate, filtered and the solvent of the filtrate is separated off under reduced pressure. The residue is taken up in dichloromethane, filtered and the solvent is again evaporated off under reduced pressure.

72.5 g of the compound 1,1-dimethylethyl 1,4,5,7-tetrahydro-4-hydroxy-1-[2-(phenylthio)ethyl]-6H-pyrazolo[3,4-c]pyridine-6-carboxylate having an empirical formula $C_{19}H_{25}N_3O_3S$ are obtained (M=375.49 g).

The corresponding yield is 97%.

Stage D 75 g of the product obtained in the preceding stage C are dissolved in 1 l of dichloromethane at 0° C. 118 g of methachloroperbenzoic acid at 70% are added, and the medium is then stirred for 1 h 30 min at room temperature. 1.5 l of dichloromethane and 1.6 l of 0.5 N sodium thiosulfate are added to the reaction medium. After extraction of the organic phase, it is rewashed with 1 l of sodium thiosulfate and then with 1.5 l of $NaHCO_3$ and finally with 1.5 l of water. The aqueous phases are then again reextracted with dichloromethane and then the various organic phases are combined, dried over magnesium sulfate, filtered, and the solvent is then evaporated off under reduced pressure.

The crude product is recrystallized from isopropyl ether to give 81 g of the compound 1,1-dimethylethyl 1,4,5,7-tetrahydro-4-hydroxy-1-[2-[1-propenylsulfonyl]ethyl]-6H-pyrazolo [3,4-c]pyridine-6-carboxylate having the empirical formula $C_{19}H_{25}N_3O_5S$ (M=407.49 g).

The corresponding yield is 99%.

Stage E 57.2 g of the product obtained in the preceding stage D are dissolved in 572 ml of anhydrous THF in a round-bottomed flask placed under an inert atmosphere and at a temperature of −30° C. 337 ml of a 1 M potassium tert-butoxide solution in THF are then added. The medium is stirred for 1 hour and then 20 ml of acetic acid are added to the reaction medium. An aqueous bicarbonate solution of $NaHCO_3$ and NaCl is then added, and the organic phase is then extracted several times with ethyl acetate. The organic phases are dried over magnesium sulfate, filtered and the solvent evaporated under reduced pressure. 57.4 g of crude product are recovered, which product is then purified on silica, eluting with a dichloromethane/acetone, 4/6, mixture.

38.6 g of 1,1-dimethylethyl 1,4,5,7-tetrahydro-4-hydroxy-6H-pyrazolo[3,4-c]pyridine-6-carboxylate having the empirical formula $C_{11}H_{17}N_3O_3$ are obtained after evaporation of the solvent (M=239.28 g).

The corresponding yield is 84%.

Stage F 35 g of the product obtained in the preceding stage E are dissolved in 890 ml of dichloromethane, in a round-bottomed flask placed under a nitrogen atmosphere. 49.77 g of $(Ph)_3$CCl are added and the solution is then cooled to −30° C. with a dry ice/acetone mixture. 24.7 ml of triethylamine are then added, and the reaction medium is stirred, while allowing the temperature to return to room temperature over 4 h 30 min. After evaporation of the solvent under reduced pressure, the residue is then poured into 1.6 l of ethyl acetate and the medium is washed with 1.8 l of water. The organic phase is then dried over magnesium sulfate, filtered, and the solvent evaporated off under reduced pressure. The residue is taken up in ethyl ether and the precipitate obtained is washed in pentane. After drying, 62.5 g of 1,1-dimethylethyl 2,4,5,7-tetrahydro-4-hydroxy-2-(triphenylmethyl)-6H-pyrazolo[3,4-c]pyridine-6-carboxylate having the empirical formula $C_{30}H_{31}N_3O_3$ are obtained (M=481.60 g).

The yield is 99%.

Stage G 26.6 g of the alcohol obtained in the preceding stage F are dissolved in 230 ml of THF, in a round-bottomed flask placed under a nitrogen atmosphere, the medium is then cooled to −78° C. and 81 ml of tert-butyllithium are introduced as a 1.7 M solution in pentane. The reaction is allowed to proceed for 15 minutes at −78° C., and carbon dioxide gas is introduced in excess over 10 minutes, and then the temperature is allowed to return to room temperature.

The reaction mixture is hydrolyzed by adding 100 ml of water and 300 ml of ethyl acetate and then acidified to pH=4 by addition of formic acid. The aqueous phase is extracted several times with ethyl acetate and then the organic phase is dried over $MgSO_4$, filtered and the solvent evaporated under reduced pressure to give 29.8 g of crude product. The latter is dissolved in 300 ml of ether and then extracted with 3×200 ml of a saturated $NaHCO_3$ solution. The aqueous phase is acidified to pH=4 by addition of formic acid and then extracted with ethyl acetate. After drying over MgSO4, filtration and evaporation under reduced pressure, 14.8 g of acid having the empirical formula $C_{31}H_{31}N_3O_5$ (M=525.61 g) are obtained.

The 14.8 g of the compound obtained are then esterified in the presence of 3.7 g of $K_2CO_3$ and 4.9 ml of dimethyl sulfate. The medium is stirred for 1 hour at room temperature and then 7.4 ml of triethylamine are added. After 40 minutes, 300 ml of ethyl acetate and 200 ml of water are added. After stirring, the medium is separated by decantation and the aqueous phase then reextracted with ethyl acetate. The organic phases are washed with a solution of water saturated with NaCl. The organic phases are then dried over magnesium sulfate and the solvent is evaporated under reduced pressure.

11.23 g of 6-(1,1-dimethylethyl) and 7-methyl 2,4,5,7-tetrahydro-4-hydroxy-2-(triphenylmethyl)-6H-pyrazolo[3,4-c]pyridine-6,7-dicarboxylate having the empirical formula $C_{32}H_{33}N_3O_5$ are obtained (M=739.64 g).

The corresponding yield over the two steps is 42%.

Stage H 1 g of the product obtained in the preceding stage G is solubilized in 50 ml of dichloromethane in a round-bottomed flask under an argon atmosphere. 2.8 g of triethylamine are added followed by 4.8 g of dilute $(CH_3SO_2)_2O$ in 1 ml of dichloromethane. The medium is stirred for one hour at −70° C. and then 0.68 g of O-benzylhydroxylamine is added. The medium is again stirred for 10 minutes at −78° C., for 1 h 20 min at −50° C. and finally at 0° C. overnight. The medium is left for a further one hour at 20° C., and then dichloromethane is added and the organic phase is washed with a tartaric acid solution and then an aqueous NaCl solution and finally pure water. The organic phase is dried over $MgSO_4$, filtered and the solvent is evaporated off under reduced pressure. 11.9 g of product are obtained, which product is purified on silica, eluting with a petroleum ether/ethyl acetate, 8/2, mixture.

8.9 g of 6-(1,1-dimethylethyl) and 7-methyl 2,4,5,7-tetrahydro-4-[(phenylmethoxy)amino]-2-(triphenylmethyl)-6H-pyrazolo[3,4-c]pyridine-6,7-dicarboxylate having the empirical formula $C_{39}H_{40}N_4O_5$ are obtained (M=644.78 g).

The corresponding yield is 75%.

Stage I 10 g of the product obtained in the preceding stage H are dissolved in 70 ml of ethyl acetate, in a round-bottomed flask kept at 0° C. 35 ml of a saturated hydrochloric acid solution in ethyl acetate are added and then the medium is stirred for 3 hours. After evaporation of the solvent, crude methyl 4,5,6,7-tetrahydro-4-[(phenylmethoxy)amino]-2H-pyrazolo[3,4-c]pyridine-7-carboxylate dihydrochloride is obtained.

Stage J

The crude product obtained in stage I is taken up in water. The aqueous phase is then washed with ethyl acetate. The aqueous phase is next brought to pH=10 with a solution of aqueous ammonia at 20% and then extracted three times with ethyl acetate. After drying over magnesium sulfate, filtration, and evaporation of the solvent under reduced pressure, 4.21 g of methyl 4,5,6,7-tetrahydro-4-[(phenylmethoxy)amino]-2H-pyrazolo[3,4-c]pyridine-7-carboxylate having the empirical formula $C_{15}H_{18}N_4O_3$ are obtained (M=302.34 g).

The corresponding yield in both steps I and J is 89.7%.

Stage K 9.24 g of the product obtained in the preceding stage I, 3 liters of acetonitrile and 12.3 ml of TEA are introduced into a round-bottomed flask placed under an argon atmosphere and cooled by an ice bath. The medium is stirred for 2 minutes and 1.85 ml of diphosgene are then introduced. The solution is stirred at 20° C. for 1 hour. The medium is diluted with AcOEt and the medium is washed with a tartaric acid solution at 10% and then with water. The organic phase is dried over magnesium sulfate and the solvent is evaporated off under reduced pressure.

The crude product is dissolved in 500 ml of dichloromethane with 0.5 ml of DBU. After 10 minutes of contact, the reaction mixture is washed with a tartaric acid solution at 10% and with water. After evaporation of the solvent under reduced pressure.

9.6 g of methyl trans-4,5,6,8-tetrahydro-6-oxo-5-(phenylmethoxy)-1H-4,7-methanopyrazolo[3,4-e][1,3]diazepine-8-carboxylate having the empirical formula $C_{16}H_{16}N_4O_4$ are obtained (M=328.33 g).

The corresponding yield is 95%.

Stage L 0.2 g of the product obtained in the preceding stage K is dissolved in 2 ml of DMF in a round-bottomed flask kept at 0° C. under a nitrogen atmosphere, and 0.115 g of benzyl bromide is added followed by 0.032 g of NaH. The medium is stirred for 10 minutes at 0° C. and then the temperature is allowed to return to room temperature. After one hour, the reaction is stopped. The reaction medium is poured into an aqueous NaCl solution and the medium is extracted twice with ethyl acetate. The organic phase is then dried over magnesium sulfate, filtered and the solvent is evaporated off under reduced pressure. 231 mg of product are obtained, which product is purified on a silica column, eluting with a methylene chloride/ethyl acetate/triaethylamine 95/0.5/0.1% mixture. After evaporation of the solvent, 70 mg of the compound methyl trans-2,5,6,8-tetrahydro-6-oxo-5-(phenylmethoxy)-2-(phenylmethyl)-4H-4,7-methanopyrazolo[3,4-e][1,3]diazepine-8-carboxylate having the empirical formula $C_{23}H_{22}N_4O_4$ are obtained (M=418.46 g).

The corresponding yield is 27%.

Stage M 65 mg of the product obtained in the preceding stage are dissolved in 1 ml of MeOH and then 29 mg of 10% palladium on carbon are added and the medium is placed under a hydrogen atmosphere, with vigorous stirring. When the starting material has been consumed, the catalyst is filtered off and the solvent is evaporated off under reduced pressure.

47 mg of the compound methyl trans-2,5,6,8-tetrahydro-5-hydroxy-6-oxo-2-(phenylmethyl)-4H-4,7-methanopyrazolo[3,4-e][1,3]diazepine-8-carboxylate having the empirical formula $C_{16}H_{16}N_4O_4$ are obtained (M=328.33 g).

Stage N 0.047 g of the product obtained in the preceding stage M is dissolved in 1 ml of pyridine containing a few crystals of a 4 Å molecular sieve. 0.068 g of the pyridine $SO_3$ complex is then added. The medium is stirred overnight at room temperature. The sieve is then filtered off and rinsed with water and then with methylene chloride. After evaporation of the solvents coevaporated with toluene, 114 mg of crude product are obtained which are purified on silica, eluting with a methylene chloride/ethanol/triethylamine 90/10/0.1% mixture. 41 mg of the compound of triethylammonium salt of methyl trans-2,5,6,8-tetrahydro-6-oxo-2-(phenylmethyl)-5-(sulfoxy)-4H-4,7-methanopyrazolo[3,4-e][1,3]diazepine-8-carboxylate having the empirical formula $C_{22}H_{31}N_5O_7S$ are obtained (M=509.58).

The yield obtained over the two stages M and N is 52%.

Proton NMR:

DMSO-$d_6$ at 300 MHz (chemical shift and multiplicity): 1.12 (broad s) $(CH_3CH_2)_3N$; 3.05 (1): $(CH_3CH_2)_3N$; 3.45 (m): N—$CH_2$—CH; 4,75 (m): —)N—$CH_2$—CH; 3.73 (s): $CH_3OOC$—CH; 4.98 (s): $CH_3OOC$—CH; 5.28 (broad s): N—$CH_2$—ϕ; 7.22 to 7.39 (m): aromatic H; 7.87 (s): N—CH.

LC/MS (negative electrospray): general conditions

Kromasil C18 column 4.6×250 mm, 5 μ oven at 30° C.

Flow rate=1 ml/min $V_{inj}$=15 μl

Detection λ=200-400 mm

MS/ESP+/−mode CV=50V

Eluent: A=$H_2O$ (0.1% $HCO_2H$)
B=$CH_3CN$

| time | Gradient: A % | B % |
|---|---|---|
| 0.00 | 80.0 | 20.0 |
| 15.00 | 50.0 | 50.0 |
| 25.00 | 20.0 | 80.0 |
| 40.00 | 80.0 | 20.0 |
| 50.00 | 80.0 | 20.0 |

LC/MS (negative electrospray) m/z: TR=9.70 min M-=407.

Example 2

Triethylammonium Salt of Methyl trans-4,5,6,8-tetrahydro-6-oxo-1-(phenylethyl)-5-(sulfoxy)-1H-4,7-methanopyrazolo[3,4-e][1,3]diazepine-8-carboxylate Stage A 0.1 g of the product obtained in stage K of Example 1 is dissolved in 0.8 ml of DMF, in a round-bottomed flask placed under a nitrogen atmosphere at 0° C. 0.062 g of 2-bromophenylethane is added followed by 0.015 g of NaH. The medium is stirred for 15 minutes at 0° C. and the reaction medium is allowed to return to room temperature. The medium is stirred for 6 hours, a saturated aqueous NaCl solution is then added and the aqueous phase is extracted several times with ethyl acetate. After drying the organic phase over magnesium sulfate, the solvent is filtered and evaporated off under reduced pressure. The crude product obtained is filtered on silica, eluting with a methylene chloride/acetone/triethylamine, 98/2/0.1%, mixture. After evaporating the solvent, 28.8 mg are obtained, that is a yield of 21.5% of the compound isomer A, methyl trans-4,5,6,8-tetrahydro-6-oxo-5-(phenylmethoxy)-1-(phenylethyl)-1H-4,7-methanopyrazolo[3,4-e][1,3]diazepine-8-carboxylate, having the empirical formula $C_{24}H_{24}N_4O_4$ (432.46 g), and 37 mg are obtained, that is a yield of 28% of isomer B, methyl trans-4,5,6,8-tetrahydro-6-oxo-5-(phenylmethoxy)-2-(2-phenylethyl)-1H-4,7-methanopyrazolo[3,4-e][1,3]diazepine-8-carboxylate having the empirical formula $C_{24}H_{24}N_4O_4$ (M=432.48 g).

Stage B 0.028 g of the isomer A obtained in the preceding stage A is dissolved in 1 ml of methanol, in a round-bottomed flask placed under a nitrogen atmosphere, and 0.0168 g of 10% palladium on carbon is then added. The medium is placed under a hydrogen atmosphere. After 2 hours, the reaction is stopped and the reaction medium is filtered and the solvent is evaporated under reduced pressure. 13.8 mg of methyl trans-4,5,6,8-tetrahydro-5-hydroxy-6-oxo-1-(phenylethyl)-1H-4,7-methanopyrazolo[3,4-e][1,3]diazepine-8-carboxylate having the empirical formula $C_{17}H_{18}N_4O_4$ are obtained (M=342.36 g).

The corresponding yield is 62%.

Stage C 0.0130 g of the product obtained in the preceding stage B is dissolved in 1 ml of pyridine, in a round-bottomed flask, and 0.018 g of pyridine-$SO_3$ complex is added. The medium is stirred overnight at room temperature and then the reaction mixture is filtered and rinsed with a methylene chloride/water mixture. After evaporation, 19 mg of crude product are obtained which are purified by chromatography on silica, eluting with a methylene chloride/ethanol/triethylamine, 95/15/0.1%, mixture. 6.6 mg of the triethylammonium salt of methyl trans-4,5,6,8-tetrahydro-6-oxo-1-(phenylethyl)-5-(sulfoxy)-1H-4,7-methanopyrazolo[3,4-e][1,3]diazepine-8-carboxylate having the empirical formula $C_{23}H_{33}N_5O_7S$ are obtained (M=523.61 g).

The corresponding yield is 20%.

LC/MS (negative electrospray) m/z:

TR=13.02 min $[MH]^-$=421 and $[2M+Na-2H]^-$=865.

Example 3

Triethylammonium Salt of Methyl trans-2,5,6,8-tetrahydro-6-oxo-2-(2-phenylethyl)-5-(sulfoxy)-4H-4,7-methanopyrazolo[3,4-e][1,3]diazepine-8-carboxylate Stage A The procedure is carried out as in Stage M of Example 1 with 0.037 g of the isomer B obtained in Stage A of Example 2, 0.022 g of palladium on carbon, and 0.5 ml of methanol. 28 mg of the compound methyl trans-2,5,6,8-tetrahydro-5-hydroxy-6-oxo-2-(2-phenylethyl)-4H-4,7-methanopyrazolo[3,4-e][1,3]diazepine-8-carboxylate having the empirical formula $C_{17}H_{18}N_4O_4$ are obtained (342.36 g).

The corresponding yield is 96%.

Stage B

The procedure is carried out as in Example 1 in Stage M with 0.028 g of the product obtained in the preceding stage A, 0.039 g of the pyridine-$SO_3$ complex and 1 ml of pyridine. 20 mg of the triethylammonium salt of methyl trans-2,5,6,8-tetrahydro-6-oxo-2-(2-phenylethyl)-5-(sulfoxy)-4H-4,7-methanopyrazolo[3,4-e][1,3]diazepine-8-carboxylate having the empirical formula $C_{23}H_{33}N_5O_7S$ are obtained (M=523.61 g).

The corresponding yield is 47%.

LC/MS (negative electrospray), m/z:

TR=11.87 min $[2M^-+Na-2H]^-$=865$^-$ and $[M]^-$=421$^-$

Example 4

Triethylammonium Salt of Ethyl Trans-4,5,6,8-tetrahydro-8-(methoxycarbonyl)-6-oxo-5-(sulfoxy)-1H-4,7-methanopyrazolo[3,4-e][1,3]diazepine-1-acetate.

Stage A 0.2 g of the product obtained in Stage K of Example 1 is dissolved in 2 ml of acetonitrile, in a round-bottomed flask. 0.150 µl of ethyl bromoacetate and 240 µl of DIEA are added. The medium is heated at 50° C. for 24 hours and then the reaction medium is extracted with ethyl acetate, the organic phase is washed with an aqueous tartaric acid solution at 10% and then with an aqueous NaCl solution. The organic phase is dried over magnesium sulfate, filtered off and the solvent is evaporated off under reduced pressure. 266 mg of the crude product are obtained which are purified by chromatography on silica, eluting with a methylene chloride/acetone/triethylamine, 95/0.5/0.1%, mixture. 37 mg of the isomer A, ethyl trans-4,5,6,8-tetrahydro-8-(methoxycarbonyl)-6-oxo-5-(phenylmethoxy)-1H-4,7-methanopyrazolo[3,4-e][1,3]diazepine-1-acetate having the empirical formula $C_{20}H_{22}N_4O_6$ are obtained (M=414.42 g).

The corresponding yield is 11.8%.

88 mg of the isomer B, ethyl trans-5,6-dihydro-8-(methoxycarbonyl)-6-oxo-5-(phenylmethoxy)-4H-4,7-methanopyrazolo[3,4-e][1,3]diazepine-2(8H)-acetate having the empirical formula $C_{20}H_{22}N_4O_6$ are also obtained (412.42 g).

The corresponding yield is 28%.

Stage B

The procedure is carried out as in Stage M of Example 1 with 0.020 g of the isomer A obtained in the preceding stage, 0.01 g of palladium on carbon and 0.5 ml of methanol. 24.2 mg of the compound ethyl trans-4,5,6,8-tetrahydro-5-hydroxy-8-(methoxycarbonyl)-6-oxo-1H-4,7-methanopyrazolo[3,4-e][1,3]diazepine-1-acetate having the empirical formula $C_{13}H_{16}N_4O_6$ are obtained (324.30 g).

The corresponding yield is 83%.

Stage C

The procedure is carried out as in Stage N of Example 1 with 0.024 g of the product obtained in the preceding stage, 0.035 g of the pyridine-$SO_3$ complex and 1 ml of pyridine. 28.8 mg of the compound of triethylammonium salt of ethyl trans-4,5,6,8-tetrahydro-8-(methoxycarbonyl)-6-oxo-5-(sulfoxy)-1H-4,7-methanopyrazolo[3,4-e][1,3]diazepine-1-acetate having the empirical formula $C_{19}H_{31}N_5O_9S$ are obtained (505.55).

The corresponding yield is 77%.

LC/MS (negative electrospray), m/z:

TR=6.06 min $[M]^-$=403.

proton NMR:

$CDCl_3$ at 300 MHz and 60° C. (chemical shift and multiplicity):

1.28 (t): $CH_3$—$CH_2$—O—CO; 4.20 (q): $CH_3$—$CH_2$—O—CO; 5.06 and 4.96 (AB): O—CO—$CH_2$—N; 3.84 (s): $CH_3$—O—CO; 5.32 (s): $CH_3$—O—CO—CH—N; 3.45 (d) and 3.82 (dd): N—$CH_2$—CH—N; 5.00 (d): N—$CH_2$—CH—N; 7.62 (s): N=CH—C; 1.28 (t): $CH_3$—$CH_2$—N; 3.15 (q): $CH_3$—$CH_2$—N.

Example 5

Triethylammonium Salt of Ethyl Trans-5,6-dihydro-8-(methoxycarbonyl)-6-oxo-5-(sulfoxy)-4H-4,7-methanopyrazolo[3,4-e][1,3]diazepine-2(8H)-acetate.

Stage A

The procedure is carried out as in Stage M of Example 1 with 0.067 g of the isomer B obtained in Stage A of Example 4, 0.038 g of palladium on carbon and 0.4 ml of methanol. 62 mg of the compound ethyl trans-5,6-dihydro-8-(methoxycarbonyl)-6-oxo-5-(phenylmethoxy)-4H-4,7-methanopyrazolo[3,4-e][1,3]diazepine-2(8H)-acetate having the empirical formula $C_{13}H_{16}N_4O_6$ are obtained (324.30 g).

The corresponding yield is 90%.

Stage B

The procedure is carried out as in Stage M of Example 1 with 0.062 g of the product obtained in the preceding stage, 0.091 g of the pyridine-$SO_2$ complex and 2 ml of pyridine. 79 mg of the compound of triethylammonium salt of ethyl trans-5,6-dihydro-8-(methoxycarbonyl)-6-oxo-5-(sulfoxy)-4H-4,7-methanopyrazolo[3,4-e][1,3]diazepine-2(8H)acetate having the empirical formula $C_{19}H_{31}N5O_9S$ are obtained (M=505.55 g).

The corresponding yield is 82%.

LC/MS (negative electrospray), m/z:

TR=5.64 min $M^-$=403.

proton NMR: $CDCl_3$ (chemical shift and multiplicity):

1.28 (t): $CH_3$—$CH_2$OCO; 4.22 (q): $CH_3$—$CH_2$—OCO; 4.90 and 4.80 (AB): $CH_3$—$CH_2$—OCO—$CH_2$—N; 3.85 (s): $CH_3$—O—CO; 5.26 (s): $CH_3$—O—CO—CH—N; 3.63 (d) and 3.82 (dd): N—$CH_2$—CH—N; 4.99 (broad d): N—$CH_2$—CH—C=; 7.53 (s): C=CH—N.

Example 6

Triethylammonium Salt of Methyl 2,5,6,8-tetrahydro-6-oxo-2-[(phenylamino)carbonyl]-5-(sulfoxy)-4H-4,7-methanopyrazolo[3,4-e][1,3]diazepine-8-carboxylate Stage A 0.3 g of the compound obtained in Stage K of Example 1 is dissolved in 5 ml of $CH_2Cl_2$, in a round-bottomed flask. 0.109 g of phenyl isocyanate is added. The reaction medium is then stirred for 1 hour. After evaporation, a crude product is obtained which is purified by chromatography on silica, eluting with a methylene chloride/ethyl acetate/triethylamine, 99/1/0.1%, mixture. 176 mg of the isomer A of methyl trans-4,5,6,8-tetrahydro-6-oxo-1-[(phenylamino)carbonyl]-5-(phenylmethoxy)-1H-4,7-methanopyrazolo[3,4-e][1,3]diazepine-8-carboxylate, and 63.5 mg of the isomer B of methyl trans-2,5,6,8-tetrahydro-6-oxo-2-[(phenylamino)carbonyl]-5-(phenylmethoxy)-4H-4,7-methanopyrazolo[3,4-e][1,3]diazepine-8-carboxylate having the empirical formula $C_{23}H_{21}N_5O_5$ [lacuna] (M=447.45 g).

The corresponding yields of isomers A and B are 36% and 14%.

Stage B

The procedure is carried out as in Stage M of Example 1, with 0.054 g of the isomer B obtained in the preceding stage, 0.008 g of palladium on carbon, 5 ml of methanol, 1 ml of THF. 44 mg of the compound methyl trans-2,5,6,8-tetrahydro-5-hydroxy-6-oxo-2-[(phenylamino)carbonyl]-4H-4,7-methanopyrazolo[3,4-e][1,3]diazepine-8-carboxylate having the empirical formula $C_{16}H_{15}N_5O_5$ are obtained (357.33 g).

The corresponding yield is quantitative.

Stage C

The procedure is carried out as in Stage M of Example 1 with 40 mg of the product obtained in the preceding stage, 62 mg of the pyridine-$SO_3$ complex and 3 ml of pyridine. 21 mg of the compound of triethylammonium salt of methyl 2,5,6,8-tetrahydro-6-oxo-2-[(phenylamino)carbonyl]-5-(sulfoxy)-4H-4,7-methanopyrazolo[3,4-e][1,3]diazepine-8-carboxylate having the empirical formula $C_{22}H31N6O_8S$ are obtained (M=532.59 g).

The corresponding yield is 35%.

LC/MS (negative electrospray), m/z: $MH^-$=436.

proton NMR in DMSO-$d_6$ at 300 MHz, chemical shift and multiplicity:

3.80: $CH_3$—O—CO; 5.17 (s): $CH_3$—O—CO—CH—N; 3.48 (d) and 3.59 (dd): N—$CH_2$—CH—N; 4.91 (d): N—$CH_2$—CH—C=; 8.41 (s): C=CH—N; 7.71 (d), 7.36 (t), 7.14 (t) for aromatic H; 10.40 (s): NH.

Example 7

Triethylammonium Salt of 5,6-dihydro-6-oxo-N-2-phenyl-5-(sulfoxy)-4H-4,7-methanopyrazolo[3,4-e][1,3]diazepine-2,8(8H)-dicarboxamide Stage A 0.445 g of the product of the isomer B obtained in Stage A of Example 8 is dissolved in 10 ml of dioxane, in a round-bottomed flask. 10 ml of water are then added, followed by 0.995 ml of normal sodium hydroxide. An aqueous $NaH_2PO_4$ solution is added to the reaction medium. The medium is extracted twice with ethyl acetate. The organic phase is dried over magnesium sulfate, filtered and the solvent is evaporated under reduced pressure. 460 mg of the compound trans-2,5,6,8-tetrahydro-6-oxo-2-[(phenylamino)carbonyl]-5-(phenylmethoxy)-4H-4,7-methanopyrazolo[3,4-e][1,3]diazepine-8-carboxylic acid having the empirical formula $C_{22}H_{19}N_5O_5$ are obtained (M=433.43 g).

The yield is quantitative.

Stage B 0.16 g of the product obtained in the preceding stage is dissolved in 5 ml of DMF, in a round-bottomed flask placed under a nitrogen atmosphere. 0.239 g of BOP, 0.073 g of HOBt, 0.039 g of $NH_4Cl$ and 0.139 ml of DIEA are successively added. After stirring for 2 h 30 min, ethyl acetate is added and the organic phase is washed with water. The organic phase is then successively washed with a tartaric acid solution at 10%, an $NaHCO_3$ solution, a buffer solution of pH 7, and an aqueous NaCl solution. The organic phase is dried over magnesium sulfate and then filtered and the solvent is separated off under reduced pressure. 160 mg of crude product are obtained, which product is taken up in ether to give 100 mg of the compound trans-5,6-dihydro-6-oxo-N-2-phenyl-5-(phenylmethoxy)-4H-4,7-methanopyrazolo[3,4-e][1,3]diazepine-2,8(8H)-dicarboxamide having the empirical formula $C_{22}H_{20}N_6O_4$ (M=432.44 g).

The corresponding yield is 64%.

Stage C

The procedure is carried out as in Stage M of Example 1 with 0.09 g of the product obtained in the preceding Stage B, 0.018 g of palladium on carbon, 2 ml of THS, 2 ml of methanol and 1 ml of ethyl acetate. 74 mg of the compound trans-5,6-dihydro-6-oxo-$N_2$-phenyl-5-(phenylmethoxy)-4H-4,7-methanopyrazolo[3,4-e][1,3]diazepine-2,8(8H)-dicarboxamide having the empirical formula $C_{15}H_{14}N_6O_4$ are obtained (M=342.32 g).

The yield is quantitative.

Stage D

The procedure is carried out as in Stage M of Example 1 with 0.079 g of the product obtained in the preceding stage, 0.110 g of the pyridine-$SO_3$ complex and 2 ml of pyridine. 26 mg of the compound of triethylammonium salt of 5,6-dihydro-6-oxo-N-2-phenyl-5-(sulfoxy)-4H-4,7-methanopyrazolo[3,4-e][1,3]diazepine-2,8(8H)-dicarboxamide having the empirical formula $C_{20}H_{19}N_7O_7S$ are obtained (M=501.48 g).

The corresponding yield is 25%.

LC/MS (negative electrospray), m/z: $M^-$=421.

Example 8

Triethylammonium Salt of Methyl Trans-2,5,6,8-tetrahydro-6-oxo-2-(phenylsulfonyl)-5-(sulfoxy)-4H-4,7-methanopyrazolo[3,4-e][1,3]diazepine-8-carboxylate Stage A 0.30 g of the product obtained in Stage K of Example 1 is dissolved in 5 ml of dichloromethane, in a round-bottomed flask placed under an argon atmosphere. 0.19 ml of TEA and 0.242 g of phenylsulfonyl chloride are added. After one hour, the reaction medium is washed with an aqueous $NaH_2PO_4$ solution and the organic phase is separated and then dried over magnesium sulfate and filtered. The solvent is evaporated off under reduced presssure to give 850 mg of crude product. The product is purified by chromatography on silica eluting with a CH2Cl2/AcoEt/TEA 95/5/0.1 mixture. 128 mg of the compound methyl trans-2,5,6,8-tetrahydro-6-oxo-5-(phenylmethoxy)-2-(phenylsulfonyl)-4H-4,7-methanopyrazolo[3,4-e][1,3]diazepine-8-carboxylate having the empirical formula $C_{22}H_{20}N_4O_6S$ are obtained (M=468.49 g).

The corresponding yield is 29%.

Stage B

The procedure is carried out as in Stage M of Example 1 with 0.125 g of the product obtained in the preceding stage, 0.156 g of palladium on carbon, 3 ml of THF and 3 ml of methanol. 98 mg of the compound methyl trans-2,5,6,8-tetrahydro-5-hydroxy-6-oxo-2-(phenylsulfonyl)-4H-4,7-methanopyrazolo[3,4-e][1,3]diazepine-8-carboxylate having the empirical formula $C_{15}H_{14}N_4O_6S$ are obtained (M=378.37 g).

The corresponding yield is quantitative.

Stage C

The procedure is carried out as in Stage M of Example 1 with 0.079 g of the product obtained in the preceding stage, 0.10 g of the pyridine-$SO_3$ complex and 3 ml of pyridine. 3.6 mg of the compound of triethylammonium salt of methyl trans-2,5,6,8-tetrahydro-6-oxo-2-(phenylsulfonyl)-5-(sulfoxy)-4H-4,7-methanopyrazolo[3,4-e][1,3]diazepine-8-carboxylate having the empirical formula $C_{20}H_{19}N_5O_9S_2$ are obtained (M=547.53 g).

The corresponding yield is 3.5%.

LC/MS (negative electrospray), m/z: $M^-$=457.

Example 9

Di(triethylammonium) Salt of Trans-5,6-dihydro-8-(methoxycarbonyl)-6-oxo-5-sulfoxy-4H-4,7-methanopyrazolo[3,4-e][1,3]diazepine-2(8H)-acetic acid Stage A 2.0 g of the product obtained in Stage K of Example 1 are dissolved in 20 ml of dry acetonitrile in a round-bottomed flask. 3.1 ml of DIEA are added followed by 1.9 ml of allyl bromoacetate. The medium is stirred overnight at 50° C. and then ethyl acetate is added. The reaction medium is washed with a tartaric acid solution at 10% and then with an aqueous NaCl solution. The organic phase is dried over magnesium sulfate, filtered and the solvent is evaporated under reduced pressure. The crude product obtained is purified by chromatography on silica, eluting with a heptane/ethyl acetate/triethylamine, 1/1/0.1%, mixture. 1.48 g of the compound 2-propenyl trans-5,6-dihydro-8-(methoxycarbonyl)-6-oxo-5-(phenylmethoxy)-4H-4,7-methanopyrazolo[3,4-e][1,3]diazepine-2(8H)acetate having the empirical formula $C_{21}H_{22}N_4O_6$ are obtained (M=426.43 g).

The corresponding yield is 57%.

Stage B 0.084 g of the product obtained in the preceding stage is dissolved in 1 ml of dichloromethane, in a round-bottomed flask. 2 mg of $Pd(PPh_3)_4$ and 0.043 g of $PhSiH_3$ are obtained. After stirring for one hour, 3.5 mg of $Pd(PPh_3)_4$ are again stirred in 1 ml of methylene chloride. The reaction mixture is next evaporated off and then taken up in a THF/water mixture. Ethyl acetate and $NaH_2PO_4$ are added, and the organic phase is then extracted; the latter is washed with water and then dried over magnesium sulfate, filtered and the solvent is evaporated off under reduced pressure. 90.8 mg of the compound trans-5,6-dihydro-8-(methoxycarbonyl)-6-oxo-5-(phenylmethoxy)-4H-4,7-methanopyrazolo[3,4-e][1,3]diazepine-2(8H)-acetic acid having the empirical formula $C_{18}H_{18}N_4O_6$ are obtained (M=386.37 g). The crude product is used as it is in the next stage.

Stage C

The procedure is carried out as in Stage M of Example 1 with 0.090 g of the crude product obtained in the preceding stage, 0.036 g of palladium on carbon and 3 ml of ethanol. 77 mg of the compound trans-5,6-dihydro-5-hydroxy-8-(methoxycarbonyl)-6-oxo-4H-4,7-methanopyrazolo[3,4-e][1,3]diazepine-2(8H)-acetic acid having the empirical formula $C_{11}H_{12}N_4O_6$ are obtained (M=296.24 g).

The yield is quantitative.

Stage D

The procedure is carried out as in Stage M of Example 1 with 0.070 g of the product obtained in the preceding stage, 0.113 g of the pyridine-$SO_3$ complex and 1 ml of pyridine. The crude product is purified on XAD4 resin, eluting with a water/acetone 100/0, 95/5, 50/50 gradient. 14 mg of the compound of di(pyridinium) salt of trans-5,6-dihydro-8-(methoxycarbonyl)-6-oxo-5-sulfoxy-4H-4,7-methanopyrazolo[3,4-e][1,3]diazepine-2(8H)acetic acid having the empirical formula $C_{17}H_{27}N_5O_9S$, $C_6H_{16}N$ are obtained (M=477.50 g).

The corresponding yield is 13%.

LC/MS (negative electrospray), m/z: TR=3.12 min $M^-$=375.

Example 10

Pyridinium Salt of Methyl Trans-1-(aminocarbonyl)-4,5,6,8-tetrahydro-6-oxo-5-(sulfoxy)-1H-4,7-methanopyrazolo[3,4-e][1,3]diazepine-8-carboxylate Stage A 0.188 g of the product obtained in Stage K of Example 1 is dissolved in 30 ml of dichloromethane, in a round-bottomed flask placed under an argon atmosphere at 0° C. 70 µl of diphosgene are added and then after 1 h 15 min 0.49 ml of a concentrated aqueous ammonia solution is added. After one hour, methylene chloride is added to the reaction medium and the organic phase is washed with an aqueous $NaH_2PO_4$ solution and then with an aqueous NaCl solution. The organic phases are dried over magnesium sulfate, filtered and the solvent is evaporated under reduced pressure. The crude product obtained is purified by chromatography on silica, eluting with a methylene chloride/ethyl acetate/triethylamine, 8/2/0.1%, mixture, and then next eluting with a dichloromethane/ethyl acetate/triethylamine, 7/3/0.1%, mixture. After evaporation of the fractions, 32 mg of the isomer A of compound methyl trans-1-(aminocarbonyl)-4,5,6,8-tetrahydro-6-oxo-5-(phenylmethoxy)-1H-4,7-methanopyrazolo[3,4-e][1,3]diazepine-8-carboxylate are obtained with a yield of 15%, and 79 mg of the isomer B of the compound methyl trans-2-(aminocarbonyl)-2,5,6,8-tetrahydro-6-oxo-5-(phenylmethoxy)-4H-4,7-methanopyrazolo[3,4-e][1,3]diazepine-8-carboxylate with a yield of 37%. The empirical formulae of the isomers are $C_{17}H_{17}N_5O_5$ (M=371.36 g).

Stage B

The procedure is carried out as in Stage M of Example 1 with 30 mg of the isomer A obtained in the preceding stage, 9 mg of palladium on carbon, 2 ml of methanol and 0.5 ml of water. 22 mg of the compound methyl trans-1-(aminocarbonyl)-4,5,6,8-tetrahydro-5-hydroxy-6-oxo-1H-4,7-methanopyrazolo[3,4-e][1,3]diazepine-8-carboxylate having the empirical formula $C_{10}H_{11}N_5O_5$ are obtained (M=281.23 g).

The yield is quantitative.

Stage C

The procedure is carried out as in Stage M of Example 1 with 0.022 g of the product obtained in the preceding stage, 0.037 g of the pyridine-$SO_3$ complex and 2 ml of pyridine. The crude product is purified on XAD4 resin with a water/acetone gradient. 13 mg of the compound of pyridinium salt of methyl trans-1-(aminocarbonyl)-4,5,6,8-tetrahydro-6-oxo-5-(sulfoxy)-1H-4,7-methanopyrazolo[3,4-e][1,3]diazepine-8-carboxylate having the empirical formula $C_{15}H_{16}N_6O_8S$ are obtained (M=440.39 g).

The yield is 64%.

LC/MS (negative electrospray): TR=4.20 min $MH^-$=360.

Example 11

Pyridinium Salt of Methyl Trans-2-(aminocarbonyl)-2,5,6,8-tetrahydro-6-oxo-5-(sulfoxy)-4H-4,7-methanopyrazolo[3,4-e][1,3]diazepine-8-carboxylate Stage A The procedure is carried out as in Stage M of Example 1 with 0.079 g of the isomer B obtained in Stage A of Example 10, 0.010 g of palladium on carbon, 4 ml of methanol and 0.5 ml of water. 54 mg of compound methyl trans-2-(aminocarbonyl)-2,5,6,8-tetrahydro-5-hydroxy-6-oxo-4H-4,7-methanopyrazolo[3,4-e][1,3]diazepine-8-carboxylate having the empirical formula $C_{10}H_{11}N_5O_5$ are obtained (M=281.23 g).

The corresponding yield is 98%.

Stage B

The procedure is carried out as in Stage M of Example 1 with 0.059 g of the product obtained in the preceding stage, 0.1 g of the pyridine-$SO_3$ complex and 3 ml of pyridine. The crude product is purified on XAD4 resin with a water/acetone gradient. 40 mg of the compound of pyridinium salt of methyl trans-2-(aminocarbonyl)-2,5,6,8-tetrahydro-6-oxo-5-(sulfoxy)-4H-4,7-methanopyrazolo[3,4-e][1,3]diazepine-8-carboxylate having the empirical formula $C_{16}H_{15}N_6O_8S$ are obtained (M=440.39 g).

The corresponding yield is 45%.

LC/MS (negative electrospray): TR=3.63 min $MH^-$=360.

Example 12

Sodium Salt of 1,1-dimethylethyl 2-(4,5,6,8-tetrahydro-6-oxo-5-(sulfoxy)-1H-4,7-methanopyrazolo[3,4-e][1,3]diazepin-1-yl)ethyl]carbamate Stage A 50 g of BOC—NH—$NH_2$ are dissolved in 250 ml of anhydrous DMF, in a round-bottomed flask placed under an inert atmosphere. The medium is cooled to −10° C., 16.5 g of sodium hydride at 50% in oil are then added in small fractions.

Propylene bromide is then added and the medium is kept stirred overnight at room temperature. Water and a 1 M sodium hydrogen phosphate solution are then slowly added, followed by 200 ml of an AcOEt/heptane 2/1 mixture, and then the medium is extracted and the organic phase is dried over magnesium sulfate.

The medium is filtered and the solvent is next evaporated off under reduced pressure. The crude product obtained is purified on silica, eluting with a dichloromethane/AcOEt 95/5 mixture.

24 g of pure 1,1-dimethylethyl 2-(2-propenyl)-hydrazinecarboxylate are thus recovered.

The corresponding yield is 76%.

Stage B 24 g of the product obtained in Stage A are dissolved in 80 ml of AcOEt.

The medium is cooled to 0° C., 332 ml of a 5.5 N hydrochloric acid solution in AcOEt are then added. The medium is stirred for 1 hour 30 minutes at room temperature, and then filtered and washed with ether.

15 g of (2-propenyl)hydrazine having the empirical formula $C_3H_8N_2.2HCl$ are thus obtained in the form of white crystals.

The corresponding yield is 84%.

Stage C 11 g of the product having the empirical formula $C_{14}H_{21}N_3O_4$ obtained in Stage A2 of Example 1 are dissolved in 130 ml of ethanol.

6.51 g of the product obtained in Stage B and 11.33 g of potassium carbonate are added.

The suspension is stirred for 45 minutes, and then the ethanol is evaporated off under reduced pressure. The residue is solubilized in AcOEt, and then the organic phase is washed with water, it is then dried over magnesium sulfate, filtered and the solvent is evaporated off under reduced pressure.

10.8 g of 1,1-dimethylethyl 3,5-dioxo-4-[[2-(2-propenyl)hydrazino]methylene]-1-piperidinecarboxylate having the empirical formula $C_{14}H_{21}N_3O_3$ are thus obtained (M=295.34 g).

The corresponding yield is 80%.

Stage D 10.8 g of the product obtained in Stage C are dissolved in 120 ml of toluene.

1 g of p-toluenesulfonic acid monohydrate is added and the medium is heated under reflux for one hour.

The medium is allowed to cool, it is poured into AcOEt, the organic phase is washed with water and it is dried over magnesium sulfate. The solvent is evaporated off under reduced pressure.

8.5 g of crude product are thus obtained, which product is purified by chromatography on silica, eluting with a heptane/AcOEt 2/1 mixture.

7.5 g of 1,1-dimethylethyl 4,7-dihydro-4-oxo-1-(2-propenyl)-1H-pyrazolo[3,4-c]pyridine-6(5H)-carboxylate having the empirical formula $C_{14}H_{19}N_3O_3$ are thus recovered (M=277.33 g).

The corresponding yield is 74%.

Stage E 7.5 g of the product obtained in Stage D are introduced into a round-bottomed flask. 4.74 g of O-benzylhydroxylamine are next added, followed by 150 ml of pyridine. The medium is stirred for 1 hour at 20° C. The solvent is next evaporated off under reduced pressure and then the medium is diluted with dichloromethane, washed with an aqueous tartaric acid solution at 10%, then with demineralized water. The organic phase is then dried over sodium sulfate and the solvent is evaporated off under reduced pressure. The crude product obtained is then chromatographed on silica, eluting with a dichloromethane/AcOEt 95/5 mixture to give 9.72 g of 1,1-dimethylethyl 4,7-dihydro-4-[(phenylmethoxy)imino]-1-(2-propenyl)-1H-pyrazolo[3,4-c]pyridine-6(5H)-carboxylate having the empirical formula $C_{21}H_{26}N_4O_3$ (M=382.47 g).

The corresponding yield is 90%.

Stage F 9.2 g of the product obtained in Stage E are introduced into 750 ml of methanol. The medium is cooled to around 0-5° C., and 24.2 g of $NaBH_3CN$ and 36.51 ml of boron trifluoride etherate are then added. The medium is stirred for 30 minutes, while it is kept at 0-5° C., the temperature is then allowed to return to 20° C. and the medium is stirred at this temperature for 30 minutes. The reaction medium is next poured into water saturated with sodium hydrogen carbonate. The medium is stirred for 45 minutes, and then separated by decantation, the organic phase is washed with demineralized water and it is dried over sodium sulfate. The solvent is then evaporated off under reduced pressure to give the crude product which is purified by chromatography on silica, eluting with dichloromethane containing 2% acetone.

5.3 g of 1,1-dimethylethyl 4,7-dihydro-4-[(phenylmethoxy)amino]-1-(2-propenyl)-1H-pyrazolo[3,4-c]pyridine-6(5H)-carboxylate having the empirical formula $C_{21}H_{28}N_4O_3$ are thus obtained (M=384.48 g).

The corresponding yield is 60%.

Stage G

The procedure is carried out as indicated in Stage I of Example 1 with 5.25 g of the product obtained in Stage F and a 5.5 N hydrogen chloride solution. The procedure is carried out as indicated in Stage J of Example 1 on the product obtained.

3.95 g of N-(phenylmethoxy)-1-(2-propenyl)-4,5,6,7-tetrahydro-1H-pyrazolo[3,4-c]pyridin-4-amine having the empirical formula $C_{16}H_{20}N_4O$ are thus obtained (M=284.36 g).

The corresponding yield is 90%.

Stage H

The procedure is carried out as indicated in Stage K of Example 1 with 3.8 g of the product obtained in Stage G, 4.2 ml of TEA and 0.8 ml of diphosgene.

2.5 g of 5-(phenylmethoxy)-1-(2-propenyl)-4,5,7,8-tetrahydro-4,7-methanopyrazolo[3,4-e][1,3]diazepin-6(1H) one having the empirical formula $C_{17}H_{18}N_4O_2$ are thus obtained (M=310.36 g).

The corresponding yield is 68%.

Stage I 6 g (19.33 mmol) of the product obtained in the preceding Stage H are dissolved in 180 ml of THF, 180 ml of tert-butanol and 60 ml of water. 3.92 g (29 mmol) of N-methylmorpholine N-oxide are introduced therein, followed by 2.98 ml (0.579 mmol) of osmium tetroxide. The medium is stirred for 54 hours at room temperature. After evaporation of the THF, the medium is taken up in a 1 M aqueous $NaH_2PO_4$ solution. The medium is extracted with an ethyl acetate/heptane at 20% mixture and then with dichloromethane/methylene chloride and THF. After drying the organic phase over $MgSO_4$ and then evaporating the solvents under reduced pressure, 6.16 g of 1-(2,3-dihydroxypropyl)-1,4,5,8-tetrahydro-5-(phenylmethoxy)-6H-4,7-methanopyrazolo[3,4-e][1,3]diazepin-6-one having the empirical formula $C_{17}H_{20}N_4O_4$ are obtained (M=344.37 g).

The corresponding yield obtained is 93%.

Stage J 6.13 g (17.8 mmol) of the product obtained in the preceding stage I are dissolved in 140 ml of THF. 45 ml of methanol are then added, followed by 45 ml of water. The solution obtained is cooled to 0° C. 6.08 g of sodium metaperiodate are then added. The medium is stirred for 2 hours, while the temperature is allowed to rise to 20° C. After 2 hours, 1.52 g of sodium metaperiodate are added and the medium is again stirred for 40 minutes. Once the reaction is complete, 260 ml of a 1 M aqueous $NaH_2PO_4$ solution are added, and then the solution is saturated with solid NaCl and extracted with THF and with an ethyl acetate/heptane at 30% mixture. The organic phase is washed with a saturated aqueous $NaH_2PO_4$ solution and then dried over $MgSO_4$. After evaporation of the solvent under reduced pressure, 9.98 g of 4,5,6,8-tetrahydro-6-oxo-5-(phenylmethoxy)-1H-4,7-methanopyrazolo[3,4-e][1,3]diazepine-1-acetaldehyde having the empirical formula $C_{16}H_{16}N_4O_4$ are obtained (M=342.39 g).

The yield obtained is quantitative.

Stage K 5.6 g of the product obtained in the preceding Stage J are dissolved in 100 ml of ethanol and then 2.71 g of $NaBH_4$ are added, at 0° C. in portions. The medium is stirred for 2 hours at 0° C. and then the ethanol is evaporated off, ice, methylene chloride and, little by little, a 1 M aqueous $NaH_2PO_4$ solution are added. The gaseous emission is high. The aqueous phase is then extracted with methylene chloride and the organic phase is washed with a thiosulfate solution in order to remove the $NaIO_4$ residues. After drying the organic phase over $MgSO_4$, the solvents are evaporated off under reduced pressure.

A solid residue is obtained which is crystallized from an ethyl ether and isopropanol mixture. After filtration, 3.45 g of 1,4,5,8-tetrahydro-1-(2-hydroxyethyl)-5-(phenylmethoxy)-6H-4,7-methanopyrazolo[3,4-e][1,3]diazepin-6-one having the empirical formula $C_{16}H_{18}N_4O_3$ are obtained (M=314.35 g.

The corresponding yield is 62%.

Stage L 1.35 g (4.29 mmol) of the product obtained in the preceding Stage K are dissolved in 50 ml of THF. 0.69 ml of pyridine are then added at room temperature, followed by 1.46 g of triphenylphosphine. 1.42 g of iodine are added in portions and then, after 2 hours, 200 mg of iodine, 220 mg of triphenylphosphine and 0.13 ml of pyridine are added. An $NaH_2PO_4$ solution is poured into the medium and then extracted with an ethyl acetate/heptane mixture, and the organic phase is washed with a saturated aqueous NaCl solution. After evaporation of the solvents under reduced pressure of the organic phase, 1.6 g of crude product are obtained, which product is purified by liquid chromatography, eluting with a dichloromethane/acetonitrile at 10% mixture. 1.60 g of the product 1,4,5,8-tetrahydro-1-(2-iodoethyl)-5-(phenylmethoxy)-6H-4,7-methanopyrazolo[3,4-e][1,3]diazepin-6-one having the empirical formula $C_{17}H_{17}IN_4O_2$ are obtained (M=424.24 g).

The yield obtained is 88%.

Stage M 408 g of the product obtained in the preceding stage L are dissolved in 4 ml of DMF. The solution is stirred at room temperature in the presence of 128 mg of sodium azide. The medium is stirred for 5 hours and then the solution is treated with an aqueous NaH2PO4 solution and the medium is extracted with an ethyl acetate/heptane 1/1 mixture. The organic phase is washed with a saturated aqueous NaCl solution, and then the solvents are evaporated off under reduced pressure. 328 mg of the compound 1-(2-azidoethyl)-1,4,5,8-tetrahydro-5-(phenylmethoxy)-6H-4,7-methanopyrazolo[3,4-e][1,3]diazepin-6-one having the empirical formula $C_{16}H_{17}N_7O_2$ are obtained (M=339.36 g).

The corresponding yield is quantitative.

Stage N 323 mg of the product obtained in the preceding stage are dissolved in 10 ml of anhydrous THF. The solution is cooled to 0° C. and then 300 mg of triphenylphosphine are added in portions. The reaction medium is stirred at room temperature for 16 hours. Once the reaction is complete, 345 µl of demineralized water are added and the medium is stirred for several hours. After treatment, the compound 1-(2-aminoethyl)-1,4,5,8-tetrahydro-5-(phenylmethoxy)-6H-4,7-methanopyrazolo[3,4-e][1,3]diazepin-6-one having the empirical formula $C_{16}H_{19}N_5O_2$ is obtained (M=313.36 g).

Stage O

The compound obtained in the preceding stage is dissolved in 5 ml of anhydrous THF. 280 µl of triethylamine are added followed by 182 mg of Boc anhydride in solution in 0.5 ml of THF. The reaction is stirred for 2 hours and then the reaction medium is washed with $NaH_2PO_4$, and it is extracted with a mixture of ethyl acetate containing 20% of heptane. The organic phase is dried over magnesium sulfate, filtered and the solvent is then evaporated off under reduced pressure. The oily residue obtained is taken up in ether and triturated with pentane. After filtration of the precipitated Pϕ$_3$O, the filtrate is evaporated off and then purified by chromatography on silica, eluting with a toluene isopropyl alcohol at 18 to 15% mixture. After evaporation, 362 mg of the compound 1,1-dimethylethyl [2-[4,5,6,8-tetrahydro-6-oxo-5-(phenylmethoxy)-1H-4,7-methanopyrazolo[3,4-e][1,3]diazepin-1-yl]ethyl]carbamate having the empirical formula $C_{21}H_{27}N_5O_4$ are obtained (M=413.48 g).

The corresponding yield is 81%.

Stage P

The procedure is carried out as in Stage M of Example 1 with 339 mg of the product obtained in the preceding stage, 750 mg of palladium on carbon in 17 ml of ethanol/acetic acid mixture (1 drop of acetic acid per 1 ml of ethanol). 281 mg of compound 1,1-dimethylethyl [2-(4,5,6,8-tetrahydro-5-hydroxy-6-oxo-1H-4,7-methanopyrazolo[3,4-e][1,3]diazepin-1-yl)ethyl]carbamate having the empirical formula $C_{14}H_{28}N_5O_4$ are obtained (M=323.35 g).

The yield obtained is quantitative.

Stage Q

The procedure is carried out as in Stage M of Example 1 with the crude product obtained in the preceding stage, 400 mg of the pyridine-$SO_3$ complex and 6 ml of pyridine. The pyridinium salts of the expected product are obtained.

Stage R

The pyridinium salt obtained in the preceding stage is taken up in an aqueous solution containing 10% of THF. The solution is passed over 90 g of Dowex resin activated beforehand with sodium hydroxide. The fractions are then lyophilized and 60 mg of crude product are obtained, which product is purified from acetone. After evaporation, the residue is redissolved in 1 ml of demineralized water and then attached. 255 mg of compound of sodium salt of 1,1-dimethylethyl 2-(4,5,6,8-tetrahydro-6-oxo-5-(sulfoxy)-1H-4,7-methanopyrazolo[3,4-e][1,3]diazepin-1-yl)ethyl]carbamate having the empirical formula $C_{14}H_{20}N_5O_7S$ Na are obtained (M=425.20 g).

The yield obtained is 73%.

proton NMR, DMSO-$d_6$, 300 MHz (chemical shift and multiplicity):

1.38 (s): 0-C—$(CH_3)_3$; 3.07 (d) and 3.49 (dd): N—$CH_2$—CH; 4.67 (d): N—$CH_2$—CH; 3.94 (m): N—$CH_2$—$CH_2$—NH; 3.20 (m): N—$CH_2$—$CH_2$—NH; 6.95 (tl): N—$CH_2$—$CH_2$—NH; 4.26 and 4.33: N—$CH_2$—C=; 7.39 (s): N=CH.

LC/MS (negative electrospray), m/z: $M^-$=402.1, $(2M+Na^+)^-$=827.2.

Example 13

Sodium Salt of 1-(2-aminoethyl)-1,4,5,8-tetrahydro-5-(sulfoxy)-6H-4,7-methanopyrazolo[3,4-e][1,3]diazepin-6-one Stage A 140 mg of the product obtained in Stage R of Example 12 are dissolved in 2 ml of trifluoroacetic acid. The trifluoroacetic acid solution is cooled beforehand to 0° C. The medium is stirred for 10 minutes at 0° C. and then the trifluoroacetic acid is evaporated off. The residue is treated more than once by adding toluene and the latter is evaporated off in order to remove the residual trifluoroacetic acid. The residue is washed with an $H_2O$/THF at 10% mixture and then dried under vacuum. 90 mg of the compound of sodium salt of 1-(2-aminoethyl)-1,4,5,8-tetrahydro-5-(sulfoxy)-6H-4,7-methanopyrazolo[3,4-e][1,3]diazepin-6-one having the empirical formula $C_9H_{12}N_5O_5S$ Na are obtained (M=325.28 g).

proton NMR, DMSO-$d_6$, 300 MHz, chemical shift and multiplicity.

3.09 (d) and 3.52 (dd): N—$CH_2$—CH; 4.72 (d): N—$CH_2$—CH; 4.38 (broad s): N—$CH_2$—C=; 3.22 (broad t), 4.13 (m): N—$CH_2$—$CH_2$—$NH_2$; 7.86 (broad s): N—$CH_2$—$CH_2$—$NH_2$; 7.51 (s): N=CH.

LC/MS (negative electrospray), m/z: $M^-$=302.1 g, $(2M^-+H^+)^-$=605.0 g and $(2M^-+Na^+)^-$=627.1 g.

Example 14

Sodium Salt of 1-[2-[(aminocarbonyl)oxy]ethyl]-1,4,5,8-tetrahydro-5-(sulfoxy)-6H-4,7-methanopyrazolo[3,4-e][1,3]diazepin-6-one Stage A 0.172 g of the compound obtained in Stage K of Example 12 is dissolved in dichloromethane. 122 mg of DMAP and 202 mg of p-$NO_2$ PhO-COCl are added at 0° C. The medium is stirred for one hour at 0° C. under an argon atmosphere and then evaporated to dryness and the residue is solubilized in DMF. Gaseous $NH_3$ is bubbled through for 20 seconds and the medium is stirred for 5 minutes. The yellow suspension obtained is poured into ethyl acetate and washed several times with an aqueous $NaHCO_3$ solution at 10%. The organic phase is evaporated off and the residue is reextracted with THF. After evaporation of the THF, the residue is taken up in ethyl acetate and 80 mg of white crystals of the compound 1-[2-[(aminocarbonyl) oxy]ethyl]-1,4,5,8-tetrahydro-5-(phenylmethoxy)-6H-4,7-methanopyrazolo[3,4-e][1,3]diazepin-6-one having the empirical formula $C_{17}H_{19}N_9O_4$ are obtained (M=357.37 g).

The corresponding yield is 81%.

Stage B

The procedure is carried out as in Stage M of Example 1 with 0.070 g of the product obtained in the preceding stage and 1.5 ml of acetic acid. 52 mg of the product 1-[2-[(aminocarbonyl)oxy]ethyl]-1,4,5,8-tetrahydro-5-hydroxy-6H-4,7-methanopyrazolo[3,4-e][1,3]diazepin-6-one having the empirical formula $C_{10}H_{13}N_5O_4$ are obtained (M=267.25 g).

The yield is quantitative.

Stage C

The procedure is carried out as in Stage M of Example 1 with 0.052 g of the product obtained in the preceding stage, 0.070 g of the pyridine-$SO_3$ complex and 2 ml of pyridine. The pyridinium salt of the expected compound is obtained; the latter is then treated as in Stage R of Example 12 on Dowex resin and 62 mg are obtained in the form of yellow crystals of the compound of sodium salt of 1-[2-[(aminocarbonyl)oxy]ethyl]-1,4,5,8-tetrahydro-5-(sulfoxy)-6H-4,7-methanopyrazolo[3,4-e][1,3]diazepin-6-one having the empirical formula $C_{10}H_{12}N_5O_7S$ Na (M=346.30+22.99 g).

The yield obtained is 78%.

LC/MS (negative electrospray), m/z: M$^-$346.1 proton NMR, DMSO-$d_6$, 300 MHz, chemical shift and multiplicity:

3.11 (d) and 3.49 (dd): N—$CH_2$—CH; 4.68 (d): N—$CH_2$—CH; 4.12 (m): N—$C_2$—$CH_2$—O; 6.54 (broad s): $NH_2$ and 7.39 (s): N=CH.

Example 15

Sodium Salt of 4,5,6,8-tetrahydro-6-oxo-5-(sulfoxy)-1H-4,7-methanopyrazolo[3,4-e][1,3]diazepine-1-acetamide Stage A 0.54 g of the product obtained in Stage J of Example 12 is dissolved in acetonitrile. A solution of 30 mg of $NaH_2PO_4$ in 0.3 ml of water is added. A 0.189 ml solution of an $H_2O_2$ solution at 30% is then added, and finally a solution of 0.22 g of $NaO_2Cl$ in 2 ml of water is added dropwise over 30 minutes. The medium is kept stirred at room temperature for 4 hours. An aqueous $NaHCO_3$ solution is then added and the medium is extracted several times with ethyl acetate. The aqueous phase is treated with aqueous $NaHSO_4$ and then extracted with an ethyl acetate-THF mixture. The organic phase is dried over magnesium sulfate, filtered and, after evaporation of the solvent, 0.290 mg is obtained in the form of white crystals of the compound 4,5,6,8-tetrahydro-6-oxo-5-(phenylmethoxy)-1H-4,7-methanopyrazolo[3,4-e][1,3]diazepine-1-acetic acid having the empirical formula $C_{16}H_{16}N_4O_4$ (M=328.33 g).

The corresponding yield is 52%.

Stage B 0.29 g of the compound obtained in the preceding stage is dissolved in 32 ml of DMF. 0.59 g of BOP is added followed by 0.188 g of HOBT. The medium is stirred for 5 minues and then 0.099 g of $NH_4Cl$ is added followed by 0.64 ml of diisopropylethylamine. The medium is stirred for two hours at room temperature and then the reaction medium is poured into 0.1 N hydrochloric acid and the medium is extracted with THF. The organic phase is washed with an $NHCO_3$ solution and then the organic phase is dried over magnesium sulfate and the solvent is evaporated off under reduced pressure. A crude product is obtained which is taken up in methanol. 0.066 g is obtained in the form of white crystals of compound 4,5,6,8-tetrahydro-6-oxo-5-(phenylmethoxy)-1H-4,7-methanopyrazolo[3,4-e][1,3]diazepine-1-acetamide, having the empirical formula $C_{16}H_{17}N_5O_3$ (M=327.35 g).

The corresponding yield is 23%.

Stage C

The procedure is carried out as in Stage M of Example 1 with 56 mg of the product obtained in the preceding stage, 1 ml of acetic acid and 20 mg of palladium on carbon. 48 mg are obtained in the form of white crystals of the compound 4,5,6,8-tetrahydro-5-hydroxy-6-oxo-1H-4,7-methanopyrazolo[3,4-e][1,3]diazepine-1-acetamide having the empirical formula $C_9H_{11}N_5O_3$ (M=237.22 g).

The corresponding yield is quantitative.

Stage D

The procedure is carried out as in Stage M of Example 1 with 0.048 g of the compound obtained in the preceding stage, 1.5 ml of pyridine and 0.1 g of the pyridine-$SO_3$ complex. 33 mg of the expected pyridine salt are obtained.

Stage E

The procedure is carried out as in Stage R of Example 12 and the sodium salt of the expected compound of sodium salt of 4,5,6,8-tetrahydro-6-oxo-5-(sulfoxy)-1H-4,7-methanopyrazolo[3,4-e][1,3]diazepine-1-acetamide having the empirical formula $C_9H_{10}N_5O_6SNa$ is obtained (M=316.27 g+23 g).

LC/MS (negative electrospray) M$^-$=316.

proton NMR, DMSO-$d_6$, 300 MHz, chemical shift and multiplicity:

3.07 (d), 3.49 (dd): N—$CH_2$—CH; 4.68 (d): N—$CH_2$—CH; 4.23 and 4.37: N—$CH_2$—C=; 4.59 and 4.67: $CH_2$—CO—$NH_2$; 7.36 (s): N=CH.

Example 16

Disodium Salt of 1,4,5,8-tetrahydro-5-(sulfoxy)-1-[2-(sulfoxy)ethyl]-6H-4,7-methanopyrazolo[3,4-e][1,3]diazepin-6-one Stage A 0.080 g of the product obtained in Stage K of Example 12 is solubilized in 1 ml of ethanol and 0.5 ml of THF. 20 mg of 10% palladium on carbon are added and the medium is placed under hydrogen. After stirring for 4 hours at room temperature the catalyst is filtered off and the solution is evaporated to dryness. 0.059 g of a resin is obtained which is used as it is in the next step.

Stage B 0.059 mg of the resin obtained in the preceding stage is solubilized to 2 ml of pyridine in the presence of 0.250 g of pyridine-$SO_3$ complex. After stirring overnight at room temperature, the solution is evaporated to dryness and the residue is filtered on Dowex resin prepared beforehand with sodium hydroxide, the elution is carried out with a water-THF, 90/10, mixture. After evaporation to dryness of the fraction, the residue is taken up in methanol and then in ether. 0.70 g is obtained in the form of yellow crystals of the disodium salt of 1,4,5,8-tetrahydro-5-(sulfoxy)-1-[2-(sulfoxy)ethyl]-6H-4,7-methanopyrazolo[3,4-e][1,3]diazepin-6-one having the empirical formula $C_9H_{10}N_4O_9S_2$ 2NA (M=382.33+46 g).

The yield obtained is 65%.

proton NMR, DMSO-$d_6$, 300 MHz, chemical shift and multiplicity:

3.02 (d), 3.47 (dd): N—$CH_2$—CH; 4.67 (d): N—$CH_2$—CH; 3.95 (m), 4.13 (m): N—$CH_2$—$CH_2$—O; 4.32 and 4.41: N—$CH_2$—C=; 7.32 (s): N=CH.

LC/MS (negative electrospray) (M$^{2-}$+Na)$^-$=405.0 g. (M$^{2-}$+H)$^-$=383.1 g.

Example 17

Sodium Salt of 4,5,6,8-tetrahydro-6-oxo-5-(sulfoxy)-1H-4,7-methanopyrazolo[3,4-e][1,3]diazepine-1-carboxamide Stage A 1.6 g of the product obtained in Stage L of Example 12 are dissolved in 16 ml of anhydrous DMF. 260 mg of potassium cyanide are added and the medium is stirred at room temperature for 20 hours. The reaction medium is washed with water and then extracted with an ethyl acetate/heptane at 20% mixture. The organic phase is dried over magnesium sulfate and then, after evaporation of the solvents under reduced pressure, a crude residue is obtained which is purified by chromatography on silica, eluting with first of all dichloromethane and then a dichloromethane/methanol at 10% mixture. After evaporation of the fractions containing the expected product, 1.20 g of 4,5,6,8-tetrahydro-6-oxo-5-(phenylmethoxy)-1H-4,7-methanopyrazolo[3,4-e][1,3]diazepine-1-propanenitrile having the empirical formula $C_{17}H_{17}N_5O_2$ are obtained (M=323.36 g).

The corresponding yield is 98%.

Stage B 2.15 g of the product obtained in the preceding stage are dissolved in 20 ml of anhydrous DMF. The solution is cooled to 0° C. and then 290 mg of NaH at 50% in oil are added. The medium is stirred for 3 h 30 min at 0° C. The solution is treated with $NaH_2PO_4$ and extracted with an ethyl acetate/heptane at 20% mixture. The organic phases are dried over magnesium sulfate, filtered and the solvent is evaporated off under reduced pressure. 1.19 g of compound 1,4,5,8-tetrahydro-5-(phenylmethoxy)-6H-4,7-methanopyrazolo[3,4-e][1,3]diazepin-6-one having the empirical formula $C_{14}H_{14}N_4O_2$ are obtained (M=270.29 g).

The corresponding yield is 42%.

Stage C

A solution cooled to 0° C. of 451 mg of the product obtained in the preceding stage is prepared in 45 ml of anhydrous methylene chloride. 700 µl of triethylamine are added to this solution followed by 201 µl of diphosgene, still at 0° C. The medium is stirred for 2.5 hours at 0° C. and then ammonia is bubbled through for 20 minutes at 0° C. The reaction medium is treated with $NaH_2PO_4$ and then the medium is evaporated to dryness. The residue is triturated in isopropyl ether and pentane and is then isolated by filtration. The solid residue is purified by chromatography on silica, eluting with a methylene chloride/methanol, 90/10, mixture. 200 mg of the compound 4,5,6,8-tetrahydro-6-oxo-5-(phenylmethoxy)-1H-4,7-methanopyrazolo[3,4-e][1,3]diazepine-1-carboxamide having the empirical formula $C_{15}H_{15}N_5O_3$ are obtained (M=313.32 g).

The corresponding yield is 38%.

Stage D

The procedure is carried out as in Stage M of Example 1, with 190 mg of the product obtained in the preceding stage, 475 mg of palladium on carbon and 10 ml of ethanol in the presence of 1% acetic acid. 150 mg of compound 4,5,6,8-tetrahydro-5-hydroxy-6-oxo-1H-4,7-methanopyrazolo[3,4-e][1,3]diazepine-1-carboxamide are obtained.

The corresponding yield is quantitative.

Stage E

The procedure is carried out as in Stage M of Example 1 with 150 mg of the product obtained in the preceding stage, 427 mg of the pyridine-$SO_3$ complex and 3 ml of pyridine. 130 mg of the expected pyridinium salt are obtained.

Stage F

The procedure is carried out as in Stage R of Example 12 starting with 130 mg of the pyridinium salt obtained in the preceding stage in the presence of Dowex resin. 130 mg of the compound of sodium salt of 4,5,6,8-tetrahydro-6-oxo-5-(sulfoxy)-1H-4,7-methanopyrazolo[3,4-e][1,3]diazepine-1-carboxamide having the empirical formula $C_8H_8N_5O_6S,Na$ are obtained (M=325.24 g).

LC/MS (negative electrospray): m/z:

MH⁻=302; MH⁻—$CONH_2$=259 proton NMR, DMSO-$d_6$, 300 MHz, chemical shift and multiplicity:

3.22 (d), 3.48 (dd), 3.25 (d) and 3.56 (dd): N—$CH_2$—CH; 4.73 (d) and 4.79 (d): N—$CH_2$—CH; 4.22 and 4.36 (AB), 4.45 and 4.54 (AB): N—$CH_2$=C; 7.76 (broad s), 7.84 (broad s), 7.90 (broad s), 7.94 (broad s): =$OCNH_2$; 7.69 (s), 8.16 (s): N=CH—.

Example 18

Sodium Salt of 1,4,5,8-tetrahydro-1-[(4-methoxyphenyl)methyl]-5-(sulfoxy)-6H-4,7-methanopyrazolo[3,4-e][1,3]diazepin-6-one Stage A The procedure is carried out as in Stage C of Example 12 with 7.8 g of the product obtained in Stage A of Example 1, 6.03 g of the product obtained in Stage A1 of Example 1, 2.93 g of $NaHCO_3$ and 100 ml of ethanol. 8.74 g are obtained in the form of a beige powder of the compound 1,1-dimethyl 4-[[2-[(4-methoxyphenyl)methyl]hydrazino]methylene]-3,5-dioxo-1-piperidinecarboxylate having the empirical formula $C_{19}H_{25}N_3O_5$ (M=375.43 g).

Stage B

The procedure is carried out as in Stage D of Example 12 with 8.74 g of the product obtained in the preceding stage, 800 mg of para-toluenesulfonic acid and 250 ml of toluene. 5.30 g of the compound 1,1-dimethylethyl 1,4,5,7-tetrahydro-1-[(4-methoxyphenyl)methyl]-4-oxo-6H-pyrazolo[3,4-c]pyridine-6-carboxylate having the empirical formula $C_{19}H_{23}N_3O_4$ are obtained (M=357.41 g).

The corresponding yield is 63%.

Stage C

The procedure is carried out as in Stage E of Example 12 with 5.3 g of the product obtained in the preceding stage, 1.79 g of O-benzylhydroxylamine hydrochloride and 5 ml of pyridine. 6.26 g of compound 1,1-dimethylethyl 1,4,5,7-tetrahydro-1-[(4-methoxyphenyl)methyl]-4-[(2-propenyloxy)imino]-6H-pyrazolo[3,4-c]pyridine-6-carboxylate having the empirical formula $C_{22}H_{28}N_4O_4$ are obtained (M=412.49 g).

The corresponding yield is quantitative.

Stage D

The procedure is carried out as in Stage F of Example 12 with 300 mg of the product obtained in the preceding stage, 735 mg of $NaBH_3CN$, 920 µl of $Et_2OBF_3$ and 15 ml of methanol. 55 mg of the compound 1,1-dimethylethyl 1,4,5,7-tetrahydro-1-[(4-methoxyphenyl)methyl]-4-[(2-propenyloxy)amino]-6H-pyrazolo[3,4-c]pyridine-6-carboxylate having the empirical formula $C_{22}H_{30}N_4O_4$ are obtained (M=414.51 g). The yield is 58%.

Stage E

The procedure is carried out as in Stage G of Example 12 with 3.28 g of the product obtained in the preceding stage, 10 ml of ethyl acetate, 14.2 ml of an ethyl acetate/hydrochloric acid mixture, and 11.8 ml of 2 N sodium hydroxide. 2.34 g of the compound 4,5,6,7-tetrahydro-1-[(4-methoxyphenyl)methyl]-4-[(2-propenyloxy)amino]-1H-pyrazolo[3,4-c]pyridine having the empirical formula $C_{17}H_{22}N_4O_2$ are obtained (M=314.39 g).

The corresponding yield is 94%.

Stage F

The procedure is carried out as in Stage H of Example 12 with 2.29 g of the product obtained in the preceding stage, 800 ml of acetonitrile, 439 µl of diphosgene and 2.1 ml of triethylamine. 1.79 g of compound 1,4,5,8-tetrahydro-1-[(4-methoxyphenyl)methyl]-5-(2-propenyloxy)-6H-4,7-methanopyrazolo[3,4-e][1,3]diazepin-6-one having the empirical formula $C_{18}H_{20}N_4O_3$ are obtained (M=340.39 g).

The corresponding yield is 72%.

Stage G 1.5 g of the product obtained in the preceding stage are dissolved in 30 ml of dichloromethane, in a round-bottomed flask placed under an argon atmosphere. 504 µl of acetic acid and 2.6 g of Pd(PPh$_3$)$_4$ are then successively introduced therein. The medium is stirred for 45 minutes at room temperature and then 30 ml of anhydrous pyridine are added, followed by 2.8 g of the pyridine-SO$_3$ complex. The medium is stirred for 2 hours at room temperature. The reaction medium is evaporated to dryness and it is taken up several times in toluene in order to carry away the para-azeotropic pyridine. The residue is taken up in methylene chloride, washed with water, dried over magnesium sulfate and then evaporated to dryness. The residue is purified by chromatography on silica, eluting with pure methylene chloride and then a methylene chloride/acetone, 98/2, mixture, and then eluting methylene chloride/acetone, 92/8, and finally eluting methylene chloride/acetone/triethylamine, 0.6%. After evaporation of the fractions, 2.22 g of the expected phosphonium salt are obtained.

Stage H

The procedure is carried out as in Stage R of Example 12 with the phosphonium salt obtained in preceding stage and 500 g of Dowex resin. 1.29 g of sodium salt of 1,4,5,8-tetrahydro-1-[(4-methoxyphenyl)methyl]-5-(sulfoxy)-6H-4,7-methanopyrazolo[3,4-e][1,3]diazepin-6-one having the empirical formula C$_{15}$H$_{15}$N$_4$O$_6$S,Na are obtained (M=402.36 g).

The corresponding yield is 77%.

LC/MS (negative electrospray): m/z:

M$^-$=379.1; (2M+Na)$^-$=781.2 proton NMR, DMSO-d$_6$, 300 MHz, chemical shift and multiplicity:

3.09(d), 3.45(dd): N—CH$_2$—CH; 4.67(d): N—CH$_2$—CH; 3.73(s): CH$_3$—O—Ph; 4.19 and 4.29 (AB): N—CH$_2$—CN=C; 5.07 and 5.14 (AB): N—CH$_2$—Ph; 6.88 and 7.13 (AA'BB') the 4 aromatic H; 7.39(s) N=CH.

Example 19

Sodium Salt of Methyl Trans-2-(4-fluorophenyl)-4,5,6,8-tetrahydro-6-oxo-5-(sulfoxy)-4,7-methano-7H-thieno[2,3-e][1,3]diazepine-8-carboxylate.

Stage A 48.14 g (0.281 mol) of methyl alpha-amino-2-thiopheneacetate having the empirical formula C$_7$H$_{19}$NO$_2$S (prepared from commercially available alpha-aminothiophene acetic acid according to a technique similar to that described in J. Med. Chem., 26, 1267-1277 (1983)) are dissolved in 930 ml of acetonitrile.

38.8 g of potassium carbonate (0.281 mol) are added, followed by 55.5 ml of BrCH$_2$CO$_2$tBu (0.337 mol).

The medium is heated at 70° C. for 6 and a half hours, and then the temperature is allowed to return to 20° C. and the insolubles are removed by filtration. The medium is partially concentrated under reduced pressure, taken up in 550 ml of AcOEt, washed with water and then with a saturated sodium chloride solution. The organic phase is dried over sodium sulfate, filtered and the solvent is evaporated off under reduced pressure.

90 g of methyl alpha-[[[(1,1-dimethylethoxy)carbonyl]methyl]amino]-2-thiopheneacetate having the empirical formula C$_{13}$H$_{19}$NO$_4$S are thus obtained (M=285.36 g).

Stage B 90 g of the product obtained in Stage A, 620 ml of anhydrous THF and 61.7 ml of diisopropylethylamine are introduced into a round-bottomed flask placed under an argon atmosphere.

The medium is cooled to around 0-5° C., and then 25.2 ml of methyl chloroformate are added. The medium is left in contact for 1 hour 30 minutes at 20° C. The medium is next diluted with AcOEt, and then washed with an aqueous tartaric acid solution at 10% and with demineralized water.

The organic phase is next dried over magnesium sulfate, filtered and the solvent is evaporated off under reduced pressure. 70.9 g of methyl alpha-[[[(1,1-dimethylethoxy)carbonyl]methyl](methoxycarbonyl)amino]-2-thiopheneacetate having the empirical formula C$_{15}$H$_{21}$NO$_6$S are recovered (M=343.40 g).

The corresponding yield in stages A and B is 73.4%.

Stage C 70 g of the product obtained in Stage B are introduced into a round-bottomed flask and the medium is cooled to around 0-5° C. and 900 ml of trifluoroacetic acid/dichloromethane 1/1 mixture are added. The medium is left in contact at 20° C. for 1 hour.

75 g of a crude product are obtained, which product is purified in the following manner. 75 g of product are introduced into 300 ml of ether, and then 33 ml of cyclohexylamine (0.29 mol) are added dropwise at 20° C.

The salt which precipitated is filtered off and washed twice with 50 ml of ether.

The product obtained is redissolved in 200 ml of water, then 36 ml of 6 N hydrochloric acid are added dropwise at 20° C. and then the medium is separated by decantation, and the aqueous phase extracted twice with 300 ml of AcOEt.

The aqueous phases are combined and they are washed with water, and then with a saturated sodium chloride solution.

The organic phase is filtered and dried over magnesium sulfate.

The solvent is evaporated off under reduced pressure.

59.95 g of methyl alpha-[(carboxymethyl)methoxycarbonyl)amino]-2-thiopheneacetate having the empirical formula C$_{11}$H$_{13}$NO$_6$S are thus obtained (M=287.29 g).

The corresponding yield is quantitative.

Stage D 49.76 g of the acid obtained in Stage C and then 57 ml of SOCl$_2$ are introduced into a round-bottomed flask equipped with magnetic stirring, a condenser and a sodium chloride tube.

The medium is heated to 70° C. and kept at this temperature for 4 hours.

The medium is evaporated to dryness under reduced pressure.

44.5 g of methyl 2,5-dioxo-alpha-(2-thienyl)-3-oxazolidineacetate having the empirical formula C$_{10}$H$_9$NO$_5$S are thus obtained (M=255.25 g). The yield is quantitative.

Stage E 44.5 g of the product obtained in Stage D and 500 ml of dichloromethane are introduced into a round-bottomed flask placed under a nitrogen atmosphere.

92.3 g of aluminum chloride are then added.

The medium is kept stirred overnight at 20° C., and then diluted with dichloromethane and brought to pH 8-9 by addition of a tartaric acid and aqueous ammonia solution while cooling. The medium is next diluted with 1 l of water and 1 l of dichloromethane.

The medium is separated by decantation, extracted several times with dichloromethane, and the organic phases are combined and they are dried over sodium sulfate.

The solvent is then evaporated off under reduced pressure.

32.5 g of methyl 4-oxo-4,5,6,7-tetrahydrothieno[2,3-c]pyridine-7-carboxylate having the empirical formula $C_9H_9NO_3S$ are thus obtained (M=211.24 g).

The corresponding yield is 88%.

Stage F 30 g of the product obtained in Stage E and 360 ml of THF are introduced into a round-bottomed flask.

The medium is cooled to 0° C., and then 93 g of $(BOC)_2O$ are added and the reaction is allowed to proceed for 2 hours 30 minutes at 20° C.

The medium is then diluted with AcOEt, washed with an aqueous tartaric acid solution at 10%, and then with demineralized water.

The organic phase is then dried over magnesium sulfate.

The solvent is evaporated off under reduced pressure and the medium is then purified by chromatography on silica.

27.91 g of 6-(1,1-dimethylethyl) and 7-methyl 4,5-dihydro-4-oxothieno[2,3-c]pyridine-6(7H),7-dicarboxylate having the empirical formula $C_{14}H_{17}NO_5S$ are thus obtained (M=311.36 g).

The corresponding yield is 63%.

Stage G 50 g of the product obtained in Stage F (67.1 mmol) and 1500 ml of methanol are introduced into a round-bottomed flask placed under a nitrogen atmosphere and cooled by an ice bath. 1.6 g of NaBH4 are next added. The medium is stirred while allowing the temperature to return to 20° C. over 30 minutes. The medium is next diluted with 225 ml of dichloromethane, washed with an aqueous tartaric acid solution at 10%, and then with demineralized water, and the organic phase is dried over sodium sulfate. The solvent is evaporated off under reduced pressure. 51.4 g of 6-(1,1-dimethylethyl) and 7-methyl-4,7-dihydro-4-hydroxythieno[2,3-c]pyridine-6,7(5H)-dicarboxylate having the empirical formula $C_{14}H_{15}NO_5S$ are obtained (M=313.38 g).

Stage H 59.7 g of the product obtained in Stage G and 583 ml of dichloromethane are introduced into a round-bottomed flask placed under an argon atmosphere.

The medium is cooled to around 0-5° C., and then 39.3 ml of TEA and 48.7 g of $(CH_3SO_2)_2O$ are successively added. The temperature is allowed to return to 20° C. and the medium is kept stirred for 1 h 20 min at 20° C.

The medium is diluted with dichloromethane, and then washed with an aqueous tartaric acid solution at 10% and with demineralized water. The organic phase is dried over sodium sulfate.

The solvent is next evaporated under reduced pressure. 68.9 g of benzyl-O—NH2 are then added, and the medium is left in contact at 0-5° C. for 72 hours.

The medium is next diluted with dichloromethane and washed with an aqueous tartaric acid solution at 10% and then with demineralized water.

The organic phase is dried over sodium sulfate and the solvent is evaporated off under reduced pressure.

The dry extract obtained is purified by chromatography on silica, eluting with a dichloromethane/AcOEt 98/2 mixture.

47.0 g of 6-(1,1-dimethylethyl) and 7-methyl 4,7-dihydro-4-[(phenylmethoxy)amino]thieno[2,3-c]pyridine-6,7(5H)-dicarboxylate having the empirical formula $C_{21}H_{26}O_5N_2S$ are obtained (M=418.515 g).

The corresponding yield is 60.2%.

Stage I

47 μg of the product obtained in Stage H are dissolved in 79 ml of AcOEt and the medium is cooled to 0° C.

261 ml of a saturated solution of gaseous HCl in acetate are added. The medium is left in contact for 1 hour at 20° C.

The solvent is evaporated off under reduced pressure and then the product is crystallized from ethyl ether.

44.12 g of methyl 4,5,6,7-tetrahydro-4-[phenylmethoxy)amino]thieno[2,3-c]pyridine-7-carboxylate hydrochloride having the empirical formula $C_{16}H_{20}N_2O_3S_2Cl_2$ are obtained (M=391.318 g).

Stage J 44.1 g of the product obtained in Stage I are suspended in 1000 ml of dichloromethane. 35 ml of a concentrated solution of aqueous ammonia are added. The medium is separated by decantation, washed with demineralized water and the organic phase is dried over sodium sulfate. The solvent is then separated off under reduced pressure.

34.6 g of methyl 4,5,6,7-tetrahydro-4-[(phenylmethoxy)amino]thieno[2,3-c]pyridine-7-carboxylate having the empirical formula $C_{16}H_{18}N_2O_3S$ are obtained (M=318.4 g).

The corresponding yield is 96.7%.

Stage K 34.1 g of the product obtained in Stage J, 8.8 l of acetonitrile and 30.8 ml of TEA are introduced into a round-bottomed flask placed under an argon atmosphere and cooled by an ice bath.

The medium is stirred for 2 minutes and 6.5 ml of diphosgene are then introduced therein.

The solution is stirred at 20° C. for 1 hour.

The medium is diluted with AcOEt and washed with a tartaric acid solution at 10% and then with water.

The organic phase is dried over magnesium sulfate and the solvent is evaporated off under reduced pressure.

The crude product is dissolved in 1000 ml of dichloromethane with 1.2 ml of DBU. After 10 minutes of contact, the reaction mixture is washed with a tartaric acid solution at 10% and then with water. After evaporation of the solvent under reduced pressure, a crude product is obtained which is purified by chromatography to give 37.2 g of methyl trans 4,5,6,8-tetrahydro-6-oxo-5-(phenylmethoxy)-4,7-methano-7H-thieno[2,3-e][1,3]diazepine-8-carboxylate having the empirical formula $C_{17}H_{16}N_2O_4S$ (M=344.39 g).

The corresponding yield is 80%.

Stage L 211 mg of the product obtained in the preceding stage are dissolved in 2.2 ml of acetic acid, in a round-bottomed flask placed under an argon atmosphere, and 1.7 ml of water are then slowly added. The medium is cooled to 3° C. and then 31.5 μl of bromine in solution in 0.85 ml of acetic acid are slowly added. The medium is stirred for 45 minutes until a large amount of cream-colored precipitate appears. The suspension is next introduced into 20 ml of a 0.5 N aqueous sodium thiosulfate solution. The medium is extracted with ethyl acetate and the organic phase is washed several times with a saturated aqueous sodium bicarbonate solution and then with a saturated aqueous sodium chloride solution. The organic phase is dried over $MgSO_4$, filtered and the solvent is evaporated under reduced pressure. 293 mg of crude product are obtained, which are purified by chromatography on a silica column, eluting with a methylene chloride/ethyl acetate/triethylamine 95/5/0.5 mixture. After evaporation of the solvent, 222 mg of compound methyl trans-2-bromo-4,5,6,8-tetrahydro-6-oxo-5-(phenylmethoxy)-4,7-methano-7H-thieno[2,3-e][1,3]diazepine-8-carboxylate having the empirical formula $C_{17}H_{15}BrN_2O_4S$ are obtained (M=423.29 g).

The corresponding yield is 85.6%.

Stage M 226 mg of the product obtained in the preceding stage are dissolved in 11.5 ml of toluene degassed beforehand by bubbling argon through, in a round-bottomed flask placed under an argon atmosphere. 112 mg of 4-fluorophenylboronic acid are next added, followed by 54 mg of Pd(PPh$_3$)$_4$. 2.17 ml of a 2 N aqueous Na$_2$CO$_3$ solution are next added. The solution is next heated under reflux for 4 h 30 min. The reaction medium is cooled and it is poured into water and then extracted with ethyl acetate. The organic phase is washed with a saturated aqueous sodium chloride solution and dried over magnesium sulfate. The solvent is evaporated under reduced pressure and 126.1 mg of crude product are obtained, which product is purified by chromatography on silica, eluting with a methylene chloride/ethyl acetate/triethylamine, 96/4/0.1%, mixture. After evaporation of the solvent, 211 mg of compound methyl trans-2-(4-fluorophenyl)-4,5,6,8-tetrahydro-6-oxo-5-(phenylmethoxy)-4,7-methano-7H-thieno[2,3-e][1,3]diazepine-8-carboxylate having the empirical formula C$_{23}$H$_{19}$FN$_2$O$_4$S are obtained (M=438.48 g).

The corresponding yield is 90%.

Stage N 221.5 mg of the product obtained in the preceding stage are dissolved in 26.6 ml of ethanol, in a round-bottomed flask. 221.5 mg of 10% palladium on carbon are added and the medium is purged under vacuum and saturated with hydrogen. After stirring for 1 h 45 min, the catalyst is filtered off and then the solvent is evaporated off under reduced pressure. After evaporation of the solvent, 163.5 mg are obtained in the form of cream-colored crystals of the compound methyl trans-2-(4-fluorophenyl)-4,5,6,8-tetrahydro-5-hydroxy-6-oxo-4,7-methano-7H-thieno[2,3-e][1,3]diazepine-8-carboxylate having the empirical formula C$_{16}$H$_{13}$FN$_2$O$_4$S (M=348.35 g).

The corresponding yield is 93%.

Stage O 176.4 mg of the product obtained in the preceding stage are dissolved in 2 ml of pyridine, in a round-bottomed flask. 241 mg of the pyridine-SO$_3$ complex are then introduced therein and the medium is stirred at room temperature for 16 h 30 min. The yellow solution obtained is purified by chromatography on silica, eluting with a methylene chloride/methanol 90/10 mixture. After evaporation of the fractions, 554.5 mg of compound pyridinium salt of methyl trans-2-(4-fluorophenyl)-4,5,6,8-tetrahydro-6-oxo-5-(sulfoxy)-4,7-methano-7H-thieno[2,3-e][1,3]diazepine-8-carboxylate having the empirical formula C$_{21}$H$_{18}$FN$_3$O$_7$N$_2$ are obtained (M=507.51 g).

The crude product is purified after converting to the sodium salt.

Stage P

The salt exchange is carried out by passing 554.5 mg of the pyridinium salt obtained in the preceding stage over 58 g of Dowex resin prepared beforehand with a 2 N aqueous sodium hydroxide solution. The product deposited on the Dowex resin column is eluted with water containing 10% THF. After combining the fractions and evaporating the solvent under reduced pressure, lyophilization is carried out and 332.8 mg are obtained, which product is purified by impasting in methanol and then in ethyl ether. 175.2 mg of compound sodium salt of methyl trans-2-(4-fluorophenyl)-4,5,6,8-tetrahydro-6-oxo-5-(sulfoxy)-4,7-methano-7H-thieno[2,3-e][1,3]diazepine-8-carboxylate having the empirical formula C$_{16}$H$_{12}$FO$_7$N$_2$S$_2$,Na are finally obtained (M=450.40 g).

The corresponding yield is 79%.

NMR spectrum, D$_2$O to 300 MHz, chemical shift and multiplicity:

3.89 (s): CH$_3$—O—CO; 5.49 (s): CH$_3$—O—CO—CHN 3.52 (t) and 3.79 (broad d): N—CH$_2$—CH—N; 4.89 (broad s): N—CH$_2$—CH—N; 7.11 and 7.51: aromatic H; 7.23 (s): CH=C=S.

LC/MS (negative electrospray), m/z: M$^-$=427 and (2M+Na)$^-$=877.

Example 20

Sodium Salt of Trans-4,5,6,8-tetrahydro-6-oxo-2-(3-pyridinyl)-5-(sulfoxy)-4,7-methano-7H-thieno[2,3-e][1,3]diazepine-8-carboxamide Stage A The procedure is carried out as in Stage A of Example 7 with 2.5 g of the product obtained in Stage L of Example 19, 11.2 ml of dioxane, 11.2 ml of water, 5.95 ml of 1 N aqueous sodium hydroxide. 1.82 g of compound trans-2-bromo-4,5,6,8-tetrahydro-6-oxo-5-(phenylmethoxy)-4,7-methano-7H-thieno[2,3-e][1,3]diazepine-8-carboxylic acid having the empirical formula C$_{16}$H$_{13}$BrO$_4$N$_2$S are obtained (M=409.27 g).

The corresponding yield is 75.7%.

Stage B

The procedure is carried out as in Stage B of Example 7 with 1.82 g of the product obtained in the preceding stage, 21 ml of DMF, 2.95 g of BOP, 0.9 g of HOBT, 476.5 mg of NH$_4$Cl, 3.1 ml of DIPEA. 870 mg of the compound trans-2-bromo-4,5,6,8-tetrahydro-6-oxo-5-(phenylmethoxy)-4,7-methano-7H-thieno [2,3-e][1,3] diazepine-8-carboxamide having the empirical formula C$_{16}$H$_{14}$BrN$_3$O$_3$S are obtained (M=408.28 g).

The corresponding yield is 48%.

Stage C 305.5 mg of product obtained in the preceding stage are dissolved in 24 ml of 1,4-dioxane, in a round-bottomed flask placed under an argon atmosphere, and then 413 mg of 3-tri-N-butylstanylpyridine and 86.4 mg of Pd(PPh$_3$)$_4$ are added to the solution. The solution is heated at 100° C. for 6 hours and then 86.4 mg of Pd(PPh$_3$)$_4$ are again added. The medium is again stirred at 100° C. for 17 hours, the solvent is evaporated off under reduced pressure. The dry extract is taken up in 50 ml of ethyl acetate to which 50 ml of an aqueous KF solution are added. The aqueous phase is again extracted with ethyl acetate and washed with a saturated aqueous sodium chloride solution, the organic phases are combined, dried over magnesium sulfate and the solvent is evaporated off under reduced pressure. 590 mg of crude product are obtained, which product is purified by chromatography on a silica column, eluting with a methylene chloride/methanol/triethylamine, 95/5/0.1%, mixture. 92.4 mg of compound trans-4,5,6,8-tetrahydro-6-oxo-5-(phenylmethoxy)-2-(3-pyridinyl)-4,7-methano-7H-thieno[2,3-e][1,3]diazepine-8-carboxamide having the empirical formula C$_{21}$H$_{18}$O$_3$N$_4$S are obtained (M=406.47 g).

The corresponding yield is 30%.

Stage D

The procedure is carried out as in Stage M of Example 1 with 55 mg of the product obtained in the preceding stage, 15 ml of ethanol and 55 mg of palladium on carbon in the presence of hydrogen. 26 mg of compound trans-4,5,6,8-tetrahydro-5-hydroxy-6-oxo-2-(3-pyridinyl)-4,7-methano-7H-thieno[2,3-e][1,3]diazepine-8-carboxamide having the empirical formula C$_{14}$H$_{12}$O$_3$N$_4$S are obtained (M=316.34 g).

The corresponding yield is 62%.

Stage E

The procedure is carried out as in Stage N of Example 1 with 26.6 mg of the product obtained in the preceding stage, 0.34 ml of pyridine and 40.1 mg of the pyridine-SO$_3$ complex. 71.5 mg are obtained in the form of a yellow oil of the compound pyridinium salt of trans-4,5,6,8-tetrahydro-6-oxo-2-(3-pyridinyl)-5-(sulfoxy)-4,7-methano-7H-thieno[2,3-e][1,3]diazepine-8-carboxamide having the empirical formula $C_{19}H_{17}O_6N_5S_2$ (M=475.05 g).

Stage F

The procedure is carried out as in Stage R of Example 12 with 10 g of Dowex resin, 71.5 mg of the product obtained in the preceding stage and 0.5 ml of water at 10% in THF. 26.4 g are obtained in the form of a cream-colored powder of the compound sodium salt of trans-4,5,6,8-tetrahydro-6-oxo-2-(3-pyridinyl)-5-(sulfoxy)-4,7-methano-7H-thieno[2,3-e][1,3]diazepine-8-carboxamide having the empirical formula $C_{14}H_{11}O_6N_4S_2$,Na (M=418.38 g).

The corresponding yield is 75%.

Example 21

Sodium Salt of Methyl Trans-2-(aminocarbonyl)-4,5,6,8-tetrahydro-6-oxo-5-(sulfoxy)-4,7-methano-7H-thieno[2,3-e][1,3]diazepine-8-carboxylate.

Stage A 1 g of the product in Stage L of Example 19 is dissolved in 80 ml of toluene degassed beforehand by bubbling argon through, in a round-bottomed flask placed under an argon atmosphere. 1.12 g of vinyltributylstanone are next added, followed by 272 mg of Pd(PPh$_3$)$_4$. The suspension is heated to 100° C. and stirred for one hour. After stirring for 40 minutes, the reaction medium is cooled to room temperature and the solvent is evaporated off under reduced pressure. The residue is taken up in 120 ml of ethyl acetate and 120 ml of an aqueous KF solution. After extraction, the organic phase is washed with a saturated aqueous sodium chloride solution, and then dried over magnesium sulfate and the solvent is evaporated off under reduced pressure. 1.67 g of crude product are obtained, which product is purified by chromatography on silica, eluting with a methylene chloride/ethyl acetate/triethylamine 95/5/0.1% mixture. 405.7 mg of compound methyl trans-2-ethenyl-4,5,6,8-tetrahydro-6-oxo-5-(phenylmethoxy)-4,7-methano-7H-thieno[2,3-e][1,3]diazepine-8-carboxylate having the empirical formula $C_{19}H_{18}N_2O_4S$ are obtained (M=370.43 g).

The corresponding yield is 46%.

Stage B 513 mg of the product obtained in the preceding stage, 8.2 ml of THF, 4.1 ml of water and 8.2 ml of tert-butanol are dissolved in a round-bottomed flask. 220 μl of OSO$_4$ in solution at 5% in water and 888 mg of NaIO$_4$ are added to the solution obtained above. A suspension is obtained which is stirred at room temperature for 1 hour. The reaction medium is then poured into water and extracted with ethyl acetate. The organic phase is washed with water and then with a saturated aqueous sodium chloride solution and dried over magnesium sulfate. After evaporation of the solvents under reduced pressure, 534.6 mg of crude product are obtained, which product is purified by chromatography on a silica column, eluting with a methylene chloride/ethyl acetate/triethylamine, 90/10/0.1%, mixture. 286.6 mg of compound methyl trans-2-formyl-4,5,6,8-tetrahydro-6-oxo-5-(phenylmethoxy)-4,7-methano-7H-thieno[2,3-e][1,3]diazepine-8-carboxylate having the empirical formula $C_{18}H_{16}N_2O_5S$ are obtained (M=372.40 g).

The corresponding yield is 55.5%

Stage C 297 mg of the product obtained in the preceding stage are dissolved in 30 ml of acetone. 189 mg of powdered KMnO$_4$ are next added followed by 30 ml of water. The suspension is stirred at room temperature for 1 h 30 min, and then 30 ml of acetone are added and the suspension is again stirred for 30 minutes. After evaporation of the acetone under reduced pressure, the reaction medium is diluted with water and acidified with 2 ml of a 1 N aqueous HCl solution. The medium is extracted with ethyl acetate and the organic phase is washed with a saturated aqueous sodium chloride solution. The organic phase is dried over magnesium sulfate and the solvent is evaporated off under reduced pressure. 311.8 mg of compound 8-methyl trans-4,5,6,8-tetrahydro-6-oxo-5-(phenylmethoxy)-4,7-methano-7H-thieno[2,3-e][1,3]diazepine-2,8-dicarboxylate having the empirical formula $C_{18}H_{16}N_2O_6S$ are obtained (M=388.40 g).

The yield is quantitative.

Stage D

The procedure is carried out as in Stage B of Example 7 with 69 mg of the product obtained in the preceding stage, 0.84 ml of DMF, 117.8 mg of BOP, 36 mg of HOBT, 19 mg of NH$_4$Cl and 0.124 ml of DIPEA. 44.6 mg of a compound methyl trans-2-(aminocarbonyl)-4,5,6,8-tetrahydro-6-oxo-5-(phenylmethoxy)-4,7-methano-7H-thieno[2,3-e][1,3]diazepine-8-carboxylate having the empirical formula $C_{18}H_{17}N_5O_3S$ are obtained (M=387.41 g).

The corresponding yield is 64.8%.

Stage E

The procedure is carried out as in Stage M of Example 1 with 44.6 mg of the product obtained in the preceding stage, 4.5 ml of ethanol and 44.6 mg of 10% palladium on carbon catalyst. 24.3 mg of compound methyl trans-2-(aminocarbonyl)-4,5,6,8-tetrahydro-5-hydroxy-6-oxo-4,7-methano-7H-thieno[2,3-e][1,3]diazepine-8-carboxylate having the empirical formula $C_{11}H_{11}O_5N_3S$ are obtained (M=297.29 g).

The corresponding yield is 71%.

Stage F

The procedure is carried out as in Stage M of Example 1 with 24.3 mg of the product obtained in the preceding stage, 0.32 ml of pyridine and 39 mg of the pyridine-SO$_3$ complex. 74.6 mg of the compound pyridinium salt of methyl trans-2-(aminocarbonyl)-4,5,6,8-tetrahydro-6-oxo-5-(sulfoxy)-4,7-methano-7H-thieno[2,3-e][1,3]diazepine-8-carboxylate having the empirical formula $C_{16}H_{16}O_8N_4S_2$ are obtained (M=456.45 g).

The crude product is next converted to a sodium salt.

Stage G

The procedure is carried out as in Stage R of Example 12 with 74.6 mg of the product obtained in the preceding stage, 10 g of Dowex resin. 19.9 mg of compound sodium salt of methyl trans-2-(aminocarbonyl)-4,5,6,8-tetrahydro-6-oxo-5-(sulfoxy)-4,7-methano-7H-thieno[2,3-e][1,3]diazepine-8-carboxylate having the empirical formula $C_{11}H_{10}O_8N_3S_2$,Na are obtained (M=399.34 g).

The corresponding yield is 61%.

LC/MS (negative electrospray), m/z: M$^-$=376.

Proton NMR, D$_2$O at 300 MHz, chemical shift and multiplicity:

3.63 (d) and 3.82 (dd) and 3.66 (d) and 3.98 (dd): N—CH$_2$—CH; 4.95 (d) and 5.01 (d): N—CH$_2$—CH; 5.64 (s): CH═C—O—OCH$_3$; 7.67 (s) and 7.70 (s): H of the furan; 3.91 (s), 3.93 (s): CH$_3$—O—CO.

Example 22

Sodium Salt of Methyl Trans-4,5,6,8-tetrahydro-6-oxo-2-[[[2-(4-pyridinyl)ethyl]amino]carbonyl]-5-(sulfoxy)-4,7-methano-7H-thieno[2,3-e][1,3]diazepine-8-carboxylate Stage A The procedure is carried out as in Stage B of Example 7 with 196 mg of the product obtained in Stage C of Example 21, 2.24 ml of DMF, 335 mg of BOP, 102 mg of HOBT, 123 g of 4,2-aminoethylpyridine and 176 µl of DIPEA. 203 mg of product methyl trans-4,5,6,8-tetrahydro-6-oxo-5-(phenylmethoxy)-2-[[[2-(4-pyridinyl)ethyl]amino]carbonyl]-4,7-methano-7H-thieno[2,3-e][1,3]diazepine-8-carboxylate having the empirical formula $C_{25}H_{24}O_5N_4S$ are obtained (M=492.56 g).

The corresponding yield is 70.7%.

Stage B

The procedure is carried out as in Stage M of Example 1 with 50 mg of product obtained in the preceding stage, 4.5 ml of ethanol, 50 mg of 10% palladium on carbon. 36.8 mg of compound methyl trans-4,5,6,8-tetrahydro-5-hydroxy-6-oxo-2-[[[2-(4-pyridinyl)ethyl]amino]carbonyl]-4,7-methano-7H-thieno[2,3-e][1,3]diazepine-8-carboxylate having the empirical formula $C_{18}H_{18}O_5N_4S$ are obtained (M=402.43 g).

The corresponding yield is 98%.

Stage C

The procedure is carried out as in Stage M of Example 1 with 36.8 mg of the product obtained in the preceding stage, 0.36 ml of pyridine and 43.7 mg of pyridine-$SO_3$ complex. 93.7 mg of compound pyridinium salt of methyl trans-4,5,6,8-tetrahydro-6-oxo-2-[[[2-(4-pyridinyl)ethyl]amino]carbonyl]-5-(sulfoxy)-4,7-methano-7H-thieno[2,3-e][1,3]diazepine-8-carboxylate having the empirical formula $C_{25}H_{23}O_8N_5S_2$ are obtained (M=561.59 g).

The crude product is next converted to a sodium salt.

Stage D

The procedure is carried out as in Stage R of Example 12 with 93.7 mg of the product obtained in the preceding stage, 11 g of Dowex resin. The lyophilizate is obtained after passing over a Dowex resin and dissolved in 1 ml of water and then attached to a column of 54 ml of DIAION HP20 resin. The product is successively eluted with a water/acetone 95/5 mixture, and then with an acetone/water 10/90, and acetone/water 20/80 mixture. After evaporation of the fractions obtained in the acetone/water 20/80 elution, 12.2 mg of compound sodium salt of methyl trans-4,5,6,8-tetrahydro-6-oxo-2-[[[2-(4-pyridinyl)ethyl]amino]carbonyl]-5-(sulfoxy)-4,7-methano-7H-thieno[2,3-e][1,3]diazepine-8-carboxylate having the empirical formula $C_{18}H_{17}O_8N_4S_2$,Na are obtained (M=504.48 g).

The corresponding yield is 23%.

LC/MS (negative electrospray) m/z: M-=481

Example 23

Sodium Salt of 4,5,6,8-tetrahydro-6-oxo-$N^{2-}$-[2-(4-pyridinyl)ethyl]-5-(sulfoxy)-4,7-methano-7H-thieno[2,3-e][1,3]diazepine-2,8-dicarboxamide Stage A The procedure is carried out as in Stage A of Example 7 with 126 mg of the product obtained in Stage A of Example 22, 1.74 ml of dioxane, 0.64 ml of water and 281 µl of 1 N aqueous sodium hydroxide. 124 mg of compound trans-4,5,6,8-tetrahydro-6-oxo-5-(phenylmethoxy)-2-[[[2-(4-pyridinyl)ethyl]amino]carbonyl]-4,7-methano-7H-thieno[2,3-e][1,3]diazepine-8-carboxylic acid having the empirical formula $C_{24}H_{22}O_5N_4S$ are obtained (M=478.53 g).

The corresponding yield is quantitative.

Stage B

The procedure is carried out as in Stage B of Example 7 with 124 mg of the product obtained in the preceding stage, 162 mg of BOP, 51.8 mg of HOBT, 27.4 mg of $NH_4Cl$, 178 µl of DIPEA. 35.8 mg of compound trans-4,5,6,8-tetrahydro-6-oxo-5-(phenylmethoxy)-$N^2$-[2-(4-pyridinyl)ethyl]-4,7-methano-7H-thieno[2,3-e][1,3]diazepine-2,8-dicarboxamide having the empirical formula $C_{24}H_{23}O_4N_5S$ are obtained (M=477.55 g).

The corresponding yield is 29.3%.

Stage C

The procedure is carried out as in Stage M of Example 1 with 36.4 mg of the product obtained in the preceding stage, 4 ml of absolute ethanol, 72.8 mg of palladium on carbon. 19.6 mg of compound trans-4,5,6,8-tetrahydro-5-hydroxy-6-oxo-$N^2$-[2-(4-pyridinyl)ethyl]-4,7-methano-7H-thieno[2,3-e][1,3]diazepine-2,8-dicarboxamide having the empirical formula $C_{17}H_{17}O_4N_5S$ are obtained (M=396.42 g).

The crude product is used without purification in the next stage.

Stage D

The procedure is carried out as in Stage M of Example 1 with 19.6 mg of the product obtained in the preceding stage, 0.20 ml of pyridine and 24 g of pyridine-$SO_3$ complex. 53.6 mg of the compound pyridinium salt of 4,5,6,8-tetrahydro-6-oxo-$N^2$-[2-(4-pyridinyl)ethyl]-5-(sulfoxy)-4,7-methano-7H-thieno[2,3-e][1,3]diazepine-2,8-dicarboxamide having the empirical formula $C_{22}H_{22}O_7N_6S_2$ are obtained (M=546.58 g).

The crude product is converted to a sodium salt.

Stage E

The procedure is carried out as in Stage R of Example 4 with 53.8 mg of the product obtained in the preceding stage, and 6.02 g of Dowex resin. The lyophilizate obtained is purified on DIAION HP20 resin and 3.3 mg of the compound sodium salt of 4,5,6,8-tetrahydro-6-oxo-$N^2$-[2-(4-pyridinyl)ethyl]-5-(sulfoxy)-4,7-methano-7H-thieno[2,3-e][1,3]diazepine-2,8-dicarboxamide having the empirical formula $C_{17}H_{16}O_7N_5S_2$ are obtained (M=489.46 g).

The corresponding yield is 13.3%.

LC/MS (negative electrospray): m/z: M-=466

Example 24

Sodium Salt of Trans-4,5,6,8-tetrahydro-2-(2-methylphenyl)-6-oxo-5-(sulfoxy)-4,7-methano-7H-thieno[2,3-e][1,3]diazepine-8-carboxamide Stage A 5.09 g of methyl 4,5,6,8-tetrahydro-6-oxo-5-(phenylmethoxy)-4,7-methano-7H-thieno[2,3-e][1,3]diazepine-8-carboxylate prepared in Stage K of Example 19 are dissolved under argon in 100 ml of $CCl_4$, in a 60 ml round-bottomed flask provided with magnetic stirring, the medium is cooled on an ice bath, and then 1.87 g (7.4 mmol) of iodine and 3.813 g of $PhI(OCOCF_3)_2$ are added. The temperature is allowed to return to 20° C. After stirring for 2 to 3 h at 20° C., the solution is poured into a 0.5 N aqueous sodium thiosulfate solution, the medium is extracted with ethyl acetate, and then washed again with a 0.5 N aqueous sodium thiosulfate solution, washed with a saturated aqueous sodium chloride solution, and then with a phosphate buffer solution, pH=7.0, and finally with a saturated aqueous sodium chloride solution. After drying over $MgSO_4$ and evaporation of the solvent under reduced pressure, the crude product is obtained which is purified by chromatography on silica, eluting with a $CH_2Cl_2$/ethyl acetate (95/5) mixture, TEA=0.1%.

4.88 g of methyl 4,5,6,8-tetrahydro-2-iodo-6-oxo-5-(phenylmethoxy)-4,7-methano-7H-thieno[2,3-e][1,3]diazepine-8-carboxylate having the empirical formula $C_{17}H_{15}N_2IO_4S$ are obtained (M=470.29 g).

The yield is 70%.

Stage B

The procedure is carried out as in Stage M of Example 19 with 250 mg of the product obtained in the preceding stage, 11.5 ml of toluene, 108.4 mg of 2-methylphenylboronic acid, 61.43 mg of $Pd(PPh_3)_4$ and 2.15 ml of a 2 N aqueous $Na_2CO_3$ solution. 229 mg of the compound methyl trans-4,5,6,8-tetrahydro-2-(2-methylphenyl)-6-oxo-5-(phenylmethoxy)-4,7-methano-7H-thieno[2,3-e][1,3]diazepine-8-carboxylate having the empirical formula $C_{24}H_{22}N_2O_4S$ are obtained (M=434.52 g).

The corresponding yield is 99%.

Stage C

The procedure is carried out as in Stage A of Example 7 with 265.4 mg of product obtained in the preceding stage, 3.5 ml of dioxane, 1.45 ml of water and 0.64 ml of 1 N aqueous sodium hydroxide. 235.5 mg of compound trans-4,5,6,8-tetrahydro-2-(2-methylphenyl)-6-oxo-5-(phenylmethoxy)-4,7-methano-7H-thieno[2,3-e][1,3]diazepine-8-carboxylic acid having the empirical formula $C_{23}H_{20}N_2O_4S$ are obtained (M=420.49 g).

The corresponding yield is 92%.

Stage D

The procedure is carried out as in Stage B of Example 7 with 232 mg of product obtained in the preceding stage, 3 ml of DMS, 365 mg of BOP, 111.6 mg of HOBT, 59 mg of $NH_4Cl$, 383 µl of DIPEA. 196.1 mg of compound trans-4,5,6,8-tetrahydro-2-(2-methylphenyl)-6-oxo-5-(phenylmethoxy)-4,7-methano-7H-thieno[2,3-e][1,3]diazepine-8-carboxamide having the empirical formula $C_{23}H_{21}N_3O_3S$ are obtained (M=420.49 g).

The corresponding yield is 85%.

Stage E

The procedure is carried out as in Stage M of Example 1 with 177 mg of the product obtained in the preceding stage, 35 ml of ethanol, 17 ml of THF and 177 mg of 30% palladium on carbon. 123 mg of the compound trans-4,5,6,8-tetrahydro-5-hydroxy-2-(2-methylphenyl)-6-oxo-4,7-methano-7H-thieno[2,3-e][1,3]diazepine-8-carboxamide having the empirical formula $C_{16}H_{15}N_3O_3S$ are obtained (M=329.38 g).

The corresponding yield is 83%.

Stage F

The procedure is carried out as in Stage N of Example 1 with 123 mg of product obtained in the preceding stage, 2 ml of pyridine, 174 mg of $SO_3$-pyridine complex. 100 mg of compound triethylammonium salt of trans-4,5,6,8-tetrahydro-2-(2-methylphenyl)-6-oxo-5-(sulfoxy)-4,7-methano-7H-thieno[2,3-e][1,3]diazepine-8-carboxamide having the empirical formula $C_{22}H_{30}O_6N_4S_2$ are obtained (M=510.63 g).

The corresponding yield is 52.4%.

Stage G

The procedure is carried out as in Stage R of Example 12 with 100 mg of the product obtained in the preceding stage and 30 g of Dowex resin. 76.8 mg of compound sodium salt of trans-4,5,6,8-tetrahydro-2-(2-methylphenyl)-6-oxo-5-(sulfoxy)-4,7-methano-7H-thieno[2,3-e][1,3]diazepine-8-carboxamide having the empirical formula $C_{16}H_{14}O_6N_3S_2$,Na are obtained (M=431.42 g).

The corresponding yield is 90%.

LC/MS (negative electrospray) $M^-$=408.2 g; $(2M+Na)^-$=839.

Proton NMR, $D_2O$, 300 MHz, chemical shift and multiplicity:

2.41 (s): $CH_3$—ϕ; 3.50 (d), 3.83 (dd): N—$CH_2$—CH; 4.95 (d): N—$CH_2$—CH; 5.38 (s): CH—CO—N; 7.15 (s): SC=CH; 7.26 to 7.50 (m): aromatic H.

Example 25

Sodium Salt of Trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide Stage A The procedure is carried out as in Stage M of Example 19 with 250 mg of the product obtained in Stage A of Example 24, 11 ml of toluene, 151 mg of 2-(trifluoromethyl)phenylboronic acid, 61 mg of $Pd(PPh_3)_4$, and 2.15 ml of a 2 M aqueous $Na_2CO_3$ solution. 199 mg of compound methyl trans-4,5,6,8-tetrahydro-6-oxo-5-(phenylmethoxy)-2-[2-(trifluoromethyl)phenyl]-4,7-methano-7H-thieno[2,3-e][1,3]diazepine-8-carboxylate having the empirical formula $C_{24}H_{19}N_2O_4SF_3$ are obtained (M=488.49 g).

The corresponding yield is 76.5%.

Stage B

The procedure is carried out as in Stage A of Example 7 with 230 mg of the product obtained in the preceding stage, 5 ml of dioxane, 1.45 ml of water, and 0.5 ml of 1 N aqueous sodium hydroxide. 199 mg of compound trans-4,5,6,8-tetrahydro-6-oxo-5-(phenylmethoxy)-2-[2-(trifluoromethyl)phenyl]-4,7-methano-7H-thieno[2,3-e][1,3]diazepine-8-carboxylic acid having the empirical formula $C_{23}H_{17}N_2O_4SF_3$ are obtained (M=474.46 g).

The corresponding yield is 89.2%.

Stage C

The procedure is carried out as in Stage B of Example 7 with 196.2 mg of the product obtained in the preceding stage, 2.5 ml of DMF, 274.3 mg of BOP, 83.8 mg of HOBT, 44.2 mg of $NH_4Cl$, and 288 µl of DIPEA. 99.1 mg of compound trans-4,5,6,8-tetrahydro-6-oxo-5-(phenylmethoxy)-2-[2-(trifluoromethyl)phenyl]-4,7-methano-7H-thieno[2,3-e][1,3]diazepine-8-carboxamide having the empirical formula $C_{23}H_{18}N_3O_3SF_3$ are obtained (M=473.48 g).

The corresponding yield is 50.6%.

Stage D

The procedure is carried out as in Stage M of Example 1 with 84.3 mg of the product obtained in the preceding stage, 16.8 ml of methanol, 8.4 ml of THF, and 84.3 mg of 30% palladium on carbon. 74.7 mg of the compound trans-4,5,6,8-tetrahydro-5-hydroxy-6-oxo-2-[2-(trifluoromethyl)phenyl]-4,7-methano-7H-thieno[2,3-e][1,3]diazepine-8-carboxamide having the empirical formula $C_{16}H_{22}N_3O_3SF_3$ are obtained (M=383.35 g).

The corresponding yield is 98%.

Stage E

The procedure is carried out as in Stage M of Example 1 with 74.7 mg of product obtained in the preceding stage, 1 ml of pyridine and 92.8 mg of pyridine-$SO_3$ complex. Purification on silica of the crude product is carried out as in Stage M of Example 1, eluting with a methylene chloride/ethanol/ triethylamine 60/40/0.5 mixture. 73.5 mg of compound triethylammonium salt of trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide having the empirical formula $C_{22}H_{27}O_6N_4S_2F_3$ are obtained (M=564.61 g).

The corresponding yield is 66.8%.

Stage F

The procedure is carried out as in Stage R of Example 12 with 73.5 mg of the product obtained in the preceding stage, and 20 g of Dowex resin. Elution is carried out with water containing 20% of THF and 35.2 mg of the compound sodium salt of trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide having the empirical formula $C_{16}H_{11}O_6N_3S_2F_3Na$ are obtained (M=485.99 g).

The corresponding yield is 55.6%.

LC/MS (negative electrospray), $M^-$=462; $(2M+Na)^-$=947.

Proton NMR, $D_2O$, 300 MHz, chemical shift and multiplicity:

3.52 (broad d) and 3.85 (dd): N—$CH_2$—CH; 4.44 (d): N—$CH_2$—CH; 5.39 (s): CH—CO—N; 7.18 (s): S—C=CH; 7.54 to 7.72 (m) and 7.87 (broad d): aromatic H.

Example 26

Sodium Salt of Trans-2-(2-ethylphenyl)-4,5,6,8-tetrahydro-6-oxo-5-(sulfoxy)-4,7-methano-7H-thieno[2,3-e][1,3]diazepine-8-carboxamide Stage A The procedure is carried out as in Stage M of Example 19 with 315 mg of the product obtained in Stage A of Example 24, 14.5 ml of toluene, 150.63 mg of 2-ethylbenzene or 2-ethylphenylboronic acid, 77.4 mg of $Pd(PPh_3)_4$ and 2.7 ml of a 2 M aqueous $Na_2CO_3$ solution. 274.2 mg of the compound methyl trans-2-(2-ethylphenyl)-4,5,6,8-tetrahydro-6-oxo-5-(phenylmethoxy)-4,7-methano-7H-thieno[2,3-e][1,3]diazepine-8-carboxylate having the empirical formula $C_{25}H_{24}N_2O_4S$ are obtained (M=448.54 g).

The corresponding yield is 91.2%.

Stage B

The procedure is carried out as in Stage A of Example 7 with 270.8 mg of the product obtained in the preceding stage, 5 ml of dioxane, 1.45 ml of water, 0.63 ml of 1 N aqueous sodium hydroxide. 237.5 mg of compound trans-2-(2-ethylphenyl)-4,5,6,8-tetrahydro-6-oxo-5-(phenylmethoxy)-4,7-methano-7H-thieno[2,3-e][1,3]diazepine-8-carboxylic acid having the empirical formula $C_{24}H_{22}N_2O_4S$ are obtained (M=434.52 g).

The corresponding yield is 90.5%.

Stage C

The procedure is carried out as in Stage B of Example 7 with 234.2 mg of product obtained in the preceding stage, 3.3 ml of DMF, 357.58 mg of BOP, 109.2 mg of HOBT, 57.7 mg of $NH_4Cl$ and 375.5 μl of DIPEA. 210 mg of compound trans-2-(2-ethylphenyl)-4,5,6,8-tetrahydro-6-oxo-5-(phenylmethoxy)-4,7-methano-7H-thieno[2,3-e][1,3]diazepine-8-carboxamide having the empirical formula $C_{24}H_{23}N_3O_3S$ are obtained (M=433.53 g).

The corresponding yield is 90%.

Stage D

The procedure is carried out as in Stage M of Example 1 with 191.1 mg of product obtained in the preceding stage, 38.2 ml of methanol, 19.1 ml of THF and 191.1 mg of 30% palladium on carbon. 107.2 mg of the compound trans-2-(2-ethylphenyl)-4,5,6,8-tetrahydro-5-hydroxy-6-oxo-4,7-methano-7H-thieno[2,3-e][1,3]diazepine-8-carboxamide having the empirical formula $C_{17}H_{17}N_3O_3S$ are obtained (M=343.41 g).

The corresponding yield is 70.8%.

Stage E

The procedure is carried out as in Stage N of Example 1, with 107.2 mg of the product obtained in the preceding stage, 149 mg of the pyridine-$SO_3$ complex.

The crude product obtained is purified by chromatography on silica, eluting with a methylene chloride/ethanol/triethylamine 60/40/0.5 mixture. 106.3 mg of the compound triethylammonium salt of trans-2-(2-ethylphenyl)-4,5,6,8-tetrahydro-6-oxo-5-(sulfoxy)-4,7-methano-7H-thieno[2,3-e][1,3]diazepine-8-carboxamide having the empirical formula $C_{23}H_{32}O_6N_4S_2$ are obtained (M=524.66 g).

The corresponding yield is 76.6%.

Stage F

The procedure is carried out as in Stage R of Example 12 with 106.3 mg of the product obtained in the preceding stage and 31 g of Dowex resin. The elution is carried out with water containing 20% of THF. 81.1 mg of compound sodium salt of trans-2-(2-ethylphenyl)-4,5,6,8-tetrahydro-6-oxo-5-(sulfoxy)-4,7-methano-7H-thieno [2,3-e][1,3]diazepine-8-carboxamide having the empirical formula $C_{17}H_{16}O_6N_3S_2Na$ are obtained (M=445.45 g).

The corresponding yield is 89.8%.

LC/MS (negative electrospray) $M^-$=422.3; $(2M+Na)^-$=867.

Proton NMR, $D_2O$, 300 MHz, chemical shift and multiplicity:

1.13 (t): $CH_3$—$CH_2$—φ; 2.74 (q): $CH_3$—$CH_2$—φ; 3.62 (broad d) and 3.84 (dd): N—$CH_2$—CH; 4.94 (d): N—$CH_2$—CH; 5.39 (s): CH—CO—N; 7.11 (s): S—C=CH; 7.33 (m) and 7.42 (m): aromatic H.

Example 27

Ethyl trans-1,2,3,5-tetrahydro-9-hydroxy-3-oxo-2-(phenylmethoxy)-1,4-methano-4H-2,4-benzodiazepine-5-carboxylate Stage A 50 g of 3-methoxybenzaldehyde are dissolved in 245 ml of acetic acid. 22 ml of bromine are added dropwise at 0° C., the medium is stirred at room temperature for 4 hours, and then left overnight at room temperature. 300 ml of water are added to the solution and the expected product crystallizes. After filtration and washing with water and drying, 68 g of 2-bromo-5-methoxybenzaldehyde having the empirical formula $C_8H_7BrO_2$ are obtained (M=114 g).

The corresponding yield is 87%.

Stage B 30 g of the product obtained in the preceding step B are dissolved in 200 ml of dichloromethane. 0.4 g of $ZnI_2$ is added at 0° C., followed dropwise by 20.86 ml of TMSCN. The medium is stirred for 1 h 30 min, and then the mixture is poured into a saturated aqueous sodium bicarbonate solution. After decantation, the organic phase is dried over magnesium sulfate and the solvent is evaporated off under reduced pressure. The crude product is solubilized in 9 ml of ethanol and 6 ml of concentrated hydrochloric acid. After heating under reflux for 1 h, the reaction medium is poured into a saturated $NaHCO_3$ solution, and then extracted with ethyl acetate. After evaporation of the solvent under reduced pressure, 41 g of ethyl 2-bromo-α-hydroxy-5-methoxybenzeneacetate having the empirical formula $C_{11}H_{13}BrO_4$ are obtained (M=288 g).

The corresponding yield is 63%.

Stage C 23.5 g of the product obtained in the preceding step are introduced into 250 ml of dichloromethane, in a round-bottomed flask placed under a nitrogen atmosphere. 100 ml of TEA, and 1.05 g of DMAP are added. The medium is cooled to 0° C. and then 6.31 ml of mesyl chloride are introduced therein. The medium is stirred for 1 hour at 0° C.

The reaction medium is next poured over a mixture of water and dichloromethane. The medium is extracted twice with dichloromethane, washed twice with water, the organic phases are combined and they are dried over sodium sulfate, and then the solvent is evaporated off under reduced pressure.

32 g of the expected compound having the empirical formula $C_{17}H_{24}N.BrO_5$ are obtained in the form of an oil (M=401 g).

Stage D

The procedure is carried at as indicated in Stage C of Example 21 with 130 ml of DMF, 16 g of tert-butyl glycinate and 9.66 ml of lutidine.

30 g of the product obtained in the preceding Stage C and 130 ml of DMF are introduced into a round-bottomed flask placed under a nitrogen atmosphere. 9.66 ml of 2,6-lutidine and 16 g of tert-butyl glycinate are added. The medium is heated at 80° C. for 6 hours. The temperature is allowed to return to room temperature and the medium is poured into a mixture of ice and sulphuric ether. The medium is extracted once with ether. The ether phase is washed four times with water. The organic phase is dried over sodium sulfate, and then it is filtered and the solvent is evaporated off under reduced pressure. The toluene is carried away. The crude product is taken up in AcOEt, the medium is washed with an aqueous tartaric acid solution at 10% and then twice with water and next with a saturated aqueous sodium hydrogen carbonate solution.

The organic phase is dried over sodium sulfate, filtered and the solvent is evaporated off under reduced pressure. 15.3 g of ethyl 2-bromo-α-[[2-(1,1-dimethylethoxy)-2-oxoethyl]amino]-5-methoxybenzeneacetate having the empirical formula $C_{17}H_{24}BrNO_5$ are obtained in the form of an oil (M=402.29 g).

The corresponding yield is 47%.

Stage E 6 g of the product obtained in Stage D, 2.2 ml of triethylamine and 60 ml of dichloromethane are introduced into a round-bottomed flask cooled by an ice bath.

The medium is cooled to 0° C. and 2.4 ml of trifluoroacetic anhydride and are added.

The medium is left in contact for 2 hours 30 minutes.

The reaction medium is next poured over an ice/aqueous ammonia/dichloromethane mixture. The medium is washed with water, and extracted with dichloromethane. The organic phases are dried over sodium sulfate. The medium is filtered and the solvent is evaporated off under reduced pressure.

6.05 g of ethyl 2-bromo-α-[[2-(1,1-dimethylethoxy)-2-oxoethyl](trifluoroacetyl)amino]-5-methoxybenzeneacetate having the empirical formula $C_{19}H_{23}BrF_3NO_6$ are obtained (M=498.30 g).

The corresponding yield is 81%.

Stage F 6.05 g of the product obtained in Stage E and 30 ml of dichloromethane are introduced into a round-bottomed flask placed under a nitrogen atmosphere.

The medium is cooled to 0° C. and 30 ml of trifluoroacetic acid are rapidly introduced.

The temperature is allowed to rise to room temperature and then the medium is kept stirred for 4 hours.

The solvent is evaporated off under reduced pressure.

The product is dissolved in AcOEt, successively washed with a dilute solution of aqueous ammonia and then with a saturated aqueous $NaH_2PO_4$ solution.

The organic phases are next dried over sodium sulfate, filtered and the solvent is evaporated off under reduced pressure.

5.2 g of ethyl 2-bromo-α-[[(carboxymethyl)(trifluoroacetyl)amino]-5-methoxybenzeneacetate having the empirical formula $C_{15}H_{15}BrF_3NO_6$ are obtained in the form of white crystals (M=442.19 g).

The corresponding yield is 97%.

Stage G

Step 1 Preparation of the Acid Chloride 61 g of the product obtained in Stage F is solubilized in 120 ml of $SOCl_2$. The medium is heated at 80° C. for 2 h and then evaporated to dryness.

Step 2

The acid chloride is solubilized in 300 ml of $CH_3NO_2$. 76 g of aluminum chloride are then added in fractions, and the medium is stirred overnight at room temperature. The reaction medium is then poured into a hepthane/ethyl acetate mixture and the organic phase is washed with 1 M $NaH_2PO_4$. After drying the organic phase over $MgSO_4$ and evaporation of the solvent under reduced pressure, the residue obtained is purified by chromatography on silica, eluting with a heptane/ethyl acetate 4:1 mixture. A residue is obtained which is crystallized from a pentane/ether mixture.

31 g of ethyl 8-bromo-1,2,3,4-tetrahydro-5-hydroxy-4-oxo-2-(trifluoroacetyl)-1-isoquinolinecarboxylate having the empirical formula $C_{14}H_{11}BrF_3NO_5$ are obtained (M=409.15 g).

The corresponding yield is 55%.

Stage H 30 g of the product obtained in the preceding Stage G are dissolved in 250 ml of ethanol. 3 g of 10% by weight of palladium on carbon and 21.1 ml of triethylamine are then added. The medium is placed under hydrogen pressure. After 1 h 30 min, the catalyst is filtered off and then the filtrate is poured into a heptane/ethyl acetate mixture, the organic phase is washed with a 1 M aqueous $NaH_2PO_4$ solution, and then dried over magnesium sulfate and the solvent is evaporated off under reduced pressure. The crude product obtained is purified on silica, eluting with a heptane/ethyl acetate 4/1 mixture.

22.2 g of ethyl 1,2,3,4-tetrahydro-5-hydroxy-4-[(phenylmethoxy)imino]-2-(trifluoroacetyl)-1-isoquinolinecarboxylate having the empirical formula $C_{14}H_{12}F_2NO_5$ are obtained (M=331.25 g).

The corresponding yield is 92%.

Stage I

The procedure is carried out as in Stage E of Example 12 with 24.4 g of the product obtained in the preceding stage, 250 ml of pyridine and 15.5 g of O-benzylhydroxylamine hydrochloride. 25.6 g of compound ethyl 1,2,3,4-tetrahydro-5-hydroxy-4-[(phenylmethoxy)imino]-2-(trifluoroacetyl)-1-isoquinolinecarboxylate having the empirical formula $C_{21}H_{19}F_3N_2O_5$ are obtained (M=436.39).

The corresponding yield is 80%.

Stage J 25.7 g of the product obtained in the preceding stage are dissolved in 300 ml of acetone. 90 g of $K_2CO_3$ and 17.3 ml of allyl bromide are added to the solution. The medium is heated overnight under reflux and then the solution is poured into a heptane/ethyl acetate 1/2 mixture, and the medium is washed with water. The organic phase is then washed with an $NaH_2PO_4$ solution, and then dried over magnesium sulfate. After evaporation of the solvent under reduced pressure, 30 g of crude product are obtained, which product is purified by chromatography on a silica column, eluting with a heptane/ethyl acetate 4/1 mixture. After a second purification by chromatography on silica, eluting with a heptane/ethyl acetate 8/1 mixture, 24.8 g of the compound ethyl 1,2,3,4-tetrahydro-4-[(phenylmethoxy)imino]-5-(2-propenyloxy)-2-(trifluoroacetyl)-1-isoquinolinecarboxylate having the empirical formula $C_{24}H_{23}F_3N_2O_5$ are obtained in the form of a yellow oil (M=476.47).

The corresponding yield is 87%.

Stage K 25.2 g of the product obtained in the preceding stage are dissolved in 300 ml of ethanol. Gaseous $NH_3$ is bubbled through at 0° C. for 5 minutes and then the solution is stirred at room temperature for 3 hours. The solution is treated by adding ethyl acetate and the organic phase is washed with an aqueous $NaH_2PO_4$ solution and then dried over magnesium sulfate. After evaporation of the solvents under reduced pressure and carrying away with toluene, 21.2 g of the compound ethyl 1,2,3,4-tetrahydro-4-[(phenylmethoxy)imino]-5-(2-propenyloxy)-1-isoquinolinecarboxylate having the empirical formula $C_{22}H_{24}N_2O_4$ are obtained in the form of a yellow oil (M=300.45 g). The yield is quantitative.

Stage L 22.5 g of the product obtained in the preceding stage are dissolved in 300 ml of THF. 1.1 equivalent of $Boc_2$—O reagent are added. The medium is stirred for 2 hours at room temperature and then the reaction medium is poured into a heptane/ethyl acetate 1/2 mixture and the mixture is washed with a tartaric acid solution at 10%. The organic phase is next dried over magnesium sulfate and the solvent is evaporated under reduced pressure. A residue is obtained which is purified by chromatography on a silica column, eluting with a heptane/ethyl acetate 5/1 mixture. After evaporation of the solvent, 19.3 g of the compound 2-(1,1-dimethylethyl) and 1-ethyl 3,4-dihydro-4-[(phenylmethoxy)imino]-5-(2-propenyloxy)-1,2(1H)-isoquinolinedicarboxylate having the empirical formula $C_{27}H_{32}N_2O_6$ are obtained in the form of white crystals (M=480.57).

Stage M

The procedure is carried out as in Stage F of Example 12 with 19.3 g of the product obtained in the preceding stage, 250 ml of methanol, 40.5 g of $NaBH_3CN$, 59 ml of boron trifluoride etherate. 21 g of compound 2-(1,1-dimethylethyl) and 1-ethyl 3,4-dihydro-4-[(phenylmethoxy)amino]-5-(2-propenyloxy)-1,2(1H)-isoquinolinedicarboxylate having the empirical formula $C_{27}H_{34}N_2O_6$ are obtained (M=482.58 g).

The corresponding yield is 79%.

Stage N

The procedure is carried out as in Stages I and J of Example 1 with 15.3 g of the product obtained in the preceding stage, 10 ml of methanol, 83 ml of an HCl solution in ethyl acetate. Then 130 ml of methylene chloride and 35 ml of 2 N aqueous sodium hydroxide [lacuna]. 12.1 g of the compound ethyl 1,2,3,4-tetrahydro-4-[(phenylmethoxy)amino]-5-(2-propenyloxy)-1-isoquinolinecarboxylate having the empirical formula $C_{22}H_{26}N_2O_4$ are obtained in the form of a colorless oil (M=382.46 g).

The yield is quantitative.

Stage O

The procedure is carried out as in Stage K of Example 1 with 12.1 g of the product obtained in the preceding stage, 9 ml of triethylamine and 2 ml of diphosgene and 31 [lacuna] of acetonitrile. 7 g of the compound ethyl trans-1,2,3,5-tetrahydro-3-oxo-2-(phenylmethoxy)-9-(2-propenyloxy)-1,4-methano-4H-2,4-benzodiazepine-5-carboxylate having the empirical formula $C_{23}H_{24}N_2O_5$ are obtained (M=408.48 g).

The yield is 55%.

Stage P 4.1 g of the compound obtained in the preceding stage are dissolved in 50 ml of toluene, in a round-bottomed flask placed under an argon atmosphere. 231 mg of $Pd(PPh_3)_4$ and 630 µl of acetic acid are added. 3.49 ml of $Bu_3SnH$ are then added dropwise at 0° C. over 10 minutes. The reaction medium is stirred at room temperature for two hours. 200 ml of $CH_3CN$ are next added to the reaction medium and the medium is extracted three times with 60 ml of pentane. The acetonitrile solution is next evaporated and the residue is purified by chromatography on silica, eluting with a heptane/ethyl acetate 2/1 then 1/1 mixture. 3.45 g of the compound ethyl 1,2,3,4-tetrahydro-5-hydroxy-4-[(phenylmethoxy)imino]-2-(trifluoroacetyl)-1-isoquinolinecarboxylate having the empirical formula $C_{20}H_{20}N_2O_5$ are obtained (M=368.39 g).

The corresponding yield is 94%.

LC/MS (positive electrospray), m/z: $M^+$=369.

LC/MS (negative electrospray), m/z: $(M^-H)^-$=367.

Proton NMR, $CDCl_3$ to 300 MHz, chemical shift and multiplicity:

1.32 (t): $CH_3$—$CH_2O$—CO; 4.27 (qd): $CH_3$—$CH_2$—O—CO; 3.52 (dd) and 3.67 (d): N—$CH_2$—CH; 4.60 (d): N—$CH_2$—CH; 4.93 and 4.99 (ab): O—$CH_2$-φ; 5.01 (s): φ-OH; 5.10 (s): $CH_2$—CO—O—$CH_2$—$CH_3$; 6.68 (d), 6.93 (d) and 7.13 (t): aromatic H, 7.37 (m) and 7.46 (m): $CH_2$-φ.

Example 28

Sodium Salt of Ethyl Trans-1,2,3,5-tetrahydro-3-oxo-9-[[(phenylamino)carbonyl]oxy]-2-(sulfoxy)-1,4-methano-4H-2,4-benzodiazepine-5-carboxylate.

Stage A 0.1 g of the product obtained in Stage P of Example 27 is dissolved in 2 ml of dichloromethane, in a round-bottomed flask placed under an argon atmosphere. 0.019 ml of triethylamine is added and then PhNCO is added dropwise at 0° C. The medium is stirred for 30 minutes and then the solution is poured into dichloromethane and the organic phase is washed with an aqueous $NaH_2PO_4$ solution. The organic phase is dried over magnesium sulfate and the solvent is evaporated off under reduced pressure. 0.130 g of crude product is obtained which is purified by chromatography on silica, eluting with an ethane/ethyl acetate 1/1 mixture. 0.119 g of compound ethyl trans-1,2,3,5-tetrahydro-3-oxo-9-[[(phenylamino)carbonyl]oxy]-2-(phenylmethoxy)-1,4-methano-4H-2,4-benzodiazepine-5-carboxylate having the empirical formula $C_{27}H_{25}N_3O_6$ are obtained (M=487.52 g).

The corresponding yield is 90%.

Stage B

The procedure is carried out as in Stage M of Example 1 with 0.115 g of the product obtained in the preceding stage, 10 ml of THF and 0.027 g of 10% palladium on carbon. The product obtained is treated as in Stage N of Example 1 with 2 ml of pyridine, 114 mg of the pyridine-$SO_3$ complex. The product obtained is treated as in Stage R of Example 12 in the presence of 25 g of Dowex resin. At the end of these three steps, 0.107 g of the compound sodium salt of ethyl trans-1, 2,3,5-tetrahydro-3-oxo-9-[[(phenylamino)carbonyl]oxy]-2-(sulfoxy)-1,4-methano-4H-2,4-benzodiazepine-5-carboxylate having the empirical formula $C_{20}h_{18}N_3O_9S,Na$ is obtained in the form of pale yellow crystals (M=476.45 g+22.99 g).

The corresponding yield is 90%.

LC/MS (positive electrospray) m/z: $M+Na^+=522$.

Proton NMR, DMSO-$d_6$, 300 MHz, chemical shift and multiplicity:

1.28 (t): $CH_3$—$CH_2$—O; 4.24 (q): $CH_3$—$CH_2$—O; 3.52 (d), 3.60 (dd): $CH_2$—CH; 4.98 (d): $CH_2$—CH; 5.05 (s): CH—$CO_2Et$; 7.04, 7.33, 7.50, 7.42, 7.22: aromatic H; 10.08 (1H) active.

Example 29

Disodium Salt of 5-ethyl trans-1,2,3,5-tetrahydro-3-oxo-2,9-bis(sulfoxy)-1,4-methano-4H-2,4-benzodiazepine-5-carboxylate Stage A The procedure is carried out as in Stage M of Example 1 with 0.130 g of the product obtained in Stage P of Example 27, 13 ml of THF and 10% palladium on carbon. The compound ethyl trans-1,2,3,5-tetrahydro-2,9-dihydroxy-3-oxo-1,4-methano-4H-2,4-benzodiazepine-5-carboxylate having the empirical formula $C_{13}H_{14}N_2O_5$ is obtained with a quantitative yield (M=278.27 g).

Stage B

The procedure is carried out as in Stage N of Example 1 with 0.1 g of the product obtained in the preceding stage, 0.33 g of pyridine-$SO_3$ complex and 2 ml of pyridine. The product is then obtained and treated in the same manner as in Stage R of Example 12 in the presence of 25 g of Dowex resin. 0.170 g of the compound disodium salt of 5-ethyl trans-1,2,3,5-tetrahydro-3-oxo-2,9-bis(sulfoxy)-1,4-methano-4H-2,4-benzodiazepine-5-carboxylate having the empirical formula $C_{13}H_{12}N_2Na_2O_{11}S_2$ is obtained (M=482.35 g).

The corresponding yield is quantitative.

LC/MS (positive electrospray) m/z: $M+Na^+=505$.

Proton NMR, DMSO-$d_6$, 300 MHz, chemical shift and multiplicity:

3.44 (d): $CH_2$—CH; 3.53 (dd): $CH_2$—CH; 1.26 (t): $CH_3$—$CH_2$—O—CO; 4.21 (q): $CH_3$—$CH_2$—O—CO; 4.94 (s): CH—$CH_2Et$; 5.20 (d): CH—$CH_2$; 7.06 (d), 7.18 (d), 7.27 (d): the three aromatic H.

Example 30

Sodium Salt of 5-ethyl trans-1,2,3,5-tetrahydro-3-oxo-2-(sulfoxy)-9-[[(trifluoromethyl)sulfonyl]oxy]-1,4-methano-4H-2,4-benzodiazepine-5-carboxylate Stage A 1 g of the product obtained in Stage P of Example 27 is dissolved in 15 ml of dichloromethane, in a round-bottomed flask placed under argon at −15° C. 1.17 ml of triethylamine are added, followed by 0.67 ml of $(CF_3SO_2)_2O$. The medium is stirred for 30 minutes at −15° C. and then, once the reaction medium has returned to room temperature, it is treated with an $NaHCO_3$ solution and extracted with methylene chloride. The organic phase is then dried over magnesium sulfate and the solvent is evaporated off under reduced pressure. 1.5 g of a gum are obtained, which gum is purified by chromatography on silica, eluting with a heptane/ethyl acetate 4/1 mixture. 0.8 g of the compound ethyl trans-1,2,3,5-tetrahydro-3-oxo-2-(phenylmethoxy)-9-[[(trifluoromethyl)sulfonyl]oxy]-1,4-methano-4H-2,4-benzodiazepine-5-carboxylate having the empirical formula $C_{21}H_{19}F_3N_2O_7F$ is obtained in the form of white crystals (M=500.4 g).

The corresponding yield is 60%.

Stage B

The procedure is carried out as indicated in Stage M of Example 1 with 0.130 mg of the product obtained in the preceding stage, 13 ml of THF and 25 mg of 10% palladium on carbon. 91 mg of the compound ethyl trans-1,2,3,5-tetrahydro-2-hydroxy-3-oxo-9-[[(trifluoromethyl)sulfonyl]oxy]-1,4-methano-4H-2,4-benzodiazepine-5-carboxylate having the empirical formula $C_{14}H_{13}N_2O_7S$ are obtained (M=410.33 g).

The corresponding yield is 90%.

Stage C

The procedure is carried out as indicated in Stage N of Example 1 with 91 mg of the product obtained in the preceding stage, 2 ml of pyridine and 105 mg of the pyridine-$SO_3$ complex. The product obtained is then treated as indicated in Stage R of Example 12 with 25 g of Dowex resin. 0.110 g of the compound sodium salt of 5-ethyl trans-1,2,3,5-tetrahydro-3-oxo-2-(sulfoxy)-9-[[(trifluoromethyl)sulfonyl]oxy]-1,4-methano-4H-2,4-benzodiazepine-5-carboxylate having the empirical formula $C_{14}H_{12}F_3N_2O_{10}S_2Na$ is obtained in the form of white crystals (M=489.38+22.99 g).

The corresponding yield is 97%.

LC/MS (positive electrospray), m/z: $M+Na^+=535$.

Proton NMR, DMSO-$d_6$, 300 MHz, chemical shift and multiplicity:

1.26 (t): $CH_3$—$CH_2$—O—CO; 4.24 (q): $CH_3$—$CH_2$—O—CO; 3.50 (d) and 3.67 (dd): $CH_2$—CH; 5.02 (d): $CH_2$—CH; 5.17 (s): CH—$CO_2Et$; 7.45 (d), 7.50 (d), 7.59 (t): the 3 aromatic H.

Example 31

Sodium Salt of 5-ethyl trans-9-(4-fluorophenyl)-1,2,3,5-tetrahydro-3-oxo-2-(sulfoxy)-1,4-methano-4H-2,4-benzodiazepine-5-carboxylate Stage A The procedure is carried out as in Stage M of Example 19 with 0.35 g of the product obtained in Stage A of Example 30, 15 ml of toluene, 0.146 g of 4-fluorophenylboronic acid, 70 mg of $Pd(P\phi_3)_4$, 2.8 ml of a 2 M $Na_2CO_3$ solution. 0.280 g of compound ethyl trans-9-(4-fluorophenyl)-1,2,3,5-tetrahydro-3-oxo-2-(phenylmethoxy)-1,4-methano-4H-2,4-benzodiazepine-5-carboxylate having the empirical formula $C_{26}H_{23}FN_2O_4$ is obtained (M=446.48 g).

The corresponding yield is 90%.

Stage B

The procedure is carried out as indicated in Stage M of Example 1 with 0.270 g of the product obtained in the preceding stage, 5 ml of THF, and 10% palladium on carbon. The product obtained is treated as indicated in Stage N of Example 1 with 3 ml of pyridine and 257 mg of pyridine-$SO_3$ complex. The product obtained is treated as indicated in Stage R of Example 12 with 25 g of Dowex resin. 0.28 g of the compound sodium salt of 5-ethyl trans-9-(4-fluorophenyl)-1,2,3,5-tetrahydro-3-oxo-2-(sulfoxy)-1,4-methano-4H-2,4-benzodiazepine-5-carboxylate having the empirical formula $C_{19}H_{16}FN_2NaO_7S$ is obtained in the form of white crystals (M=458.40 g).

The corresponding yield is quantitative.

Proton NMR, DMSO-$d_6$, 300 MHz, chemical shift and multiplicity:

1.28 (t): $CH_3$—$CH_2$—O; 4.23 (q): $CH_3$—$CH_2$—O; 3.46 (dd) and 3.53 (d): $CH_2$—CH; 4.59 (d): $CH_2$—CH; 5.05 (s): CH—$CO_2$; 7.14 (m) and 7.52 (m): the 4 aromatic H of the fluorinated nucleus; 7.19 (d), 7.34 (d) and 7.43 (t): the 3 aromatic H.

Example 32

Ethyl 1,2,3,5-tetrahydro-3-oxo-8-hydroxy-2-(phenylmethoxy)-1,4-methano-4H-2,4-benzodiazepine-5-carboxylate Stage A
Step 1

51.72 g of an ethyl glyoxalate solution at 50% in toluene are introduced, in the hot state, into a solution of 48 g (0.253 mol) of D,L-norphenylephrine hydrochloride in 94 ml of methanol heated under reflux.

After refluxing for 30 minutes, the hydrochloride of the expected product precipitates. The suspension is again left for 30 minutes under reflux before being cooled by an ice bath in order to cause the expected hydrochloride to crystallize.

After adding 50 ml of ether, the filtered precipitate, washed with ether, gives 46 g of ethyl 1,2,3,4-tetrahydro-4,6-dihydro-1-isoquinolinecarboxylate.

Step 2

25 ml of TEA are added to a suspension, cooled to 0° C., of 44 g (0.160 mol) of the compound obtained in the preceding step in 500 ml of THF. Then, after a change in the appearance of the suspension, 38.7 g (0.177 mol) of $(BOC)_2O$ are added. The medium is next stirred for 2 hours at 20° C. before pouring the reaction medium over a 10% aqueous sodium hydrogen sulfate solution.

After extraction with THF and with ethyl acetate, the organic phase is again washed with a first sodium hydrogen sulfate solution and then a second sodium dihydrogen phosphate solution at 1 molar. The organic phase is dried over magnesium sulfate and then filtered and the solvent is evaporated off under reduced pressure to give 60.2 g of 2-(1,1-dimethylethyl) and 1-ethyl 3,4-dihydro-4,6-dihydroxy-1,2 (1H)-isoquinolinedicarboxylate having the empirical formula $C_{17}H_{23}NO_6$ (M=337.38 g)

Stage B 60 g (1.177 mol) of the compound obtained in Stage A2 are introduced into 600 ml of acetone. 49.4 g of potassium carbonate are then added, followed dropwise by 29 ml of allyl bromide. The medium is heated under reflux for 2 hours 30 minutes and then the salts are filtered, and the acetone is evaporated off.

The residue is dissolved in a heptane/ACOEt mixture. The organic phase is next washed with a saturated sodium bicarbonate solution, dried over magnesium sulfate, and the solvent is then evaporated off under reduced pressure.

66 g of 2-(1,1-dimethylethyl) and 1-ethyl 3,4-dihydro-4-hydroxy-6-(2-propenyloxy)-1,2(1H)-isoquinolinedicarboxylate having the empirical formula $C_{20}H_{27}NO_6$ are obtained (M=377.44 g).

The corresponding yield is 98%.

Stage C 57.5 g of pyridinium chlorochromate and 120 g of molecular sieve are introduced into 1 liter of dichloromethane. A solution of 65.5 g (0.178 mol) of the compound obtained in Stage B is then introduced at 0° C. into 300 ml of dichloromethane. The solution is stirred for 1 hour 30 minutes, while allowing the temperature to return to room temperature, and then the medium is filtered on 1 kg of Florisil, eluting with dichloromethane.

After evaporation of the solvent under reduced pressure, 49.92 g of 2-(1,1-dimethylethyl) and 1-ethyl 3,4-dihydro-4-oxo-6-(2-propenyloxy)-1,2(1H)-isoquinolinedicarboxylate having the empirical formula $C_{20}H_{25}NO_6$ are obtained (M=375.40 g).

The corresponding yield is 78%.

Stage D 49.9 g of the compound obtained in Stage C are introduced into 500 ml of pyridine and then 23.3 g of $PhCH_2ONH_2.HCl$ are added and the reaction medium is stirred for 1 hour.

The solvent is evaporated off under reduced pressure and then the residue is dissolved in a mixture of heptane/ACOEt 1/2 solvent The organic phase is washed 3 times with a sodium hydrogen sulfate solution at 10% and then dried over magnesium sulfate.

57 g of 2-(1,1-dimethylethyl) and 1-ethyl 3,4-dihydro-4-[(phenylmethoxy)imino]-6-(2-propenyloxy)-1,2(1H)-isoquinolinedicarboxylate having the empirical formula $C_{27}H_{32}N_2O_6$ are obtained in the form of an oil (M=480.57 g).

The corresponding yield is 89%.

Stage E

The procedure is carried out as indicated in H of Example 31 with 56 g of the product obtained in Stage D, 44 g of sodium cyanoborohydride and 500 ml of glacial acetic acid.

56 g of the product obtained in Stage D and 500 ml of glacial acetic acid are introduced into a round-bottomed flask placed under a nitrogen atmosphere. The medium is cooled to 10° C. and about 44 g of sodium cyanoborohydride are added. The temperature is allowed to return to room temperature and the reaction is allowed to proceed for 5 hours. The medium is taken up in 400 ml of AcOEt, poured into 600 ml of 1 N sodium hydroxide, the medium is separated by decantation, extracted several times with AcOEt, washed again with 1 N sodium hydroxide, and then with water and then with a sodium chloride solution. The aqueous phase is dried over magnesium sulfate, filtered and the solvent is evaporated off under reduced pressure. The residue is purified by chromatography on silica, eluting with a dichloromethane/AcOEt 97/3 mixture.

22 g of 2-(1,1-dimethylethyl) and 1-ethyl (1S)-3,4-dihydro-4-[(phenylmethoxy)amino]-6-(2-propenyloxy)-1,2 (1H)-isoquinolinedicarboxylate having the empirical formula $C_{27}H_{34}N_2O_6$ are obtained (M=482.58 g).

The corresponding yield is 40%.

Stage F

The procedure is carried out as in Stages I and J of Example 1 with 22 g of the product obtained in Stage E, 22 ml of ethyl acetate, 95 ml of a 4.6 M hydrochloric acid solution in ACOEt.

16.5 g of ethyl (1S)-1,2,3,4-tetrahydro-4-[(phenylmethoxy)amino]-6-(2-propenyloxy)-1-isoquinolinecarboxylate having the empirical formula $C_{22}H_{26}N_2O_4$ are obtained (M=382.46 g).

The corresponding yield is quantitative.

Stage G

The procedure is carried out as in Stage K of Example 1 with 16.4 g of the product obtained in Stage F, 3.5 liters of ethyl acetate, 14.2 ml of TEA, and 4.2 g of diphosgene.

3.5 g of ethyl trans-1,2,3,5-tetrahydro-3-oxo-2-(phenylmethoxy)-8-(2-propenyloxy)-1,4-methano-4H-2,4-benzodiazepine-5-carboxylate having the empirical formula $C_{23}H_{24}N_2O_5$ are obtained (M=408 g).

The corresponding yield is 20%.

Stage H 3.5 g of the product obtained in the preceding Stage G are dissolved in 35 ml of toluene. 0.191 g of Pd(PPh$_3$)$_4$ is introduced therein under argon at 0° C., followed by 0.52 g of acetic acid, and finally, dropwise, 2.89 g of Bu$_3$SnH.

The medium is stirred for 45 minutes at 0° C. and then the solvent is evaporated off under reduced pressure and the residue is purified by chromatography on silica with a heptane/AcOEt 1/1 mixture.

2.92 g of ethyl 1,2,3,5-tetrahydro-3-oxo-8-hydroxy-2-(phenylmethoxy)-1,4-methano-4H-2,4-benzodiazepine-5-carboxylate having the empirical formula $C_{20}H_{20}N_2O_5$ are obtained in the form of white crystals (M=368 g). The corresponding yield is 96%.

Example 33

Sodium Salt of Trans-1,2,3,5-tetrahydro-N-methoxy-8-[(2-methoxyethoxy)methoxy]-3-oxo-2-(sulfoxy)-1,4-methano-4H-2,4-benzodiazepine-5-carboxamide Stage A 3.68 g of the product obtained in Stage H of Example 32 are dissolved in 40 ml of dichloromethane. 1.24 ml of MEMCl and 2 ml of DIEA are added to the reaction medium cooled to 0° C. The medium is stirred for 30 minutes at 0° C. and then 1.24 ml of MEMCl and 2 ml of DIEA are again added. The reaction is next poured into water containing NaH$_2$PO$_4$. The organic phase is extracted and dried over magnesium sulfate and the solvent is evaporated off under reduced pressure. The residue obtained is purified by chromatography on silica, eluting with a dichloromethane mixture containing 5% acetone. 2.8 g of compound ethyl trans-1,2,3,5-tetrahydro-8-[(2-methoxyethoxy)methoxy]-3-oxo-2-(phenylmethoxy)-1,4-methano-4H-2,4-benzodiazepine-5-carboxylate having the empirical formula $C_{24}H_{28}N_2O_7$ are obtained (M=456.50 g).

The corresponding yield is 63%.

Stage B

The procedure is carried out as in Stage A of Example 7 with 2.8 g of the product obtained in the preceding stage, 40 ml of dioxane and 3 ml of water, 6.13 ml of 1 N aqueous sodium hydroxide. 2.18 g of the compound trans-1,2,3,5-tetrahydro-8-[(2-methoxyethoxy)methoxy]-3-oxo-2-(phenylmethoxy)-1,4-methano-4H-2,4-benzodiazepine-5-carboxylic acid having the empirical formula $C_{22}H_{24}N_2O_7$ are obtained (M=428.35 g).

The corresponding yield is 86%.

Stage C

The procedure is carried out as indicated in Stage B of Example 7 with 0.31 g of the product obtained in the preceding stage, 5 ml of DMF, 0.46 g of BOP, 0.15 g of HOBT, 0.13 g of NH$_2$OMe,HCl, 0.5 ml of DIEA. 0.215 g of compound trans-1,2,3,5-tetrahydro-N-methoxy-8-[(2-methoxyethoxy)methoxy]-3-oxo-2-(phenylmethoxy)-1,4-methano-4H-2,4-benzodiazepine-5-carboxamide having the empirical formula $C_{23}H_{27}N_3O_7$ is obtained (M=457.49 g).

The corresponding yield is 64%.

Stage D

The procedure is carried out as indicated in Stage M of Example 1 with 0.2 g of the product obtained in the preceding stage, 3 ml of ethanol, and 25 mg of 10% palladium on carbon. The compound trans-1,2,3,5-tetrahydro-2-hydroxy-N-methoxy-8-[(2-methoxyethoxy)methoxy]-3-oxo-1,4-methano-4H-2,4-benzodiazepine-5-carboxamide having the empirical formula $C_{16}H_{21}N_3O_7$ is obtained with a quantitative yield (M=367.36 g).

Stage E

The procedure is carried out as indicated in Stage N of Example 1 with 0.16 g of the product in the preceding stage, 2 ml of pyridine, 240 mg of the pyridine-SO$_3$ complex. 0.138 g of the compound sodium salt of trans-1,2,3,5-tetrahydro-N-methoxy-8-[(2-methoxyethoxy)methoxy]-3-oxo-2-(sulfoxy)-1,4-methano-4H-2,4-benzodiazepine-5-carboxamide having the empirical formula $C_{16}H_{20}N_3O_{10}S,Na$ is obtained (M=446.42+22.99 g).

The corresponding yield is 68%.

LC/MS (negative electrospray), m/z: M$^-$=446.1.

Proton NMR, DMSO-d$_6$, 300 MHz, chemical shift and multiplicity:

3.23 (s): CH$_3$—O—(CH$_2$)$_2$—O—CH$_2$—O; 3.46 (m), 3.72 (m): CH$_3$—O—(CH$_2$)$_2$—O—CH$_2$—O; 5.24 (broad s): CH$_3$—O—(CH$_2$)$_2$—O—CH$_2$—O; 3.41 (m), 3.88 (broad d): N—CH$_2$—CH; 4.61 (masked): N—CH$_2$—CH; 4.61 (s): CH—CO—N—O—CH$_3$; 3.65 (broad s): CH—CO—N—O—CH$_3$; 6.78 (d), 7.03 (dd), 7.09 (dd): the 3 aromatic H and 11.78 (s): O=C—NH—O.

Example 34

Sodium Salt of Trans-1,2,3,5-tetrahydro-8-hydroxy-N-methoxy-3-oxo-2-(sulfoxy)-1,4-methano-4H-2,4-benzodiazepine-5-carboxamide Stage A 0.06 g of the product obtained in Stage E of Example 33 is dissolved in a solution containing 1 ml of trifluoroacetic acid, 1 ml of dichloromethane and 0.4 ml of anisole. The medium is stirred for 30 minutes and then the reaction medium is evaporated to dryness under reduced pressure. Toluene is added and then the medium is again dried under reduced pressure. The residue is taken up in ether and 30 mg of the compound sodium salt of trans-1,2,3,5-tetrahydro-8-hydroxy-N-methoxy-3-oxo-2-(sulfoxy)-1,4-methano-4H-2,4-benzodiazepine-5-carboxamide are obtained in the form of yellow crystals.

The corresponding yield is 44%.

LC/MS (negative electrospray), m/z: M$^-$=358 g.

Example 35

Sodium Salt of Ethyl Trans-8-(2-aminoethoxy)-1,2,3,5-tetrahydro-3-oxo-2-(sulfoxy)-1,4-methano-4H-2,4-benzodiazepine-5-carboxylate Stage A 0.5 g of the product obtained in Stage H of Example 32 is dissolved in 5 ml of dichloromethane. 0.239 g of Boc-NH—CH$_2$OH and 0.39 g of Pϕ$_3$ are then added. The reaction medium is cooled to 0° C. and 258 μl of DEAD are added dropwise. After stirring for one hour at room temperature, the medium is poured over water, the organic phase is extracted and dried over sodium sulfate. The solvent is evaporated under reduced pressure and the residue is purified by chromatography on silica, eluting with dichloromethane containing 5% acetone. 320 mg of compound ethyl trans-8-[2-[[(1,1-dimethylethoxy)carbonyl]amino]ethoxy]-1,2,3,5-tetrahydro-3-oxo-2-(phenylmethoxy)-1,4-methano-4H-2,4-benzodiazepine-5-carboxylate having the empirical formula $C_{27}H_{33}N_3O_7$ are obtained (M=511.58 g).

The corresponding yield is 47%.

Stage B

The procedure is carried out as indicated in Stage M of Example 1 with 60 mg of the product obtained in the preceding stage, 0.5 ml of ethanol and 7 mg of 10% palladium on carbon. The product obtained is treated as indicated in Stage M of Example 1 with 0.8 ml of pyridine, and 56 mg of the pyridine-$SO_3$ complex, and then as indicated in Stage R of Example 12 with 50 g of Dowex resin. 51 mg of the compound sodium salt of ethyl trans-8-[2-[[(1,1-dimethylethoxy)carbonyl]amino]ethoxy]-1,2,3,5-tetrahydro-3-oxo-2-(sulfoxy)-1,4-methano-4H-2,4-benzodiazepine-5-carboxylate having the empirical formula $C_{20}H_{26}N_3O_{10}$,Na are obtained (M=500.51+22.99 g).

The corresponding yield is 84%.

Stage C

The procedure is carried out as indicated in Stage A of Example 1 with 0.048 g of the product obtained in the preceding stage and 0.5 ml of trifluoroacetic acid. 30 mg of the compound sodium salt of ethyl trans-8-(2-aminoethoxy)-1,2,3,5-tetrahydro-3-oxo-2-(sulfoxy)-1,4-methano-4H-2,4-benzodiazepine-5-carboxylate having the empirical formula $C_{15}H_{18}N_3O_8S$,Na are obtained in the form of white crystals (M=400.39+22.99 g).

The corresponding yield is 79%.

LC/MS (negative electrospray), m/z: $(M-H)^-$=400.

Proton NMR, DMSO-$d_6$, 300 MHz, chemical shift and multiplicity:

1.25(t): $CH_3$—$CH_2$—OCO—CH; 4.21(q): $CH_3$—$CH_2$—OCO—CH; 4.95(s); $CH_3$—$CH_2$—OCO—CH; 2.23(tl): N—$CH_2$—$CH_2$—O; 4.16(m): N—$CH_2$—$CH_2$—O; 3.52(s): N—$CH_2$—CH—; 4.67(s): N—$CH_2$—CH—; 6.81(d), 7.01 (dd), 7.29(d) the 3 aromatic H; 7.95(broad s) the 2 active H.

Example 36

Sodium Salt of Trans-8-(2-aminoethoxy)-1,2,3,5-tetrahydro-3-oxo-2-(sulfoxy)-1,4-methano-4H-2,4-benzodiazepine-5-carboxamide Stage A The procedure is carried out as indicated in Stage A of Example 7 with 0.327 g of the product obtained in Stage A of Example 35, 3 ml of dioxane, 3 ml of water and 0.639 ml of 1 N aqueous sodium hydroxide. 0.285 g of the compound trans-8-[2-[[(1,1-dimethylethoxy)carbonyl]amino]ethoxy]-1,2,3,5-tetrahydro-3-oxo-2-(phenylmethoxy)-1,4-methano-4H-2,4-benzodiazepine-5-carboxylic acid having the empirical formula $C_{25}H_{29}N_3O_7$ is obtained (M=483.53 g).

The corresponding yield is 95%.

Stage B

The procedure is carried out as indicated in Stage B of Example 7 with 0.28 g of the product obtained in the preceding stage, 4 ml of DMF, 0.368 g of BOP, 0.117 g of HOBt, 0.062 g of $NH_4Cl$ and 0.4 ml of DIEA. 0.182 mg of the compound 1,1-dimethylethyl trans-[2-[[5-(aminocarbonyl)-1,2,3,5-tetrahydro-3-oxo-2-(phenylmethoxy)-1,4-methano-4H-2,4-benzodiazepin-8-yl]oxy]ethyl]carbamate having the empirical formula $C_{25}H_{30}N_4O_6$ is obtained (M=482.54 g).

The corresponding yield is 65%.

Stage D

The procedure is carried out as indicated in Stage M of Example 1 with 0.175 g of the product obtained in the preceding stage, 2 ml of ethanol, 2 ml of acetic acid and 40 mg of 10% palladium on carbon. The product obtained is treated as indicated in Stage N of Example 1 with 3 ml of pyridine and 250 mg of the pyridine-$SO_3$ complex. The product obtained is treated as in Stage R of Example 12 with 40 g of Dowex resin which are prepared with sodium hydroxide. 0.130 g of compound sodium salt of 1,1-dimethylethyl trans-[2-[[5-(aminocarbonyl)-1,2,3,5-tetrahydro-3-oxo-2-(sulfoxy)-1,4-methano-4H-2,4-benzodiazepin-8-yl]oxy]ethyl]carbamate having the empirical formula $C_{18}H_{23}N_4O_9S$,Na is obtained (M=471.47+22.99 g).

The corresponding yield is 73%

Stage E

The procedure is carried out as indicated in Stage A of Example 13 with the 130 mg of product obtained in the preceding stage in the presence of 1 ml of trifluoroacetic acid. 80 mg of the compound sodium salt of trans-8-(2-aminoethoxy)-1,2,3,5-tetrahydro-3-oxo-2-(sulfoxy)-1,4-methano-4H-2,4-benzodiazepine-5-carboxamide having the empirical formula $C_{13}H_{15}N_4O_7S$,Na are obtained in the form of beige crystals (M=371.35+22.99 g).

The corresponding yield is 77%.

LC/MS (negative electrospray), m/z: $M^-$=371.

Example 37

Sodium Salt of Ethyl Trans-1,2,3,5-tetrahydro-3-oxo-8-[[(phenylamino)carbonyl]oxy]-2-(sulfoxy)-1,4-methano-4H-2,4-benzodiazepine-5-carboxylate Stage A The procedure is carried out as indicated in Stage A of Example 28 with 0.2 g of the product obtained in Stage H of Example 32, 2 ml of dichloromethane, 0.04 ml of triethylamine and 0.06 ml of phenyl isocyanate. 0.170 g of the compound ethyl trans-1,2,3,5-tetrahydro-3-oxo-8-[[(phenylamino)carbonyl]oxy]-2-(phenylmethoxy)-1,4-methano-4H-2,4-benzodiazepine-5-carboxylate having the empirical formula $C_{27}H_{25}N_3O_6$ is obtained (M=487.52 g).

The corresponding yield is 65%.

Stage B

The procedure is carried out as indicated in Stage M of Example 1 with 0.170 g of the product obtained in the preceding stage, 4 ml of ethanol, 2 ml of THF and 35 mg of 10% palladium on carbon. 0.153 g of compound ethyl trans-1,2,3,5-tetrahydro-2-hydroxy-3-oxo-8-[[(phenylamino)carbonyl]oxy]-1,4-methano-4H-2,4-benzodiazepine-5-carboxylate having the empirical formula $C_{20}H_{19}N_3O_6$ is obtained (M=397.39 g).

The corresponding yield is quantitative.

Stage C

The procedure is carried out as indicated in Stage N of Example 1 with 0.153 mg of the product obtained in the preceding stage, 2 ml of pyridine and 0.177 g of the pyridine-$SO_3$ complex. The compound obtained is then treated as indicated in Stage R of Example 12 with 50 g of Dowex resin. The compound sodium salt of ethyl trans-1,2,3,5-tetrahydro-3-oxo-8-[[(phenylamino)carbonyl]oxy]-2-(sulfoxy)-1,4-methano-4H-2,4-benzodiazepine-5-carboxylate having the empirical formula $C_{20}H_{18}N_3O_9$Sna is obtained (M=476.45+22.99).

LC/MS (negative electrospray), m/z: $M^-$(476.1 g)

Proton NMR, DMSO-$d_6$, 300 MHz, chemical shift and multiplicity:

1.27 (t) and 4.24 (q): $CO_2$—Et; 3.55: N—$CH_2$—CH; 4.72 (broad s): N—$CH_2$—CH; 5.04 (broad s): N—CH—CO; 6.99 (d), 7.26 (dd), 7.39 (d): the 3 aromatic H, 7.51, 7.32 and 7.05: the 5 aromatic H; 10.29: NH.

Example 38

Sodium Salt of Ethyl Trans-8-[[(ethylamino)carbonyl]oxy]-1,2,3,5-tetrahydro-3-oxo-2-(sulfoxy)-1,4-methano-4H-2,4-benzodiazepine-5-carboxylate Stage A The procedure is carried out as indicated in Stage A of Example 28 with 0.2 g of the product obtained in Stage H of Example 32, 3 ml of dichloromethane, 0.037 ml of TEA and 0.041 ml of ethyl isocyanate. 0.170 g of the compound ethyl trans-8-[[(ethylamino)carbonyl]oxy]-1,2,3,5-tetrahydro-3-oxo-2-(phenylmethoxy)-1,4-methano-4H-2,4-benzodiazepine-5-carboxylate having the empirical formula $C_{23}H_{25}N_3O_6$ is obtained (M 439 g).

The corresponding yield is 73%.

Stage B

The procedure is carried out as indicated in Stage M of Example 1 with 0.170 g of the compound obtained in the preceding stage, 3 ml of ethanol and 35 mg of 10% palladium on carbon. 0.14 mg of the compound ethyl trans-8-[[(ethylamino)carbonyl]oxy]-1,2,3,5-tetrahydro-2-hydroxy-3-oxo-1,4-methano-4H-2,4-benzodiazepine-5-carboxylate having the empirical formula $C_{16}H_{19}N_3O_6$ is obtained (M=349.35 g).

Stage C

The procedure is carried out as indicated in Stage N of Example 1 with 0.140 mg of the product obtained in the preceding stage, 2 ml of pyridine and 0.180 g of the pyridine-$SO_3$ complex. The product obtained is then treated as indicated in Stage E of Example 12 with 25 g of Dowex resin. The compound sodium salt of ethyl trans-8-[[(ethylamino)carbonyl]oxy]-1,2,3,5-tetrahydro-3-oxo-2-(sulfoxy)-1,4-methano-4H-2,4-benzodiazepine-5-carboxylate having the empirical formula $C_{16}H_{18}N_3O_9S,Na$ is obtained (M=428 g).

LC/MS (negative electrospray), m/z: $M^-$=428.1 g.

Proton NMR, DMSO-$d_6$, 300 MHz, chemical shift and multiplicity:

1.08 (t): $CH_3$—$CH_2$—NH; 3.09 (m): $CH_3$—$CH_2$—NH; 7.82 (t): $CH_3$—$CH_2$—NH; 1.26 (t): $CH_3$—$CH_2$-0-CO; 4.22 (q): $CH_3$—$CH_3$—O—CO; 3.52 (broad s): N—$CH_2$—CH; 4.67 (broad s): N—$CH_2$—CH; 5.00 (s): N—CH—C=O; 6.86 (broad s), 7.13 (broad d), 7.33 (d): the 3 aromatic H.

Example 39

Sodium Salt of ethyl trans-8-(4-fluorophenyl)-1,2,3,5-tetrahydro-3-oxo-2-(sulfoxy)-1,4-methano-4H-2,4-benzodiazepine-5-carboxylate Stage A The procedure is carried out as indicated in Stage A of Example 30 with 1 g of the compound obtained in Stage H of Example 32, 1.17 ml of triethylamine and 0.67 ml of triflic anhydride. 0.9 g of ethyl trans-1,2,3,5-tetrahydro-3-oxo-2-(phenylmethoxy)-8-[[(trifluoromethyl)sulfonyl]oxy]-1,4-methano-4H-2,4-benzodiazepine-5-carboxylate having the empirical formula $C_{21}H_{19}F_3N_2O_7$ is obtained (M=500.45 g).

Stage B

The procedure is carried out as indicated in Stage M of Example 19 with 0.3 g of the product obtained in the preceding stage, 12 ml of toluene, 60 mg of $Pd(P\phi_3)_4$, 0.125 g of 4-fluoronylboronic acid, 2.4 ml of a 2 N $Na_2CO_3$ solution. 0.25 g of the compound ethyl trans-8-(4-fluorophenyl)-1,2,3,5-tetrahydro-3-oxo-2-(phenylmethoxy)-1,4-methano-4H-2,4-benzodiazepine-5-carboxylate having the empirical formula $C_{26}H_{23}FN_2O_4$ is obtained (M=446.48 g).

The corresponding yield is 70%.

Stage C

The procedure is carried out as indicated in Stage M of Example 1 with 0.25 g of the product obtained in the preceding stage, 6 ml of ethanol, 40 mg of 10% palladium on carbon. 0.20 g of the compound ethyl trans-8-(4-fluorophenyl)-1,2,3,5-tetrahydro-2-hydroxy-3-oxo-1,4-methano-4H-2,4-benzodiazepine-5-carboxylate having the empirical formula $C_{19}H_{17}FN_2O_4$ is obtained (M=356.36 g).

The corresponding yield is quantitative.

Stage D

The procedure is carried out as indicated in Stage N of Example 1 with 0.20 g of the product obtained in the preceding stage, 2 ml of pyridine and 0.20 g of the pyridine-$SO_3$ complex. The product obtained is treated as indicated in Stage E of Example 12 with 25 g of Dowex resin. 0.150 g of the compound sodium salt of ethyl trans-8-(4-fluorophenyl)-1,2,3,5-tetrahydro-3-oxo-2-(sulfoxy)-1,4-methano-4H-2,4-benzodiazepine-5-carboxylate having the empirical formula $C_{19}H_{16}FN_2O_5S,NA$ is obtained in the form of yellow crystals (M=458.40 g).

LC/MS (negative electrospray), m/z: $M^-$=435.1.

Proton NMR, DMSO-$d_6$, 300 MHz, chemical shift and multiplicity:

1.27 (t): $CH_3$—$CH_2$—O—CO; 4.23 (q): $CH_3$—$CH_2$—O—CO; 3.58 (broad s): N—$CH_2$—CH; 4.79 (broad s): N—$CH_2$—CH; 5.06 (s): CH—$CO_2$-Et; 7.30 (t) and 7.68 (m): the H of the fluorinated aromatic nucleus; 7.38 (d), 7.43 (d), 7.66 (masked): the 3 aromatic H.

Example 40

Sodium Salt of ethyl trans-1,2,3,5-tetrahydro-3-oxo-2-(sulfoxy)-8-[[(triluoromethyl)sulfonyl]oxy]-1,4-methano-4H-2,4-benzodiazepine-5-carboxylate Stage A The procedure is carried out as indicated in Stage M of Example 1 with 0.12 g of the product obtained in Stage A of Example 39. 4 ml of ethanol and 30 mg of 10% palladium on carbon. 0.105 g of the compound ethyl trans-1,2,3,5-tetrahydro-2-hydroxy-3-oxo-8-[[(trifluoromethyl)sulfonyl]oxy]-1,4-methano-4H-2,4-benzodiazepine-5-carboxylate having the empirical formula $C_{14}H_{13}F_3N_2O_7S$ is obtained (M=410.33 g).

The corresponding yield is quantitative.

Stage B

The procedure is carried out as indicated in Stage N of Example 1 with 0.108 g of the product obtained in the preceding stage, 2 ml of pyridine and 120 mg of the pyridine-$SO_3$ complex. The product obtained is treated as indicated in Stage R of Example 12 with 25 g of Dowex resin. The compound sodium salt of ethyl trans-1,2,3,5-tetrahydro-3-oxo-2-(sulfoxy)-8-[[(trifluoromethyl)sulfonyl]oxy]-1,4-methano-4H-2,4-benzodiazepine-5-carboxylate having the empirical formula (to be verified by the client) $C_{14}H_{12}F_3N_2O_{10}S_2$ is obtained (M=489 g).

LC/MS (negative electrospray), m/z: $M^-$=489.

Proton NMR, DMSO-$d_6$, 300 MHz, chemical shift and multiplicity:

1.26 (t): $CH_3$—$CH_2$—O—CO; 4.22 (q): $CH_3$—$CH_2$—O—CO; 3.51 (m): N—$CH_2$—CH; 4.78: N—$CH_2$—CH; 5.15 (broad s): N—CH—CO; 7.23 (broad s) and 7.56 (broad s): the 3 aromatic H.

Example 41

Disodium Salt of trans-1,2,3,5-tetrahydro-3-oxo-2-(sulfoxy)-8-[2-(sulfoxy)ethoxy]-1,4-methano-4H-2,4-benzodiazepine-5-carboxamide Stage A The procedure is carried out as indicated in Stage I of Example 12 with 3 g of the product obtained in Stage G of Example 32, 60 ml of THF, 60 ml of tert-butanol, 30 ml of water, 0.054 g of osmium tetroxide and 0.99 g of N-methylmorpholine N-oxide. 3.3 g of crude product are obtained which are used as they are in the next step.

Stage B 3.3 g of the crude product obtained above are dissolved in 60 ml of dimethoxypropane and 14 ml of acetone in the presence of para-toluenesulfonic acid at 0° C. After stirring for 30 minutes, the solution is evaporated to dryness and the residue is purified by chromatography on silica, eluting with a heptane/ethyl acetate 1/1 mixture. 3.075 g of compound ethyl trans-8-[(2,2-dimethyl-1,3-dioxolan-4-yl)methoxy]-1,2,3,5-tetrahydro-3-oxo-2-(phenylmethoxy)-1,4-methano-4H-2,4-benzodiazepine-5-carboxylate having the empirical formula $C_{26}H_{30}N_2O_7$ are obtained (M=482.54 g).

The corresponding yield is 90%.

Stage C

The procedure is carried out as indicated in Stage A of Example 7 with 3 g of the product obtained in the preceding stage, 0.261 g of LiOH.H$_2$O, 15 ml of THF and 15 ml of water. 2 g of the compound trans-8-[(2,2-dimethyl-1,3-dioxolan-4-yl)methoxy]-1,2,3,5-tetrahydro-3-oxo-2-(phenylmethoxy)-1,4-methano-4H-2,4-benzodiazepine-5-carboxylic acid having the empirical formula $C_{24}H_{26}N_2O_7$ are obtained (M=454.48 g).

The corresponding yield is 72%.

Stage D

The procedure is carried out as indicated in Stage B of Example 7 with 2 g of the product obtained in the preceding stage, 32 ml of DMF, 2.79 g of BOP, 10.89 g of HOBt, 0.47 g of NH$_4$Cl, 3.06 ml of diisopropylethylamine. 1.6 g of the compound trans-8-[(2,2-dimethyl-1,3-dioxolan-4-yl)methoxy]-1,2,3,5-tetrahydro-3-oxo-2-(phenylmethoxy)-1,4-methano-4H-2,4-benzodiazepine-5-carboxamide having the empirical formula $C_{24}H_{27}N_3O_6$ are obtained in the form of white crystals (M=453.50 g).

The corresponding yield is 80%.

Stage E 1 g of the product obtained in the preceding stage is dissolved in 10 ml of a trifluoroacetic acid/water 9/1 mixture. The medium is stirred for 10 minutes and then the reaction medium is evaporated to dryness while carrying away with toluene. The residue is solubilized in 50 ml of methylene chloride to which 40 ml of a saturated aqueous NaHCO$_3$ solution are added. 100 ml of THF and 40 ml of a saturated aqueous NaCl solution are added. After decantation, the organic phase is washed with a saturated NaCl solution and it is dried over magnesium sulfate. After evaporation of the solvent under reduced pressure, crystals are obtained which are taken up in ether. After filtration, 0.82 g of the compound trans-8-(2,3-dihydroxypropoxy)-1,2,3,5-tetrahydro-3-oxo-2-(phenylmethoxy)-1,4-methano-4H-2,4-benzodiazepine-5-carboxamide having the empirical formula $C_{21}H_{23}N_3O_6$ is obtained (M=413.43 g).

The corresponding yield is 90%.

Stage F 0.6 g of the product obtained in the preceding stage is dissolved in a mixture containing 13 ml of THF, 4 ml of water and 4 ml of methanol. 0.62 g of NaIO$_4$ is added to the solution cooled to 0° C. The medium is stirred at 0° C. and the product crystallizes. The suspension is poured into ethyl acetate, washed with water and the organic phase is dried over magnesium sulfate. After evaporation under reduced pressure, 53 g of the compound trans-1,2,3,5-tetrahydro-3-oxo-8-(2-oxo-ethoxy)-2-(phenylmethoxy)-1,4-methano-4H-2,4-benzodiazepine-5-carboxamide having the empirical formula $C_{20}H_{19}N_3O_5$ are obtained.

The corresponding yield is 90%.

Stage G 0.52 g of the product obtained in the preceding stage is dissolved in ethanol. The solution is cooled to 0° C. and four equivalents of NaBH$_4$ are added. The medium is stirred for two hours and then a heptane/ethyl acetate 1/4 mixture is added to the reaction medium. The organic phase is washed with water and then with an aqueous NaH$_2$PO$_4$ solution and then dried over magnesium sulfate. After evaporation of the solvent, 0.43 g of crude product is obtained which is purified by chromatography on silica, eluting with a methylene chloride mixture containing 10% methanol. After evaporation of the fractions, 0.187 g of white crystals of the compound trans-1,2,3,5-tetrahydro-8-(2-hydroxyethoxy)-3-oxo-2-(phenyl-methoxy)-1,4-methano-4H-2,4-benzodiazepine-5-carboxamide having the empirical formula $C_{20}H_{21}N_3O_5$ is obtained (M=383.41 g).

The corresponding yield is 38%.

Stage H

The procedure is carried out as indicated in Stage M of Example 1 with 0.18 g of the product obtained in the preceding stage, 2 ml of ethanol, 2 ml of THF and 0.043 g of 10% palladium on carbon. 0.12 g of the compound trans-1,2,3,5-tetrahydro-2-hydroxy-8-(2-hydroxyethoxy)-3-oxo-1,4-methano-4H-2,4-benzodiazepine-5-carboxamide having the empirical formula $C_{13}H_{15}N_3O_5$ is obtained.

The corresponding yield is 90%.

Stage I

The procedure is carried out as indicated in Stage N of Example 1 with 0.12 g of the product obtained in the preceding stage, 3 ml of pyridine and 159 mg of the pyridine-SO$_3$ complex. The product obtained is treated as in Stage R of Example 12 with 25 g of Dowex resin. 0.15 g of the compound disodium salt of trans-1,2,3,5-tetrahydro-3-oxo-2-(sulfoxy)-8-[2-(sulfoxy)ethoxy]-1,4-methano-4H-2,4-benzodiazepine-5-carboxamide having the empirical formula $C_{13}H_{13}N_3O_{11}S_2,2Na$ is obtained (M=451.39+2×22.99 g).

LC/MS (negative electrospray), m/z: $(M^{2-}+H)^-$=451.9. $(M^{2-}+H)^-$=451.9.

Proton NMR, DMSO-d$_6$, 300 MHz, chemical shift and multiplicity:

3.41 (dd) and 3.77 (d): N—CH$_2$—CH; 4.60 (d): N—CH$_2$—CH; 4.02 (m) and 4.10 (m): 0-CH$_2$—CH$_2$; 4.72 (s): CH—CO—NH$_2$; 7.40 (broad s) and 7.86 (broad s): CH—CO—NH$_2$; 6.66 (d), 6.93 (dd), 7.16 (d): the 3 aromatic H.

Example 42

Sodium Salt of trans-8-[(2,2-dimethyl-1,3-dioxolan-4-yl)methoxy]-1,2,3,5-tetrahydro-3-oxo-2-(sulfoxy)-1,4-methano-4H-2,4-benzodiazepine-5-carboxamide Stage A The procedure is carried out as in Stage M of Example 1 with 0.6 g of the product obtained in Stage D of Example 41, 60 mg of 10% palladium on carbon and 20 ml of ethanol and 3 ml of THF. 0.46 g of the compound trans-8-[(2,2-dimethyl-1,3-dioxolan-4-yl)methoxy]-1,2,3,5-tetrahydro-2-hydroxy-3-oxo-1,4-methano-4H-2,4-benzodiazepine-5-carboxamide having the empirical formula $C_{17}H_{21}N_3O_6$ is obtained (M=363.37 g).

The corresponding yield is 86%.

Stage B

The procedure is carried out as in Stage N of Example 1 with 0.46 g of the product obtained in the preceding stage, 3 ml of pyridine and 159 mg of the pyridine-SO$_3$ complex. A compound is obtained which is treated as indicated in Stage R of Example 12 with 25 g of Dowex resin. 0.136 g of the compound sodium salt of trans-8-[(2,2-dimethyl-1,3-dioxolan-4-yl)methoxy]-1,2,3,5-tetrahydro-3-oxo-2-(sulfoxy)-1,4-methano-4H-2,4-benzodiazepine-5-carboxamide having the empirical formula $C_{17}H_{20}N_3O_9S.Na$ is obtained (M=442.43+22.99 g).

The corresponding yield is 93%.

LC/MS (negative electrospray), m/z: $M^-$=442.

Proton NMR, DMSO-$d_6$ to 300 MHz, chemical shift and multiplicity:

1.30 (s), 1.36 (s): $(CH_3)_2$—C—C; 3.42 (broad d), 3.74 (m): N—$CH_2$—CH; 4.60 (broad d): N—$CH_2$—CH; 3.76 (m), 4.09 (dd), 3.95 (m), 4.01 (m): O—$CH_2$—CH—$CH_2$—O; 4.40 (m): O—$CH_2$—CH—$CH_2$—O; 4.73 (broad s): CH—CO—$NH_2$; 7.41 (broad s), 7.87 (broad s): CH—CO—$NH_2$; 6.68 (d), 6.94 (dd), 7.16 (d): the 3 aromatic H.

Example 43

Sodium Salt of Trans-8-(2,3-dihydroxypropoxy)-1,2,3,5-tetrahydro-3-oxo-2-(sulfoxy)-1,4-methano-4H-2,4-benzodiazepine-5-carboxamide 0.136 g of the product obtained in Stage B of Example 42 is dissolved in 1.3 ml of a trifluoroacetic acid/water 9/1 mixture at 0° C. The medium is stirred for 15 minutes, and then the reaction medium is evaporated to dryness. The residue is taken up in ether and then filtered. 0.106 g of the compound sodium salt of trans-8-(2,3-dihydroxypropoxy)-1,2,3,5-tetrahydro-3-oxo-2-(sulfoxy)-1,4-methano-4H-2,4-benzodiazepine-5-carboxamide having the empirical formula $C_{14}H_{16}N_3O_9S.Na$ is obtained (M=401.37 g+23 g).

The corresponding yield is 85%.

LC/MS (negative electrospray), m/z: $M^-$=402.

Proton NMR, DMSO-$d_6$, 300 MHz, (chemical shift and multiplicity):

3.43 (m): $CH_2$—OH; 4.67: $CH_2$—OH; 3.99 (m): 0-$CH_2$—CH—OH; 3.82 (m): O—$CH_2$—CH—OH; 4.97 (broad d): O—$CH_2$—CH—OH; 3.46 and 3.72: N—$CH_2$—CH—N; 4.60 (d): N—$CH_2$—CH—N; 4.73 (s): φ-CH—N—CO; 6.67 (d), 6.91 (dd), 7.16 (d): the 3 aromatic H; 7.41 (broad s) and 7.87 (broad s): CO—$NH_2$.

Example 44

Sodium Salt of ethyl trans-3-(4-fluorophenyl)-4,6,7,8-tetrahydro-6-oxo-7-(sulfoxy)-5,8-methano-5H-thieno[2,3-e][1,3]diazepine-4-carboxylate Stage A 100 mg of the compound 3,4-dibromothiophene are introduced into 300 ml of ether, in a round-bottomed flask placed under an argon atmosphere. The medium is stirred and the reaction medium is cooled to –70° C. and then 271 ml of a 1.6 M butyllithium solution in ether is introduced therein with the aid of a canula-like tube. The medium is stirred for 45 minutes at –70° C. This solution is introduced via a canula-like tube into a solution cooled beforehand to –70° C. under an argon atmosphere of 172 mg of diethyl oxalate in 250 ml of ether containing a small amount of THF. The medium is stirred for 1 hour at –70° C. Then a solution having returned to room temperature, a 1 M aqueous $NaH_2PO_4$ solution is added, the medium is separated by decantation and the aqueous phase is extracted several times with ether. The organic phases are combined and then dried over magnesium sulfate and filtered. After evaporation of the solvent under reduced pressure, 108 g of the expected brominated compound are obtained.

The corresponding yield is quantitative.

Stage B 108.6 g of the product obtained in the preceding stage are dissolved in 570 ml of ethanol and 230 ml of THF. The solution is cooled to –35° C. and 15.7 g of $NaBH_4$ are very slowly added. A gaseous emission is observed and, once the addition is complete, the reaction medium is treated by adding a heptane/ethyl acetate 4/1 mixture. The solution is then poured over an ice-cold 1 M $NaH_2PO_4$ solution and the aqueous phase is extracted with a heptane/ethyl acetate 1/4 mixture. After decantation, the aqueous phase is saturated with NaCl and the aqueous phase is again extracted with a heptane/ethyl acetate 1/42 mixture. The organic phases are combined and dried over magnesium sulfate and then concentrated under reduced pressure. The residue obtained after evaporation is treated with 150 ml of a heptane/ethyl acetate 6/1 mixture and 150 ml of ether. The solution is cooled to –10° C. by a methanol/ice bath in order to cause the boron salts to precipitate. After filtration, the filtrate is purified on silica, eluting with a heptane/ethyl acetate 4/1 mixture. After evaporation of the fractions, 74.5 g of the compound ethyl 4-bromo-α-hydroxy-3-thiopheneacetate having the empirical formula $C_8H_9BrO_3S$ are obtained (M=265.13 g).

The corresponding yield is 68%.

Stage C

The procedure is carried out as in Stage C of Example 27 with 74.5 g of the product obtained in the preceding stage, 97.5 g of $(CH_3SO_2)_2O$ and 80.8 ml of triethylamine and 395 ml of methylene chloride. The compound ethyl 4-bromo-α-[(methylsulfonyl)oxy]-3-thiopheneacetate having the empirical formula $C_9H_{11}BrO_5S_2$ is obtained with a quantitative yield (M=343.22 g).

Stage D

The procedure is carried out as in Stage D of Example 27 with the product obtained in the preceding stage, 57.8 ml of tert-butyl glycinate, 50 ml of 2,6-lutidine. 82.3 g of the compound ethyl 4-bromo-α-[[2-(1,1-dimethylethoxy)-2-oxoethyl]amino]-3-thiopheneacetate having the empirical formula $C_{14}H_{20}BrN_4S$ are obtained (M=378.29 g).

The corresponding yield is 77%.

Stage E

The procedure is carried out as in Stage E of Example 27 with 48 g of the product obtained in the preceding stage, 24 ml of trifluoroacetic anhydride and 22 ml of triethylamine and 250 ml of dichloromethane. 32.75 g of the compound ethyl 4-bromo-α-[[2-(1,1-dimethylethoxy)-2-oxoethyl](trifluoroacetyl)amino]-3-thiopheneacetate having the empirical formula $C_{16}H_{19}BrF_3NO_5S$ are obtained (M=474.30).

The corresponding yield is 53%.

Stage F

The procedure is carried out as in Stage F of Example 27 with 40 g of the product obtained in the preceding stage, 234 ml of trifluoroacetic acid and 230 ml of dichloromethane. 37 g of the compound ethyl 4-bromo-α-[(carboxymethyl)(trifluoroacetyl)amino]-3-thiopheneacetate having the empirical formula $C_{12}H_{11}BrF_3NO_5S$ are obtained (M=418.19 g).

The corresponding yield is quantitative.

Stage G

The procedure is carried out as in Stage G of Example 27 with 37 g of the product obtained in the preceding stage and 66 ml of $SOCl_2$. The medium is heated under reflux and the solution is stirred for one hour. After evaporation to dryness, the product is still treated as in Stage G of Example 27 with 30 g of $AlCl_3$ in solution in 230 ml of nitromethane. 9.94 g of ethyl 3-bromo-4,5,6,7-tetrahydro-7-oxo-5-(trifluoroacetyl)

thieno[3,2-c]pyridine-4-carboxylate having the empirical formula $C_{12}H_9BrF_3NO_4S$ are obtained (M=400.17 g).

The corresponding yield is 28%.

Stage H 9.3 g of the product obtained in the preceding stage are dissolved in 100 ml of dichloromethane and 88 ml of methanol and 0.44 g of $NaBH_4$ is added. The medium is stirred for 30 minutes, and then the reaction medium is poured into a 1 M aqueous solution of $NaH_2PO_4$ and ethyl acetate at 0° C. The organic phase is dried over magnesium sulfate and the solvent is evaporated off under reduced pressure. 8.73 g of the compound ethyl 3-bromo-4,5,6,7-tetrahydro-7-hydroxy-5-(trifluoroacetyl)thieno[3,2-c]pyridine-4-carboxylate having the empirical formula $C_{12}H_{11}BrF_3NO_3S$ are obtained (M=402.19 g).

The corresponding yield is 94%.

Stage I

The procedure is carried out as in Stage H of Example 1 with 8.73 g of the product obtained in the preceding stage, 5.67 g of methanesulfonic anhydride, 3.4 ml of triethylamine, 17 ml of benzylhydroxylamine and 80 ml of dichloromethane. 5.9 g of the compound ethyl trans-3-bromo-4,5,6,7-tetrahydro-7-[(phenylmethoxy)amino]-5-(trifluoroacetyl)thieno[3,2-c]pyridine-4-carboxylate having the empirical formula $C_{19}H_{18}BrF_3N_2O_4S$ are obtained (M=507.33 g).

The corresponding yield is 50%.

Stage J 0.05 g of the compound obtained in the preceding stage is dissolved in 1.25 ml of methanol and 0.5 ml of THF in a round-bottomed flask. The solution is cooled to 0° C. and placed under argon. The medium is stirred and 0.007 g of $NaBH_4$ and 0.013 g of $CaCl_2$ powder are added. Once the gaseous emission ceases, the reaction medium is poured over a 1 M $NaH_2PO_4$ solution; the aqueous phase is extracted with a heptane/ethyl acetate 1/2 mixture at 0° C. several times. The organic phases are combined, dried over magnesium sulfate, and then concentrated under reduced pressure. 44 mg of crude product are obtained which are purified by chromatography on silica, eluting with a heptane/ethyl acetate 1/2 mixture. After evaporation of the solvents, 14.6 mg of the compound ethyl trans-3-bromo-4,5,6,7-tetrahydro-7-[(phenylmethoxy)amino]thieno[3,2-c]pyridine-4-carboxylate having the empirical formula $C_{17}H_{19}BrN_2O_3S$ are obtained (M=411.32 g).

The corresponding yield is 36%.

Stage K

The procedure is carried out as in Stage K of Example 1 with 4.5 g of the product obtained in the preceding stage, 2.84 ml of triethylamine and 0.6 ml of diphosgene and 1215 ml of acetonitrile. 328 mg of the compound ethyl trans-3-bromo-4,6,7,8-tetrahydro-6-oxo-7-(phenylmethoxy)-5,8-methano-5H-thieno[2,3-e][1,3]diazepine-4-carboxylate having the empirical formula $C_{18}H_{17}BrN_2O_4S$ are obtained (M=437.32 g).

The corresponding yield is 7.6%.

Stage L

The procedure is carried out as in Stage M of Example 19 with 308 mg of the compound obtained in the preceding stage, 2.86 ml of a 2 M $Na_2CO_3$ solution, 71.8 mg of $Pd(P\phi_3)_4$ and 148.2 mg of 4-fluorophenylboronic acid and 15.24 ml of toluene. 109 mg of the compound ethyl trans-3-(4-fluorophenyl)-4,6,7,8-tetrahydro-6-oxo-7-(phenylmethoxy)-5,8-methano-5H-thieno[2,3-e][1,3]diazepine-4-carboxylate having the empirical formula $C_{24}H_{23}FN_2O_4S$ are obtained (M=452.52 g).

The corresponding yield is 34%.

Stage M

The procedure is carried out as indicated in Stage M of Example 1 with 50 mg of the product obtained in the preceding stage, 50 mg of 30% palladium on carbon and 0.8 ml of methanol and 2 ml of THF. The compound ethyl trans-3-(4-fluorophenyl)-4,6,7,8-tetrahydro-7-hydroxy-6-oxo-5,8-methano-5H-thieno[2,3-e][1,3]diazepine-4-carboxylate having the empirical formula $C_{17}H_{15}FN_2O_4S$ is obtained with a quantitative yield (M=362.38 g).

Stage N

The procedure is carried out as in Stage M of Example 1 with the compound obtained in the preceding stage and 53 mg of the pyridine-$SO_3$ complex and 0.8 ml of pyridine. The product obtained is treated as in Stage R of Example 12 with 15 g of Dowex resin. 15.4 mg of the compound sodium salt of ethyl trans-3-(4-fluorophenyl)-4,6,7,8-tetrahydro-6-oxo-7-(sulfoxy)-5,8-methano-5H-thieno[2,3-e][1,3]diazepine-4-carboxylate having the empirical formula $C_{17}H_{14}FN_2O_7S_2$, Na are obtained (M=464.43 g).

The corresponding yield is 30%.

LC/MS (negative electrospray), m/z: $M^-$=441.

Proton NMR, $D_2O$, 300 MHz, chemical shift and multiplicity:

0.95 (t): CO—O—$CH_2$—$CH_3$; 3.97 (m): CO—O—$CH_2$—$CH_3$; 3.58 (broad d), 3.79 (broad d): N—$CH_2$—CH—C≡; 5.07 (broad s): N—$CH_2$—CH—C≡; 5.45 (s): N—CH—C≡; 7.17 (m) and 7.31 (m): the 4 aromatic H of the fluorinated nucleus; 7.35 (s): S—CH≡.

Example 45

Sodium Salt of trans-2,5,6,8-tetrahydro-6-oxo-2-phenyl-5-(sulfoxy)-4H-4,7-methanopyrazolo[3,4-e][1,3]diazepine-8-carboxamide Stage A 54.2 mg of the product obtained in Stage K of Example 1 are dissolved in 2 ml of dichloromethane in the presence of 40.6 mg of phenylboronic acid, in a round-bottomed flask. A suspension is obtained to which 45 mg of $Cu(OAc)_2$ and 2 µl of pyridine and 125 mg of 4 Å sieve are added. The medium is stirred at 20° C. for 3 h 30 min and then the reaction medium is concentrated under reduced pressure. The residue obtained is purified by chromatography on silica, eluting with a methylene chloride/acetone/triethylamine 95/5/0.1% mixture. 33 mg of the compound methyl trans-2,5,6,8-tetrahydro-6-oxo-2-phenyl-5-(phenylmethoxy)-4H-4,7-methanopyrazolo[3,4-e][1,3]diazepine-8-carboxylate having the empirical formula $C_{22}H_{20}N_4O_4$ are obtained (M=404.43 g).

The corresponding yield is 50%.

Stage B

The procedure is carried out as in Stage A of Example 7 with 81 mg of the product obtained in the preceding stage, 1.7 ml of dioxane, 1.7 ml of water and 0.22 ml of 1 N sodium hydroxide. 70 mg of the compound trans-2,5,6,8-tetrahydro-6-oxo-2-phenyl-5-(phenylmethoxy)-4H-4,7-methanopyrazolo[3,4-e][1,3]diazepine-8-carboxylic acid having the empirical formula $C_{21}H_{18}N_4O_4$ are obtained (M=390.4 g).

The corresponding yield is 89.5%.

Stage C

The procedure is carried out as in Stage B of Example 7 with 70 mg of the product obtained in the preceding stage, 2.8 ml of DMF, 114 mg of BOP, 37 mg of HOBt, 20 mg of $NH_4Cl$ and 125 µl of DIPEA. 67.5 mg of the compound trans-2,5,6,8-tetrahydro-6-oxo-2-phenyl-5-(phenylmethoxy)-4H-4,7- methanopyrazolo[3,4-e][1,3]diazepine-8-carboxamide having the empirical formula $C_{21}H_{19}N_5O_3$ are obtained (M=389.42 g).

The corresponding yield is 95%.

Stage D

The procedure is carried out as in Stage M of Example 1 with 67.5 mg of the product obtained in the preceding stage, 5 ml of methanol, 4 ml of THF, and 60 mg of 30% palladium on carbon. 48 mg of the compound trans-2,5,6,8-tetrahydro-5-hydroxy-6-oxo-2-phenyl-4H-4,7-methanopyrazolo[3,4-e][1,3]diazepine-8-carboxamide having the empirical formula $C_{14}H_{13}N_5O_3$ are obtained (M=299.29 g).

The corresponding yield is 92%.

Stage E

The procedure is carried out as in Stage N of Example 1 with 48 mg of the product obtained in the preceding stage, 5 ml of pyridine, 77 mg of the pyridine-$SO_3$ complex. The product obtained is purified by chromatography on silica, eluting with a dichloromethane/ethanol/triethylamine 6/4/0.1% mixture. 50 mg of the compound triethylammonium salt of trans-2,5,6,8-tetrahydro-6-oxo-2-phenyl-5-(sulfoxy)-4H-4,7-methanopyrazolo[3,4-e][1,3]diazepine-8-carboxamide having the empirical formula $C_{20}H_{28}N_6O_6S$, $C_6H_{15}N$ are obtained (M=480.55 g).

The corresponding yield is 64%.

Stage F

The procedure is carried out as in Stage R of Example 12 with 50 mg of the product obtained in the preceding stage and 35 g of Dowex resin. 34 mg of the compound sodium salt of trans-2,5,6,8-tetrahydro-6-oxo-2-phenyl-5-(sulfoxy)-4H-4,7-methanopyrazolo[3,4-e][1,3]diazepine-8-carboxamide having the empirical formula $C_{14}H_{12}N_5O_6S$,Na are obtained (M=401.34 g).

The corresponding yield is 81%.

LC/MS (negative electrospray), m/z: $M^-$=378.

Proton NMR, $D_2O$ to 300 MHz, chemical shift and multiplicity:

3.45 (d), 3.83 (dd): N—$CH_2$—CH—C=; 5.07 (d): N—$CH_2$—$\underline{CH}$—C=; 5.35 (s): N—$\underline{CH}$—C=C=; 7.43 (broad t), 7.54 (broad t), 7.65 (broad d), 8.28 (s): the 5H of the aromatic nucleus.

Example 46

Sodium Salt of 1,4,5,8-tetrahydro-1-phenyl-5-(sulfoxy)-6H-4,7-methanopyrazolo[3,4-e][1,3]diazepin-6-one Stage A 5.51 g of the product obtained in Stage A1 of Example 2 are dissolved in 100 ml of ethanol, in a round-bottomed flask. 2.23 ml of phenylhydrazine are added and then the solution is stirred for one hour at room temperature. The reaction medium is next concentrated under vacuum. 6.71 g of the compound 1,1-dimethylethyl 3,5-dioxo-4-[(2-phenylhydrazino)methylene]-1-piperidinecarboxylate are obtained with a quantitative yield.

Stage B 6.71 g of the product obtained in the preceding stage are dissolved in 145 ml of acetic acid. This solution is heated under reflux for one hour and then the acetic acid is evaporated off. Toluene is added to the residue and the medium is again evaporated off. 7.3 g of crude product are obtained, which product is purified by chromatography on silica, eluting with a methylene chloride/acetone 95/5 mixture. 1.82 g of the compound 1,1-dimethylethyl 1,4,5,7-tetrahydro-4-oxo-1-phenyl-6H-pyrazolo[3,4-c]pyridine-6-carboxylate having the empirical formula $C_{17}H_{19}N_3O_3$ are obtained (M=313.36 g).

The corresponding yield is 28%.

Stage C 300 mg of the product obtained in the preceding stage are mixed with 10 ml of ethanol. 3 ml of dichloromethane are added followed by 115 mg of $NH_2O$—$CH_2$—CH—$CH_2$—HCl and 0.23 ml of pyridine. The medium is stirred at 20° C. for 3 hours and then the reaction medium is diluted with dichloromethane. The solution is washed with water and the organic phase is dried over magnesium sulfate and then concentrated under reduced pressure. 355 mg of the compound 1,1-dimethylethyl 1,4,5,7-tetrahydro-1-phenyl-4-[(2-propenyloxy)imino]-6H-pyrazolo[3,4-c]pyridine-6-carboxylate having the empirical formula $C_{20}H_{24}N_4O_3$ are obtained (M=368.44 g).

The corresponding yield is quantitative.

Stage D 0.355 g of the product obtained in the preceding stage is dissolved in 5 ml of acetic acid. The solution is cooled to 10° C. and 500 mg of $NaBH_3CN$ are added in several portions. The medium is stirred for 5 hours at room temperature and then the reaction medium is diluted with 150 ml of ethyl acetate. The medium is cooled to 0° C. before being neutralized with 35 ml of a 2 N sodium hydroxide solution. The medium is further stirred for 15 minutes at 0° C. and extracted with ethyl acetate. The organic phases are washed with 1 N aqueous sodium hydroxide solutions and then dried over magnesium sulfate. After evaporation of the solvent under reduced pressure, 360 mg of crude product are obtained which are purified by chromatography on silica, eluting with a methylene chloride/acetone 95/5 mixture. After evaporation of the solvents, 310 mg of the compound 1,1-dimethylethyl1, 4,5,7-tetrahydro-1-phenyl-4-[(2-propenyloxy)amino]-6H-pyrazolo [3,4-c]pyridine-6-carboxylate having the empirical formula $C_{20}H_{26}N_4O_3$ are obtained (M=370.46 g).

The corresponding yield is 86%.

Stage E

The procedure is carried out as in Stage I of Example 1 with 305 mg of the product obtained in the preceding stage, 3 ml of ethyl acetate, 3 ml of a 5.5 M HCl solution in ethyl acetate. 256 mg of the compound 4,4,6,7-tetrahydro-1-phenyl-4-[(2-propenyloxy)amino]-1H-pyrazolo[3,4-c]pyridine dichloride having the empirical formula $C_{15}H_{18}N_4O.3HCl$ are obtained (M=379.72 g).

The corresponding yield is 90%.

Stage F

The procedure is carried out as in Stage K of Example 1 with 197 mg of the product obtained in the preceding stage, 32 ml of acetonitrile, 0.44 ml of triethylamine, and 40 µl of diphosgene. 76 mg of the compound 1,4,5,8-tetrahydro-1-phenyl-5-(2-propenyloxy)-6H-4,7-methanopyrazolo[3,4-e][1,3]diazepin-6-one having the empirical formula $C_{16}H_{16}N_4O_2$ are obtained (M=296.33 g).

The corresponding yield is 49%.

Stage G

The procedure is carried out as in Stage G of Example 18 with 71 mg of the derivative obtained in the preceding stage, 7 ml of dichloromethane, 35 µl of acetic acid and 139 mg of $Pd(P\phi_3)_4$. The product obtained is then treated with 8 ml of pyridine and 153 mg of the pyridine-$SO_3$ complex. 136 mg of the compound 1-propenyltriphenylphosphonium salt of 1,4,5,8-tetrahydro-1-phenyl-5-(sulfoxy)-6H-4,7-methanopyrazolo[3,4-e][1,3]diazepin-6-one having the empirical formula $C_{21}H_{20}P$, $C_{13}H_{11}N_4O_5S$ are obtained (M=638.69 g).

The corresponding yield is 71.8%.

Stage H

The procedure is carried out as in Stage R of Example 12 with 136 mg of the product obtained in the preceding stage and 45 g of Dowex resin. 67 mg of the compound sodium salt of 1,4,5,8-tetrahydro-1-phenyl-5-(sulfoxy)-6H-4,7-methanopyrazolo[3,4-e][1,3]diazepin-6-one having the empirical formula $C_{13}H_{11}N_4NaO_5S$ are obtained (M=358.31 g).

The corresponding yield is 88%.

LC/MS (negative electrospray), m/z: $M^-$=335 and $(2M+H)^-$=671.

Proton NMR, $D_2O$, 300 MHz, chemical shift and multiplicity:

5.04 (d): N—$CH_2$—CH—C≡; 3.48 (d) and 3.84 (dd): N—$CH_2$—CH—C≡; 4.48 and 4.74: N—CH$_2$—C≡; 7.50 (m), 7.57 (m), 7.45 (m): the 5H of the aromatic nucleus; 7.85 (s): N═CH—C≡.

Example 47

Sodium Salt of trans-4,5,6,8-tetrahydro-6-oxo-1-phenyl-5-(sulfoxy)-1H-4,7-methanopyrazolo[3,4-e][1,3]diazepine-8-carboxamide Stage A The procedure is carried out as in Stage C of Example 1 with 312 mg of the product obtained in Stage B of Example 46, 20 ml of methanol and 38 mg of $NaBH_4$. 312 mg of the compound 1,1-dimethylethyl 1,4,5,7-tetrahydro-4-hydroxy-1-phenyl-6H-pyrazolo[3,4-c]pyridine-6-carboxylate having the empirical formula $C_{16}H_{21}N_3O_3$ are obtained (M=315.38 g).

The corresponding yield is 99%.

Stage B

The procedure is carried out as in Stage G of Example 1 with 160 mg of the product obtained in the preceding stage, 4 ml of anhydrous THF and 0.89 ml of a 1.7 M solution of tert-butyllithium in pentane and in the presence of a gaseous stream of $CO_2$. The product obtained is next acidified with 2 N HCl and then treated with diazomethane and 115 mg of the compound 6-(1,1-dimethylethyl) and 7-methyl 1,4,5,7-tetrahydro-4-hydroxy-1-phenyl-6H-pyrazolo[3,4-c]pyridine-6,7-dicarboxylate having the empirical formula $C_{19}H_{23}N_3O_5$ are obtained (M=373.41 g).

The corresponding yield is 60%.

Stage C

The procedure is carried out as in Stage H of Example 1 with 157 mg of the product obtained in the preceding stage, 5 ml of dichloromethane, 90 μl of triethylamine, 110 mg of $MS_2O$ and 156 mg of benzylhydroxylamine. 102 mg of the compound 6-(1,1-dimethylethyl) and 7-methyl 1,4,5,7-tetrahydro-1-phenyl-4-[(phenylmethoxy)amino]-6H-pyrazolo[3,4-c]pyridine-6,7-dicarboxylate having the empirical formula $C_{26}H_{30}N_4O_5$ are obtained (M=478.55 g).

The corresponding yield is 50.6%.

Stage D

The procedure is carried out as in Stage I of Example 1 with 102 mg of the product obtained in the preceding stage, 1 ml of ethyl acetate, 1 ml of methanol and 1 ml of a 5.5 M HCl solution in ethyl acetate. 91 mg of the compound methyl 4,5,6,7-tetrahydro-1-phenyl-4-[(phenylmethoxy)amino]-1H-pyrazolo[3,4-c]pyridine-7-carboxylate dihydrochloride having the empirical formula $C_{21}H_{22}N_4O_3.3HCl$ are obtained (M=487.82 g).

Stage E

The procedure is carried out as in Stage K of Example 1 with 90 mg of the compound obtained in the preceding stage, 10 ml of acetonitrile, 150 ml of triethylamine, 14 μl of diphosgene. 72 mg of the compound methyl trans-4,5,6,8-tetrahydro-6-oxo-1-phenyl-5-(phenylmethoxy)-1H-4,7-methanopyrazolo[3,4-e][1,3]diazepine-8-carboxylate having the empirical formula $C_{22}H_{20}N_4O_4$ are obtained (M=404.43 g).

The corresponding yield on both stages D and E is 84%.

Stage F

The procedure is carried out as in Stage A of Example 7 with 72 mg of the product obtained in the preceding stage, 1.5 ml of dioxane, 1.5 ml of water and 0.2 ml of a 1 N sodium hydroxide solution. 69 mg of the compound trans-4,5,6,8-tetrahydro-6-oxo-1-phenyl-5-(phenylmethoxy)-1H-4,7-methanopyrazolo[3,4-e][1,3]diazepine-8-carboxylic acid having the empirical formula $C_{21}H_{18}N_4O_4$ are obtained (M=390.4 g).

The corresponding yield is 99%.

Stage G

The procedure is carried out as in Stage D of Example 7 with 68 mg of the product obtained in the preceding stage, 2 ml of DMF, 112 mg of BOP, 36 mg of HOBt, 20 mg of $NH_4Cl$ and 123 μl of DIPEA. 50 mg of the compound trans-4,5,6,8-tetrahydro-6-oxo-1-phenyl-5-(phenylmethoxy)-1H-4,7-methanopyrazolo[3,4-e][1,3]diazepine-8-carboxamide having the empirical formula $C_{21}H_{19}N_5O_3$ are obtained (M=389.42 g).

The corresponding yield is 72%.

Stage H

The procedure is carried out as in Stage M of Example 1 with 50 mg of the compound obtained in the preceding stage, 5 ml of methanol, 95 mg of 10% palladium on carbon and 4 ml of THF. 36.8 mg of the compound trans-4,5,6,8-tetrahydro-5-hydroxy-6-oxo-1-phenyl-1H-4,7-methanopyrazolo[3,4-e][1,3]diazepine-8-carboxamide having the empirical formula $C_{14}H_{13}N_5O_3$ are obtained (M=299.29 g).

The corresponding yield is 95%.

Stage I

The procedure is carried out as in Stage N of Example 1 with 36.8 mg of the product obtained in the preceding stage, 5 ml of pyridine, 60 mg of the pyridine-$SO_3$ complex. The product obtained is treated as indicated in Stage R of Example 12 with 25 g of Dowex resin. 24 mg of the compound sodium salt of trans-4,5,6,8-tetrahydro-6-oxo-1-phenyl-5-(sulfoxy)-1H-4,7-methanopyrazolo[3,4-e][1,3]diazepine-8-carboxamide having the empirical formula $C_{14}H_{12}N_5O_6S,Na$ are obtained (M=401.34 g).

The corresponding yield is 48%.

LC/MS (negative electrospray), m/z: $M^-$=378. $(2M+Na)^-$=779.

Proton NMR, $D_2O$, 300 MHz, chemical shift and multiplicity:

3.40 (d), 3.76 (dd): N—$CH_2$—CH═C≡; 5.07 (d): N—$CH_2$—CH═C≡; 5.62 (s): N—CH—C≡; 7.50 (m), 7.55 (m), 7.44 (m): the 5H of the aromatic nucleus.

PHARMACOLOGICAL STUDY OF THE PRODUCTS OF THE INVENTION

Activity In Vitro, Method of Dilutions in Liquid Medium

A series of tubes is prepared into which the same quantity of sterile nutrient medium is distributed. Increasing quantities of the product to be studied are distributed into each tube, and then each tube is inoculated with a bacterial strain. After incubating for twenty-four hours in an oven at 37° C., the inhibition of growth is assessed by transillumination, which makes it possible to determine the minimum inhibitory concentrations (MIC) expressed in μg/ml.

Tests are thus carried out with the following products of the invention:
- the triethylammonium salt of 5,6-dihydro-6-oxo-$N^2$-phenyl-5-(sulfoxy)-4H-4,7-methanopyrazolo[3,4-e][1,3]diazepine-2,8(8H)-dicarboxamide (A),
- the sodium salt of 4,5,6,8-tetrahydro-6-oxo-5-(sulfoxy)-1H-4,7-methanopyrazolo[3,4-e][1,3]diazepine-1-carboxamide (B),
- the sodium salt of 1,4,5,8-tetrahydro-1-[(4-methoxyphenyl)methyl]-5-(sulfoxy)-6H-4,7-methanopyrazolo[3,4-e][1,3]diazepin-6-one (C),
- the sodium salt of trans-4,5,6,8-tetrahydro-2-(2-methylphenyl)-6-oxo-5-(sulfoxy)-4,7-methano-7H-thieno[2,3-e][1,3]diazepine-8-carboxamide (D),
- the sodium salt of trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide (E),
- the sodium salt of trans-2-(2-ethylphenyl)-4,5,6,8-tetrahydro-6-oxo-5-(sulfoxy)-4,7-methano-7H-thieno[2,3-e][1,3]diazepine-8-carboxamide (F),
- the sodium salt of trans-8-(2,3-dihydroxypropoxy)-1,2,3,5-tetrahydro-3-oxo-2-(sulfoxy)-1,4-methano-4H-2,4-benzodiazepine-5-carboxamide (G),
- the sodium salt of ethyl trans-3-(4-fluorophenyl)-4,6,7,8-tetrahydro-6-oxo-7-(sulfoxy)-5,8-methano-5H-thieno[2,3-e][1,3]diazepine-4-carboxylate (H),
- the sodium salt of trans-2,5,6,8-tetrahydro-6-oxo-2-phenyl-5-(sulfoxy)-4H-4,7-methanopyrazolo[3,4-e][1,3]diazepine-8-carboxamide (I),
- the sodium salt of 1,4,5,8-tetrahydro-1-phenyl-5-(sulfoxy)-6H-4,7-methanopyrazolo[3,4-e][1,3]diazepin-6-one (J),
- the sodium salt of trans-4,5,6,8-tetrahydro-6-oxo-1-phenyl-5-(sulfoxy)-1H-4,7-methanopyrazolo[3,4-e][1,3]diazepine-8-carboxamide (K).

These compounds have the activities grouped together in the following table:

|  | | Compounds |
|---|---|---|
| Gram-positive MIC μg/ml at 24 hours | | |
| S. aureus SG511 | 0.3–40 | A to K |
| E. faecium M 78 L | 2.5–80 | A and C to K |
| S. pyogenes A561 | <0.15–2.5 | A to K |
| Gram-negative MIC μg/ml at 24 hours | | |
| E. coli UC1894 | <0.15–2.5 | B to G |
| E. coli 250HT7 | 0.3–80 | B,C,F,G |
| E. cloacac 1321E | <0.15–10 | B and D to G |
| E. coli K 12 | 1.2–10 | A and H to K |
| E. coli DB 10 | <0.15–2.5 | A and H to K |

The compounds according to the invention therefore show an antibacterial activity.

II/β-LACTAMASE INHIBITING ACTIVITY

The compounds of formula (I) and their pharmaceutically acceptable salts exhibit marked inhibitory activities against β-lactamases of various bacterial strains and these therapeutically advantageous properties may be determined in vitro on isolated α-lactamases:

A. Preparation of the β-lactamases Tem~1 and P99

The β-lactamases are isolated from bacterial strains resistant to penicillins and to cephalosporins (Tem1 and P99 are produced by E. coli 250HT21 and E. Cloacae 293HT6, respectively).

The bacteria are cultured in heart-brain broth at 37 g/l (DIFCO), at 37° C. They are harvested at the end of the exponential phase, cooled and centrifuged. The bacterial pellets are taken up in 50 mM sodium phosphate buffer pH 7.0 and again centrifuged. The bacteria are taken up in two volumes of this same buffer and lyzed by means of a French-Press kept at 4° C. After centrifugation for 1 h at 100 000 G, at 4° C., the supernatants containing the soluble fraction of the bacterial extracts are recovered and frozen at −80° C.

B. Determination of the β-lactamase Activity

The method uses, as substrate, Nitrocefin (OXOID), a chromogenic cephalosporin, whose product of hydrolysis by Beta-lactamases is red and absorbs at 485 nm. The β-lactamase activity is kinetically determined by measuring the variation in absorbance at 485 nm resulting from the hydrolysis of the substrate on a plate spectrophotometer (Spectra Max Plus from Molecular Devices). The experiments are performed at 37° C. The quantity of enzyme was normalized and the measurements are performed at the initial speed.

C. Determination of the β-lactamase Inhibiting Activity

Two measurements are carried out, without preincubation and with preincubation of the enzyme and of the inhibitor (5 min), in order to test the irreversibility of the reaction. The products are tested at 6 or 8 concentrations in duplicate. The reaction mixture contains 100 μM of Nitrocefin and 50 mM sodium phosphate buffer pH 7.0.

D. Calculations of the $IC_{50}$ Values

The rates of hydrolysis are measured with and without inhibitor. The concentration of inhibitor which inhibits by 50% the reaction of hydrolysis of Nitrocefin by the enzyme (IC50) is determined. The data processing is carried out with the aid of the GraFit software (Erathycus Software).

| EXAMPLE No. | $IC_{50}$ nM/TEM1 | $IC_{50}$ nM/P99 |
|---|---|---|
| 28 | 33 | 25 |
| 38 | 59 | 19 |
| 37 | 41 | 21 |
| 40 | 11 | 12 |
| 42 | 15 | 44 |
| 18 | 5 | 13 |
| 41 | 9 | 29 |
| 19 | 5 | 16 |
| 21 | 7 | 69 |
| 33 | 56 | 17 |
| 24 | 2 | 10 |
| 25 | 2 | 6 |
| 26 | 1 | 6 |
| 46 | 5 | 80 |
| 7 | 1 | 14 |
| 44 | 34 | 2 |
| 11 | 11 | 39 |
| 10 | 12 | 18 |
| 47 | 12 | 3 |
| 5 | 13 | 17 |
| 4 | 34 | 7 |
| 45 | 1 | 12 |
| 2 | 16 | 20 |
| 3 | 2 | 11 |
| 1 | 3 | 5 |
| 9 | 60 | 50 |

Examples of Pharmaceutical Compositions:

1) A pharmaceutical composition for injection was prepared in which the ingredients are the following:

| | |
|---|---|
| compound of the example | 500 mg |
| sterile aqueous excipient | qs 10 ml |

2) A pharmaceutical composition (lyophilisate) for injection was prepared, containing:

| | |
|---|---|
| on the one hand: compound of the example | 500 mg |
| on the other hand: Cefotaxime | 1 g |
| sterile aqueous excipient | qs 5 ml |

The two active ingredients may, if desired, be introduced separately into two separate ampoules or vials.

The invention claimed is:

1. A compound of the formula:

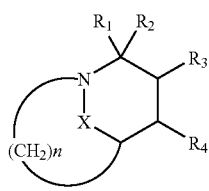

(I)

in which either:

a) $R_1$ is a radical selected from the group consisting of hydrogen, COOH, COOR, CN, $(CH_2)_{n'}R_5$, $CONR_6R_7$ and

R is selected from the group consisting of an alkyl radical containing from 1 to 6 carbon atoms, optionally substituted with one or more halogen atoms or with a pyridyl radical; a —$CH_2$-alkenyl radical containing in total from 3 to 9 carbon atoms; a (poly)alkoxyalkyl group containing 1 to 4 oxygen atoms and 3 to 10 carbon atoms; an aryl radical containing from 6 to 10 carbon atoms or an aralkyl radical containing from 7 to 11 carbon atoms, the aryl or aralkyl radical being optionally substituted with a radical selected from the group consisting of OH, $NH_2$, $NO_2$, alkyl containing from 1 to 6 carbon atoms, alkoxy containing from 1 to 6 carbon atoms and one or more halogen atoms;

$R_5$ is selected from the group consisting of COOH, CN, OH, $NH_2$, CO—$NR_6R_7$, COOR and OR radicals, R being as defined above, $R_6$ and $R_7$ are individually selected from the group consisting of hydrogen, an alkyl radical containing from 1 to 6 carbon atoms, an alkoxy radical containing from 1 to 6 carbon atoms, an aryl radical containing from 6 to 10 carbon atoms, an aralkyl radical containing from 7 to 11 carbon atoms and an alkyl radical containing from 1 to 6 carbon atoms which is substituted with a pyridyl radical;

n' is equal to 1 or 2, $R_3$ and $R_4$, together with the carbons to which they are attached, form a phenyl or a 5- or 6-membered aromatic heterocycle containing from 1 to 4 heteroatoms selected from nitrogen, oxygen and sulfur, which is substituted with one or more R' groups, R' being a radical selected from the group consisting of:

—$(O)_a$—$(CH_2)_b$—$(O)_a CONR_6R_7$, —$(O)_a$—$(CH_2)_b$—$OSO_3H$, —$(O)_a$—$(CH_2)_b$—$SO_3H$,

—$(O)_a$—$SO_2R$, —$(O)_a$—$SO_2$—$CHal_3$, —$(O)_a$—$(CH_2)_b$—$NR_6R_7$,

—$(O)_a$—$(CH_2)_b$—NH—COOR, —$(CH_2)_b$—COOH, —$(CH_2)_b$—COOR, —OR", OH,

—$(CH_2)_b$-phenyl,

—O—$(CH_2)_2$—O—$CH_3$, —O—$CH_2$-(2,2-dimethyl-1,3-dioxolan-4-yl), —CO—NH phenyl, —$(CH_2)_b$-5- or 6-membered aromatic heterocycle containing from 1 to 4 heteroatoms selected from nitrogen, oxygen and sulfur, each of said phenyl and said heterocycle being optionally substituted with one or more substituents selected from halogen, alkyl containing from 1 to 6 carbon atoms, alkoxy containing from 1 to 6 carbon atoms and $CF_3$, R, $R_6$ and $R_7$ being as defined above, R" being selected from alkyl radicals containing from 1 to 6 carbon atoms substituted with one or more radicals selected from hydroxy, protected hydroxy, oxo, halogen and cyano radicals, a being equal to 0 or 1 and b being an integer from 0 to 6, provided that, when R' is OH, $R_1$ is $CONR_6R_7$ in which one of $R_6$ and $R_7$ is an alkoxy containing from 1 to 6 carbon atoms; or b) $R_4$ is hydrogen or $(CH_2)_{n'_1}R_5$, wherein $n'_1$, is 0, 1 or 2 and $R_5$ is as defined above, and $R_1$ and $R_3$, together with the carbons to which they are attached, form a substituted phenyl or heterocycle, as defined above;

and, in both cases a) and b), $R_2$ is selected from the group consisting of hydrogen, halogen, R, $S(O)_m R$, OR, NHCOR, NHCOOR and $NHSO_2R$, R being as defined above and m being 0, 1 or 2, X is a divalent group —C(O)—B— linked to the nitrogen atom by the carbon atom, B is a divalent group selected from 1) —$NR_8$—$(CH_2)_{n''}$- linked to the carbonyl by the nitrogen atom, n" is 0 and $R_8$ is a radical selected from the group consisting of hydrogen, OH, R, OR, Y, OY, $Y_1$, $OY_1$, $Y_2$, $OY_2$, $Y_3$, O—$CH_2$—$CH_2$—$S(O)_m$—R, $SiRaRbRc$ and $OSiRaRbRc$, wherein each of Ra, Rb and Rc is a linear or branched alkyl containing from 1 to 6 carbon atoms or an aryl containing from 6 to 10 carbon atoms, and R and m are as defined above;

Y is selected from the group consisting of COH, COR, COOR, $CONH_2$, CONHR, CONHOH, $CONHSO_2R$, $CH_2COOH$, $CH_2COOR$, CHF—COOH, CHF—COOR, $CF_2$—COOH, $CF_2$—COOR, CN, $CH_2CN$, $CH_2CONHOH$, $CH_2CONHCN$, $CH_2$tetrazole, protected $CH_2$tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$;

$Y_1$ is selected from the group consisting of $SO_2R$, $SO_2NHCOH$, $SO_2NHCOR$, $SO_2NHCOOR$, $SO_2NHCONHR$, $SO_2NHCONH_2$ and $SO_3H$;

$Y_2$ is selected from the group consisting of $PO(OH)_2$, $PO(OR)_2$, PO(OH)(OR) and PO(OH)(R);

$Y_3$ is selected from the group consisting of tetrazole, tetrazole substituted with R, squarate, NH or NRtetrazole, NH or NRtetrazole substituted with R, $NHSO_2R$, $NRSO_2R$, $CH_2$tetrazole and $CH_2$tetrazole substituted with R, R being as defined above, and n is 1, or one of its salts with a base or an acid.

2. The compound as claimed in claim 1, wherein $R_2$ is a hydrogen atom.

3. The compound as claimed in claim 1, wherein $R_3$ and $R_4$ together form a substituted phenyl or a substituted heterocycle.

4. The compound as claimed in claim 1, wherein $R_3$ and $R_4$ together form a substituted phenyl or a substituted heterocycle, wherein the substituted heterocycle is a substituted thienyl or a pyrazolyl substituted with one or more of the substituents therefore as defined in claim 1.

5. The compound as claimed in claim 1, wherein $R_1$ is selected from the group consisting of hydrogen, $COOCH_3$, $COOC_2H_5$, $CONH_2$, $CONHCH_3$ and $CONHOCH_3$.

6. The compound as claimed in claim 1, wherein $R_8$ is selected from OY and $OY_1$, where Y is selected from the group consisting of $CH_2COOH$, $CH_2COOR$, $CHF-COOH$, $CHF-COOR$, $CF_2-COOH$, $CF_2-COOR$, CN, $CH_2CN$, $CH_2CONHOH$, $CH_2CONHCN$, $CH_2$tetrazole, protected $CH_2$tetrazole, $CH_2SO_3H$ $CH_2SO_2R$, $CH_2PO(OR)_2$, $CH_2PO(OR)(OH)$, $CH_2PO(R)(OH)$ and $CH_2PO(OH)_2$ or $Y_1$ is selected from the group consisting of $SO_2R$, $SO_2NHCOR$, $SO_2NHCOOR$, $SO_2NHCONHR$ and $SO_3H$, R being as defined in claim 1.

7. The compound as claimed in claim 1, wherein R' is selected from consisting of —O—$CH_2$—CHOH—$CH_2OH$, —$CH_2$—$CH_2$—$NH_2$, —$CH_2$—$COOC_2H_5$, —$CH_2$—$CH_2$-phenyl, —O—CO—NHphenyl, —O—CO—$NHC_2H_5$, —O—$SO_2$—$CF_3$, —O—$(CH_2)_2$—O—$SO_3H$, —O—$(CH_2)_2$—O—$CH_3$, —$CH_2$—COOH, —O—$CH_2$-(2,2-dimethyl-1,3-dioxolan-4-yl), —CO—$NH_2$, —CO—NH phenyl, —$CH_2$—(p-$OCH_3$ phenyl) and phenyl optionally substituted with a substituent selected from $CH_3$, $C_2H_5$, F and $CF_3$.

8. A compound of formula (I), as defined in claim 1, selected from the group consisting of:

the triethylammonium salt of 5,6dihydro-6-$N^2$-phenyl-5-(sulfoxy)-4H-4,7-methanopyrazolo[3,4e][1,3]diazepine-2,8(8H)dicarboxamide, the sodium salt of 4,5,6,8-tetrahydro-6-oxo-5-(sulfoxy)-1H-4,7-methanopyrazolo[3,4-e][1,3]diazepine-1-carboxamide, the sodium salt of 1,4,5,8Tetrahydro-1[(4-methoxyphenyl) methyl]-5-(sulfoxy)-6H-4,7methanopyrazolo[3,4-e]diazepin-6-one, the sodium salt of trans-4,5,6,8-tetrahydro-2-(2-methylphenyl)-6-oxo-5-(sulfoxy)-4,7-methano-7H-thieno[2,3-e][1,3]diazepine-8-carboxamide, the sodium salt of trans-4,5,6,8-tetrahydro-6-oxo-5-(sulfoxy)-2-[2-(trifluoromethyl)phenyl]-4,7-methano-7H-thieno[2,3-e][1,3]diazepine-8-carboxamide, the sodium salt of trans-2-(2-ethylphenyl)-4,5,6,8-tetrahydro-6-oxo-5-(sulfoxy)-4,7-methano-7H-thieno[2,3-e][1,3]diazepine-8-carboxamide, the sodium salt of trans-8-(2,3-dihydroxypropoxy)-1,2,3,5-tetrahydro-3-oxo-2-(sulfoxy)-1,4-methano-4H-2,4-benzodiazepine-5-carboxamide, the sodium salt of ethyl trans-3-(4-fluorophenyl)-4,6,7,8-tetrahydro-6-oxo -7-(sulfoxy)-5,8-methano-5H-thieno[2,3-e][1,3]diazepine-4-carboxylate, the sodium salt of trans-2,5,6,8-tetrahydro-6-oxo-2-phenyl-5-(sulfoxy)-4H -4,7-methanopyrazolo[3,4-e][1,3] diazepine-8-carboxamide, the sodium salt of 1,4,5,8-tetrahydro-1-phenyl-5-(sulfoxy)-6H-4,7-methanopyrazolo[3,4-e][1,3]diazepin-6-one, the sodium salt of trans-4,5,6,8-tetrahydro-6-oxo-1-phenyl-5-(sulfoxy)-1H -4,7-methanopyrazolo[3,4-e][1,3]diazepine-8-carboxamide, the triethylammonium salt of methyl trans-2,5,6,8-tetrahydro-6-oxo-2-(phenylmethyl)-5-(sulfoxy)-4H-4,7-methanopyrazolo[3,4-e][1,3]diazepine -8-carboxylate, the triethylammonium salt of methyl trans-4,5,6,8-tetrahydro-6-oxo-1-(2-phenylethyl)-5-(sulfoxy)-1H-4,7-methanopyrazolo[3,4-e][1,3]diazepine-8-carboxylate, the triethylammonium salt of ethyl trans-4,5,6,8-tetrahydro-8-(methoxycarbonyl)-6-oxo-5-(sulfoxy)-1H-4,7-methanopyrazolo[3,4-e][1,3]diazepine-1-acetate, the triethylammonium salt of ethyl trans-5,6-dihydro-8-(methoxycarbonal)-6oxo-5(sulfoxy)-4H -4,7-methanopyrazolo [3,4-e][1,3]diazepine-2(8H)-acetate, the di(triethylammonium) salt of trans-5,6-dihydro-8-(methoxycarbonyl)-6-oxo-5-sulfoxy-4H-4,7-methanopyrazolo [3,4-e][1,3]diazepine-2(8H)acetic acid, the pyridinium salt of methyl trans-1-(aminocarbonyl)-4,5,6,8-tetrahydro-6-oxo-5-(sulfoxy)-1H-4,7-methanopyrazolo[3,4-e][1,3]diazepine-8-carboxylate, the pyridinium salt of methyl trans-2-(aminocarbonyl)-2,5,6,8-tetrahydro-6-oxo-5-(sulfoxy)-4H-4,7-methanopyrazolo[3,4-e]diazepine-8-carboxylate, the sodium salt of methyl trans-2-(4-fluorophenyl)-4,5,6,8-tetrahydro-6-oxo-5-(sulfoxy)-4,7-methano-7H-thieno[2,3-e][1,3]diazepine-8-carboxylate, the sodium salt of methyl trans-2(aminocarbonyl)-4,5,6,8-tetrahydro-6-oxo-5-(sulfoxy)-4,7-methano-7H-thienol[2,3-e][1,3]diazepine-8-carboxylate, the sodium salt of ethyl trans-1,2,3,5-tetrahydro-3-oxo-9-[[(phenylamino)carbonyl]oxy]-2-(sulfoxy)-1,4-methano-4H-2,4-benzodiazepine-5-carboxylate, the sodium salt of trans-1,2,3,5-tetrahydro-N-methoxy-8-[(2-methoxyethoxy)methoxy]-3-oxo-2-(sulfoxy)-1,4-methano-4H-2,4-benzodiazepine-5-carboxamide, the sodium salt of ethyl trans-1,2,3,5-tetrahydro-3-oxo-8-[[(phenylamino)carbonyl]oxy]-2-(sulfoxy)-1,4-methano-4H-2,4-benzodiazepine-5-carboxylate, the sodium salt of ethyl trans-8-[[(ethylamino)carbonyl]oxy]-1,2,3,5-tetrahydro-3-oxo-2-(sulfoxy)-1,4-methano-4H-2,4-benzodiazepine-5-carboxylate, the sodium salt of ethyl trans-1,2,3,5-tetrahydro-3-oxo-2-(sulfoxy)-8-[[(trifluoromethyl)sulfonyl]oxy]-1,4-methano-4H-2,4-benzodiazepine-5-carboxylate, the disodium salt of trans-1,2,3,5-tetrahydro-3-oxo-2-(sulfoxy)-8-[2-(sulfoxy)ethoxy]-1,4-methano-4H-2,4-benzodiazepine-5-carboxamide, the sodium salt of trans-8-[(2,2-dimethyl-1,3-dioxolan-4-yl)methoxy]-1,2,3,5-tetrahydro-3-oxo-2-(sulfoxy)-1,4-methano-4H-2,4-benzodiazepine -5-carboxamide, and the triethylammonium salt of methyl trans-2,5,6,8-tetrahydro-6-oxo-(2-phenylethyl)-5-(sulfoxy)-4H-4,7-methanopyrazolo[3,4-e][1,3]diazepine-8-carboxylate.

9. A method for preparing a compound as claimed in claim 1, which comprises:

a) reacting a carbonylating agent, where appropriate in the presence of a base, with a compound of formula (II):

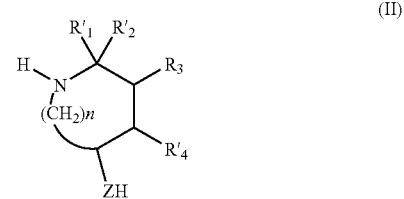

in which either:
a) $R'_1$ is selected from the group consisting of H, CN, protected COOH, $COOR_9$, $(CH_2)_n R'_5$, $CONR_6R_7$
$R_9$ is selected from the group consisting of alkyl containing from 1 to 6 carbon atoms, optionally substituted with one or more halogen atoms or with a pyridyl; —$CH_2$-alkenyl containing in total from 3 to 9 carbon atoms; aryl containing from 6 to 10 carbon atoms or aralkyl containing from 7 to 11 carbon atoms, the nucleus of the aryl or aralkyl being optionally substituted with a substituent selected from the group consisting of $NO_2$, protected OH, protected $NH_2$, alkyl containing from 1 to 6 carbon atoms, alkoxy containing from 1 to 6 carbon atoms and one or more halogen atoms;
$R'_5$ is selected from the group consisting of protected OH, CN, protected $NH_2$, CO—$NR_6R_7$, protected COOH, $COOR_9$, and $OR_9$, $R_9$ being as defined above; n', $R_6$ and $R_7$ are as defined in claim 1;
$R_3$ and $R'_4$, together with the carbons to which they are attached, form a phenyl or a 5- or 6-membered aromatic heterocycle containing from 1 to 4 heteroatoms selected from nitrogen, oxygen and sulfur, and optionally substituted with one or more $R_{10}$ groups, $R_{10}$ being selected from the group consisting of hydrogen; alkyl containing from 1 to 6 carbon atoms substituted with one or more substituents selected from hydroxy, oxo, halogen and cyano; alkenyl containing from 2 to 6 carbon atoms; halo; protected OH; —OR; and OR"; R" is as defined in claim 1, —$(CH_2)_b$-phenyl and —$(CH_2)_b$-heterocycle, each of said phenyl and heterocycle being optionally substituted, as defined in claim 1; or
b) $R'_4$ represents a hydrogen atom or $(CH_2)_{n'_1} R'_5$, $n'_1$ being 0, 1 or 2 and $R'_5$ being as defined above,
and $R'_1$ and $R_3$ together form an optionally substituted phenyl or heterocycle as defined above for $R_3$ and $R'_4$;
and, in both cases a) and b),
$R'_2$ is selected from the group consisting of hydrogen, halogen, $R_9$, $S(O)_m R_9$, $OR_9$, NHCOH, $NHCOR_9$, $NHCOOR_9$ and $NHSO_2R_9$, $R_9$ being as defined above and m being as defined in claim 1,
n being as defined in claim 1;
ZH is selected from the group consisting of $HNR'_8$—$(CH_2)_n$—, n" being as defined in claim 1 and $R'_8$ being selected from the group consisting of hydrogen, $R_9$, protected OH, $OR_9$, Y', OY', $Y'_1$, $OY'_1$, $Y'_2$, $OY'_2$, $Y'_3$, O—$CH_2$—$CH_2$—$S(O)_m$—R", SiRaRbRc and OSiRaRbRc, each of Ra, Rb and Rc individually being a linear or branched alkyl containing from 1 to 6 carbon atoms or an aryl containing from 6 to 10 carbon atoms, $R_9$ and m being as defined above,
Y' is selected from the group consisting of COH, $COR_9$, $COOR_9$, $CONH_2$, $CONHR_9$, $CONHSO_2R_9$, $CH_2COOR_9$, protected $CH_2$tetrazole, $CH_2SO_2R_9$, $CH_2PO(OR_9)_2$, protected CONHOH, protected $CH_2COOH$, protected $CH_2CONHOH$, protected $CH_2SO_3$, protected $CH_2PO(OR)(OH)$, protected $CH_2PO(R)(OH)$ and protected $CH_2PO(OH)_2$,
$Y'_1$ is selected from the group consisting of $SO_2R_9$, $SO_2NHCOH$, $SO_2NHCOR_9$, $SO_2NHCOOR_9$, $SO_2NHCONH_2$, $SO_2NHCONHR_9$ and protected $SO_3H$,
$Y'_2$ is selected from the group consisting of $PO(OR_9)_2$, protected $PO(OH)_2$, protected PO(OH)(OR) and protected PO(OH)(R),
$Y'_3$ is selected from the group consisting of protected tetrazole, tetrazole substituted with $R_9$, protected squarate, protected NHtetrazole, protected $NR_9$tetrazole, protected NH, $NR_9$tetrazole substituted with $R_9$, $NHSO_2R_9$ and $NSO_2R_9$, $R_9$ being as defined above, and n is as defined in claim 1; in order to obtain an intermediate compound of formula (III):

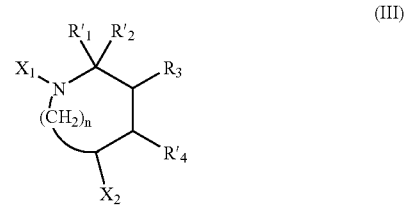

in which: $R'_1$, $R'_2$, $R_3$, $R'_4$ and n have the same meanings as above and either $X_1$ is hydrogen and $X_2$ is —Z—CO—$X_3$, $X_3$ representing the residue of the carbonylating agent, or $X_2$ is —ZH and $X_1$ is CO—$X_3$, $X_3$ being as defined above; and
b) cyclizing said intermediate in the presence of a base; and
c) where appropriate, step a) is preceded and/or step b) is followed by one or more of the following reactions, in an appropriate order:
protection of the reactive functional groups;
deprotection of the reactive functional groups;
esterification;
saponification;
sulfation;
phosphatization;
amidation;
acylation;
sulfonylation;
alkylation;
formation of a urea group;
reduction of carboxylic acids;
reduction of ketones and aldehydes to alcohols;
salification;
ion exchange;
resolution or separation of diastereoisomers;
oxidation of sulfide to sulfoxide and/or sulfone;
oxidation of aldehyde to acid;
oxidation of alcohol to ketone;
halogenation or dehalogenation;
carbamoylation;
carboxylation;
introduction of an azido group;
reduction of an azido to amine;
reactions of coupling of aromatic or heteroaromatic halides or triflates or of heterocyclic nitrogens with aryl- or heteroarylboronic acids;
reactions of coupling of aromatic or heteroaromatic halides or triflates with stannyl-containing reagents;
hydrogenation of double bonds;
dihydroxylation of double bonds;
cyanidation.

10. The method as claimed in claim 9, wherein the carbonylating agent is selected from the group consisting of phosgene, diphosgene, triphosgene, aryl, aralkyl, alkyl and alkenyl chloroformates, alkyl dicarbonates, carbonyldiimidazole and mixtures thereof.

11. The method as claimed in claim 9, wherein the carbonylation reaction occurs in the presence of a base.

12. The method as claimed in claim 9, wherein, in step b), the base is selected from the group consisting of amines, hydrides, alcoholates, amides and carbonates of alkali or alkaline earth metals.

13. The method as claimed in claim 12, wherein the base is an amine.

14. The method as claimed in claim 9, wherein the compound of formula (II) in which ZH is HNR'$_8$—(CH$_2$)$_{n''}$— in which n" is 0, R'$_8$ being as defined in claim 9, is obtained by a method wherein a compound of formula (IV):

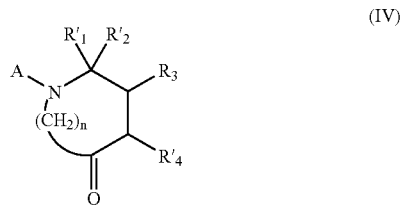

in which R'$_1$, R'$_2$ and n are as defined in claim 9, R$_3$ and R'$_4$ have the values defined in claim 9 or else values which are precursors of the values defined above and A represents hydrogen or a group protecting the nitrogen, is treated with a reducing agent, in order to obtain a compound of formula (V):

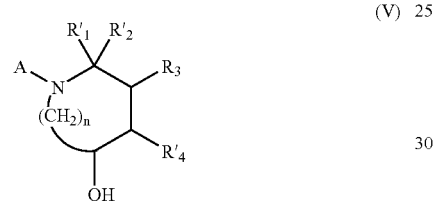

in which A, R'$_1$, R'$_2$, R$_3$, R'$_4$ and n are as defined in claim 9, and in which, where appropriate, the OH group is replaced with a leaving group, in order to obtain a compound of formula (VI):

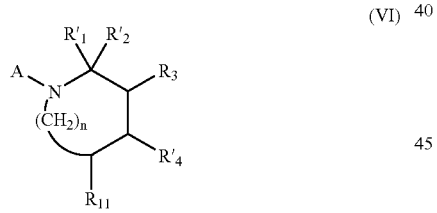

in which A, R'$_1$, R'$_2$, R$_3$, R'$_4$ and n are as defined in claim 9 and R$_{11}$ represents a leaving group, which compound (VI) is then treated with a compound of formula Z$_1$H$_2$ in which Z$_1$ is a divalent group —NR'$_8$, R'$_8$ being as defined in claim 9, in order to obtain a compound of formula (VIII):

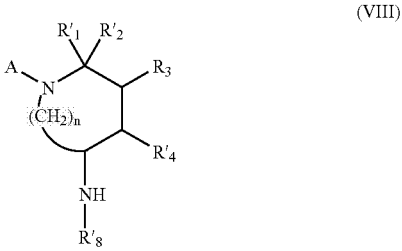

in which A, R'$_1$, R'$_2$, R$_3$, R'$_4$, n" and R'$_8$ are as defined in claim 9, and then, where appropriate, with an appropriate agent for deprotecting the nitrogen atom, and wherein, where appropriate, the intermediate of formula (IV), (V), (VIII) is subjected to one or more of the reactions described in step c) of the method of claim 9, in an appropriate order.

15. The method as claimed in claim 9, wherein the compound of formula (II) in which ZH is NHR'$_8$—(CH$_2$)$_{n''}$— in which n" is 0 is obtained by a method in which a compound of formula (IV) as defined above is treated with a compound of formula H$_2$NR'$_8$, in order to obtain a compound of formula (VII):

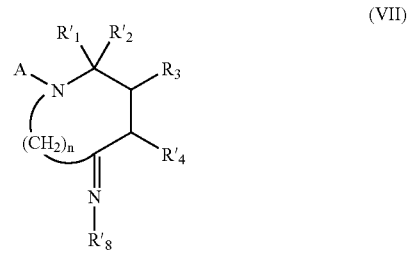

in which A represents hydrogen or a group protecting the nitrogen and wherein R'$_1$, R'$_2$, R$_3$, R'$_4$, n and R'$_8$ are as defined in claim 9, which compound of formula (VII) is reacted with a reducing agent in order to obtain a compound of formula (VIII):

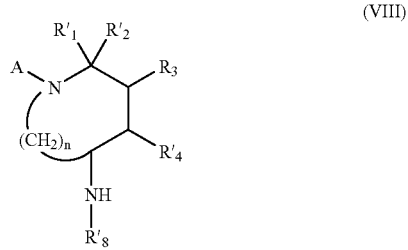

in which A is as defined above, R'$_1$, R'$_2$, R$_3$, R'$_4$, n" and R'$_8$ are as defined in claim 9, which compound of formula (VIII) is treated, where appropriate, with an appropriate agent for deprotecting the nitrogen atom, and wherein, where appropriate, the intermediate of formula (VII) or (VIII) is subjected to one or more of the reactions described in step c) of the method of claim 9, in an appropriate order.

16. A method of treating a bacterial infection comprising administering to a mammal in need thereof an antibacterially effective amount of a compound as defined in claim 1, or a salt thereof with a pharmaceutically acceptable acid or base.

17. A method of treating a bacterial infection comprising administering to a mammal in need thereof an antibacterially effective amount of a compound as defined in claim 8, or a salt thereof with a pharmaceutically acceptable acid or base.

18. A pharmaceutical composition containing, as an active ingredient, at least one compound as claimed in claim 1.

19. A pharmaceutical composition containing, as an active ingredient, at least one compound as claimed in claim 8.

20. A pharmaceutical composition containing, as an active ingredient, at least one compound as defined in claim 1 and at least one β-lactam medicament selected from the group consisting of amoxicillin, ampicillin, azlocillin, mezlocillin, aralcillin, hetacillin, bacamricillin, carbenicillin, sulbenicillin, ticarcillin, piperacillin, mecillinam, pivmecillinam, methicillin, ciclacillin, talamricillin, asroxicillin, oxacillin, cloxacillin, dicloxacillin, flucloxacillin, nafcillin, pivamricillin, cephalothin, cephaloridin, cefaclor, cefadroxil, cefamandole, cefazolin, cephalexin, cephradine, ceftizoxime, cefoxitin, cerhacetril, cefotiam, cefotaxime, cefsulodin, ceforerazone, cefmenoxime, cefmetazole, cephaloglvcin, cefonicid, cefodizime, cefpirome, ceftazidime, ceftriaxone, cefpiramide, cefburerazone, cefozopran, cefepim, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, imipenem, meropenem, biarenem, panirenem, aztreonam, carumonam, and their salts.

21. A pharmaceutical composition containing, as an active ingredient, at least one compound as defined in claim 8 and at least one β-lactam medicament selected from the group consisting of amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin, pivampicillin, cephalothin, cephaloridin, cefaclor, cefadroxil, cefamandole, cefazolin, cephalexin, cephradine, ceftizoxime, cefoxitin, cephacetril, cefotiam, cefotaxime, cefsulodin, cefoperazone, cefmenoxime, cefmetazole, cerhaloglvcin, cefonicid, cefodizime, cefpirome, ceftazidime, ceftriaxone, cefriramide, cefbuperazone, cefozopran, cefepim, cefoselis, cefluprenam, cefuzonam, cefpmizole, cefclidin, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbacef, latamoxef, imipenem, meropenem, biapenem, panipenem, aztreonam, carumonam. and their salts.

22. A method of treating a bacterial infection comprising administering to a mammal in need thereof an effective amount of a compound as defined in claim 1, or a salt thereof with a pharmaceutically acceptable acid or base and an antibacterially effective amount of a beta-lactam medicament agent selected from the group consisting of amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucloxacillin, nafcillin, pivampicillin, cephalothin, cephaloridin, cefaclor, cefadroxil, cefamandole, cefazolin, cephalexin, cephradine, ceftizoxime, cefoxitin, cephacetril, cefotiam, cefotaxime, cefsulodin, cefoperazone, cefmenoxime, cefmetazole, cephaloglvcin, cefonicid, cefodizime, cefpirome, ceftazidime, ceftriaxone, cefpiramide, cefbuperazone, cefozopran, cefepim, cefoselis, cefluprenam, cefuzonam, cefpimizole, cefclidin, cefixime, ceftibuten, cefdinir, cefrodoxime axetil, cefpodoxime proxetil. cefteram pivoxil, cefetamet rivoxil, cefcapene pivoxil, cefditoren pivoxil, cefuroxime, cefuroxime axetil, loracarbacef, latamoxef, imipenem, meropenem, biapenem, panipenem, aztreonam, carumonam, and their salts.

23. A method of treating a bacterial infection comprising administering to a mammal in need thereof an effective amount of a compound as defined in claim 8, or a salt thereof with a pharmaceutically acceptable acid or base and an antibacterially effective amount of a beta-lactam medicament agent selected from the group consisting of amoxicillin, ampicillin, azlocillin, mezlocillin, apalcillin, hetacillin, bacampicillin, carbenicillin, sulbenicillin, ticarcillin, piperacillin, mecillinam pivmecillinam, methicillin, ciclacillin, talampicillin, aspoxicillin, oxacillin, cloxacillin, dicloxacillin, flucloxacillin, nafcillin, pivampicillin, cephalothin, cephaloridin, cefaclor, cefadroxil, cefamandole, cefazolin, cephalexin, cephradine, ceftizoxime, cefoxitin, cephacetril, cefotiam, cefotaxime, cefsulodin, ceforerazone, cefmenoxime, cefmetazole, cephaloglvcin, cefonicid, cefodizime, cefrirome, ceftazidime, ceftriaxone, cefpiramide, cefburerazone, cefozopran, cefepim, cefoselis, cefluprenam, cefuzonam, cefpimizole, cefclidin, cefixime, ceftibuten, cefdinir, cefrodoxime axetil, cefrodoxime proxetil, cefteram pivoxil, cefetamet pivoxil, cefcapene pivoxil, cefditoren pivoxil, cefuroxime, cefuroxime axetil, loracarbacef, latamoxef, imirenem, meropenem, biarenem, panipenem, aztreonam, carumonam, and their salts.

* * * * *